(12) United States Patent
Hopkins et al.

(10) Patent No.: US 11,242,327 B2
(45) Date of Patent: Feb. 8, 2022

(54) ANALGESIC COMPOUNDS

(71) Applicant: RECURIUM IP HOLDINGS, LLC, San Diego, CA (US)

(72) Inventors: Chad Daniel Hopkins, San Diego, CA (US); Joseph Robert Pinchman, San Diego, CA (US); Kevin Duane Bunker, Escondido, CA (US); Deborah Helen Slee, Encinitas, CA (US); Brant Clayton Boren, San Diego, CA (US); Mehmet Kahraman, San Diego, CA (US)

(73) Assignee: Recurium IP Holdings, LLC, San Diego, CA (US)

( * ) Notice: Subject to any disclaimer, the term of this patent is extended or adjusted under 35 U.S.C. 154(b) by 0 days.

(21) Appl. No.: 16/613,397

(22) PCT Filed: May 11, 2018

(86) PCT No.: PCT/US2018/032417
§ 371 (c)(1),
(2) Date: Nov. 13, 2019

(87) PCT Pub. No.: WO2018/213140
PCT Pub. Date: Nov. 22, 2018

(65) Prior Publication Data
US 2020/0270221 A1    Aug. 27, 2020

Related U.S. Application Data

(60) Provisional application No. 62/506,512, filed on May 15, 2017.

(51) Int. Cl.
| | |
|---|---|
| *C07D 277/28* | (2006.01) |
| *C07D 213/38* | (2006.01) |
| *C07D 235/14* | (2006.01) |
| *C07D 239/26* | (2006.01) |
| *C07D 263/56* | (2006.01) |
| *C07D 277/64* | (2006.01) |
| *A61P 29/00* | (2006.01) |
| *A61P 25/04* | (2006.01) |
| *C07C 211/38* | (2006.01) |
| *C07C 211/40* | (2006.01) |
| *C07C 215/08* | (2006.01) |
| *C07C 217/52* | (2006.01) |
| *C07C 229/14* | (2006.01) |
| *C07C 235/14* | (2006.01) |
| *C07C 237/04* | (2006.01) |
| *C07C 271/24* | (2006.01) |

(52) U.S. Cl.
CPC ............ *C07D 277/28* (2013.01); *A61P 25/04* (2018.01); *A61P 29/00* (2018.01); *C07C 211/38* (2013.01); *C07C 211/40* (2013.01); *C07C 215/08* (2013.01); *C07C 217/52* (2013.01); *C07C 229/14* (2013.01); *C07C 235/14* (2013.01); *C07C 237/04* (2013.01); *C07C 271/24* (2013.01); *C07D 213/38* (2013.01); *C07D 235/14* (2013.01); *C07D 239/26* (2013.01); *C07D 263/56* (2013.01); *C07D 277/64* (2013.01)

(58) Field of Classification Search
CPC ... C07C 211/38; C07C 211/40; C07C 215/08; C07C 217/52; C07C 217/62; C07C 229/10; C07C 229/14; C07C 235/14; C07C 237/04; C07C 2602/38; C07C 271/24; C07D 277/28; C07D 213/26; C07D 235/14; C07D 239/26; C07D 263/56; C07D 277/22; C07D 277/64; C07D 213/38
See application file for complete search history.

(56) References Cited

U.S. PATENT DOCUMENTS

| | | |
|---|---|---|
| 5,262,417 A | 11/1993 | Gammill et al. |
| 5,385,906 A | 1/1995 | Gammill et al. |
| 5,405,550 A | 4/1995 | Michl et al. |
| 6,136,861 A | 10/2000 | Chenard |
| 9,447,025 B2 | 9/2016 | Bunker |
| 9,447,026 B2 | 9/2016 | Bunker |
| 9,693,975 B2 | 7/2017 | Bunker |
| 9,724,316 B2 | 8/2017 | Bunker |
| 10,189,780 B2 | 1/2019 | Bunker |
| 10,308,609 B2 | 6/2019 | Bunker |

(Continued)

FOREIGN PATENT DOCUMENTS

| | | |
|---|---|---|
| CN | 103588668 | 2/2014 |
| CN | 103588672 | 2/2014 |

(Continued)

OTHER PUBLICATIONS

Applequist et al. (Journal of Organic Chemistry, 1982, 47(25), pp. 4985-4995).*

Adcock et al., "Polar substituent effects in the bicyclo [1.1. 1] pentane ring system: Acidities of 3-substituted bicyclo [1.1. 1] pentane-1-carboxylic acids." *The Journal of organic chemistry* 70.3 (2005): 1029-1034.

Adcock et al., "Transmission of polar substituent effects across the bicyclo [1.1. 1] pentane ring system as monitored by 19F NMR shifts." *Magnetic Resonance in Chemistry* 38.2 (2000): 115-122.

(Continued)

*Primary Examiner* — Susanna Moore
(74) *Attorney, Agent, or Firm* — Knobbe, Martens, Olson & Bear, LLP

(57) ABSTRACT

Disclosed herein are compounds of Formulae (Ia), (Ib), (Ic), (Id), (Ie), (If), (Ig), (Ih), (Ik), (Im), (In), (Io), (Ip), (Iq), (Ir), (Is) and (It), methods of synthesizing compounds of Formulae (Ia), (Ib), (Ic), (Id), (Ie), (If), (Ig), (Ih), (Ik), (Im), (In), (Io), (Ip), (Iq), (Ir), (Is) and (It), and methods of using compounds of Formulae (Ia), (Ib), (Ic), (Id), (Ie), (If), (Ig), (Ih), (Ik), (Im), (In), (Io), (Ip), (Iq), (Ir), (Is) and (It) as an analgesic.

23 Claims, 1 Drawing Sheet

(56) References Cited

U.S. PATENT DOCUMENTS

| | | | |
|---|---|---|---|
| 2004/0092531 | A1 | 5/2004 | Chizh et al. |
| 2006/0052370 | A1 | 3/2006 | Meyerson et al. |
| 2007/0082956 | A1 | 4/2007 | Magerl et al. |
| 2007/0254862 | A1 | 11/2007 | Antel et al. |
| 2009/0088418 | A1 | 4/2009 | Pfister et al. |
| 2010/0056553 | A1 | 3/2010 | Plettenburg et al. |
| 2012/0108583 | A1 | 5/2012 | Gharat et al. |
| 2012/0122846 | A1 | 5/2012 | Calderwood et al. |
| 2012/0245137 | A1 | 9/2012 | Pajouhesh et al. |
| 2012/0270893 | A1 | 10/2012 | Dow et al. |
| 2013/0029987 | A1 | 1/2013 | Bennett et al. |
| 2013/0237559 | A1 | 9/2013 | Ortiz et al. |
| 2014/0275245 | A1 | 9/2014 | Bunker |
| 2015/0018328 | A1 | 1/2015 | Konteatis et al. |
| 2015/0246890 | A1 | 9/2015 | Bahmanyar et al. |
| 2015/0297562 | A1 | 10/2015 | Iinuma et al. |
| 2016/0016892 | A1 | 1/2016 | Bunker |
| 2016/0075654 | A1 | 3/2016 | Bunker et al. |
| 2017/0081295 | A1 | 3/2017 | Bunker |

FOREIGN PATENT DOCUMENTS

| | | | |
|---|---|---|---|
| EP | 0372466 | 6/1990 | |
| IL | 54795 A | 10/1980 | |
| JP | 2008-120797 | 5/2008 | |
| WO | WO 2000/056318 | 9/2000 | |
| WO | WO 2001/091736 | 12/2001 | |
| WO | WO 2005/063754 | 7/2005 | |
| WO | WO 2008/096218 | 8/2008 | |
| WO | WO 2009/153720 | 12/2009 | |
| WO | WO 2012/137089 | 10/2012 | |
| WO | WO 2013/024895 | 2/2013 | |
| WO | WO 2013/126856 | 8/2013 | |
| WO | WO 2013/131018 | 9/2013 | |
| WO | WO 2014/065791 | 5/2014 | |
| WO | WO 2014/149819 | 9/2014 | |
| WO | WO 2014/169226 | 10/2014 | |
| WO | WO 2014/206922 | 12/2014 | |
| WO | WO 2015/061247 | 4/2015 | |
| WO | WO 2015/089170 | 6/2015 | |
| WO | WO 2015/134710 | 9/2015 | |
| WO | WO 2015/157127 | 10/2015 | |
| WO | WO 2015/159175 | 10/2015 | |
| WO | WO 2015/162459 | 10/2015 | |
| WO | WO 2016/016370 | 2/2016 | |
| WO | WO-2017193030 A1 * | 11/2017 | ............ A61P 35/00 |

OTHER PUBLICATIONS

Adcock et al., "Transmission of polar substituent effects through the bicyclo [1.1. 1] pentane ring system as monitored by 19F NMR shifts." *Tetrahedron letters* 33.48 (1992): 7397-7398.

Adcock, "A DFT-GIAO and DFT-NBO study of polar substituent effects on NMR 17O chemical shifts in some rigid polycyclic alkanes." *Journal of Physical Organic Chemistry* 24.6 (2011): 492-498.

Adcock et al., "Computation and analysis of 19F substituent chemical shifts of some bridgehead-substituted polycyclic alkyl fluorides." *Magnetic Resonance in Chemistry* 41.7 (2003): 503-508.

Alekseenko, et al., "An Improved Synthesis of 2-, 3-, and 4-(Trifluoromethyl) cyclohexylamines." *Synthesis* 44.17 (2012): 2739-2742.

Applequist et al., "Polar substituent effects in 1,3-disubstituted bicyclo [1.1. 1] pentanes." *The Journal of Organic Chemistry* 47.25 (1982): 4985-4995.

Barone et al., "NMR 3J (C1, H3) couplings in 1-X-bicyclo [1.1. 1] pentanes. FPT-DFT and NBO studies of hyperconjugative interactions and heavy atom substituent effects." *Journal of Computational Chemistry* 22.14 (2001): 1615-1621.

Bunker et al., "Scalable synthesis of 1-bicyclo [1.1. 1] pentylamine via a Hydrohydrazination reaction." *Organic letters* 13.17 (2011): 4746-4748.

Bunz et al., "Brückenkopf-gekoppelte Bicyclo [1.1. 1] pentane: Synthese und Struktur." *Chemische Berichte* 121.10 (1988): 1785-1790.

CAS Reg No. 1219538-83-6, Entered Apr. 19, 2010.
CAS Reg. No. 1046861-73-7, entered STN: Sep. 5, 2008.
CAS Reg. No. 1219538-79-0. Entered STN: Apr. 19, 2010.
CAS Reg. No. 1219538-81-4, Entered STN: Apr. 19, 2010.
CAS Reg. No. 136399-14-9, Entered STN: Sep. 28, 1991.
Cas RN 1230133-71-7, Entered STN: Jul. 11, 2010.
Cas RN 130682-55-2, Entered STN: Nov. 30, 1990.
Cas RN 130974-28-6, Entered STN: Dec. 14, 1990.
Cas RN 136399-14-9, Entered STN: Sep. 28, 1997.

Contreras et al., "Experimental and Theoretical Study of Hyperconjugative Interaction Effects on NMR 1 J CH Scalar Couplings." *The Journal of Physical Chemistry A* 110.12 (2006): 4266-4275.

Contreras et al., "Experimental and DFT studies on the transmission mechanisms of analogous NMR JCH and JCC couplings in 1-X-and 1-X-3-methylbicyclo [1.1. 1]-pentanes." *Magnetic Resonance in Chemistry* 45.7 (2007): 572-577.

Della, et al., "Fluorine-19 chemical shifts in saturated systems." *Australian journal of Chemistry* 23.12 (1970): 2421-2426.

Fluck, E., "New notations in the periodic table." *Pure and Applied Chemistry* 60.3 (1988): 431-436.

Gasper et al., "Cobalt catalyzed functionalization of unactivated alkenes: regioselective reductive C-C bond forming reactions." *Journal of the American Chemical Society* 131.37 (2009): 13214-13215.

Gleiter et al., "The Bicyclo [1.1. 1] pentane Framework—an Excellent Relay for Π/δ Conjugation." *Angewandte Chemie International Edition in English* 29.4 (1990): 413-415.

Gudipati, et al. "Infrared spectra of [n] staffanes." *The Journal of Physical Chemistry* 96.25 (1992): 10165-10176.

Hassner, A. , "Encyclopedia of Reagents for Organic Chemistry," (2005), pp. 1-6, John Wileyand Sons, Ltd. Chichester, UK.

IUPAC Periodic Table of the Elements (2011).

Janecki, T., et al., "[n]Staffanes with Terminal Nitrile and Isonitrile Functionalities and their Metal Complexes" *Collect. Czech. Chem. Commun.* (1993) 83:89-104.

Levin et al., "Bicyclo[1.1.1]pentanes, [n]Staffanes, [1.1. 1]Propellanes, and Tricyclo[2.1.0.0$^{2,5}$]pentanes" (2000) *Chem. Rev.* 100:169-234.

Pätzel et al., "3-Aminobicyclo[1.1.1]pentane-1-carboxylic Acid Derivatives: Synthesis and Incorporation into Peptides" *Eur. J. Org. Chem.* (2004) 2004(3):493-498.

Radchenko, D.S., et al., "Cyclobutane-Derived Diamines: Synthesis and Molecular Structure" Journal of Organic Chemistry (2010) 75:5941-5952.

Toops et al., "Efficient Synthesis of 1 -(Trialkylstannyl)- and 1-(Triarylstannyl)bicyclo[1.1.1]pentanes" *J. Org. Chem.* (1993) 58:6505-6508.

Wang et al., "The Oral Analgesic Efficacy of Bicifadine Hydrochloride in Postoperative Pain" J. Clin. Pharm. (1982) 22(4):160-164.

Waser et al., "Hyrdazines and Azides via the Metal-Catalyzed Hydrohydrazination and Hydroazidation of Olefins" *J. Am. Chem. Soc.* (2006) 128:11693-11712.

Whitney, J.G., et al., "Antiviral agents. I. Bicyclo[2.2.2]octan- and -oct-2-enamines". Journal of Medicinal Chemistry, 1970, vol. 13, No. 2, pp. 254-260.

Wiberg et al., "Reactions of [1.1.1]Propellane" J. Am. Soc. (1990) 112:2194-2216.

Zehnder et al., "Optimization of Potent, Selective, and Orally Bioavailable Pyrrolodinopyrimidine-Containing Inhibitors of Heat Shock Protein 90. Identification of Development Candidate 2-Amino-4{4-chloro-2-[2-(4-fluoro-1H-pyrazol-1-yl)ethoxy]-6-methylphenyl}-N-(2,2-difluoropropyl)-5,7-dihydro-6H-pyrrolo[3,4-d]pyrimidine-6-carboxamide" J. Med. Chem. (2011) 54:3368-3385.

CAS RN 1862496-03-4, STN Entry Date Feb. 9, 2016.
CAS RN 1807920-97-3, STN Entry Date Sep. 22, 2015.

Watari et al., "Pharmacokinetic Study of the Fate of Acetaminophen and Its Conjugates in Rats", Journal of Pharmacokinetics and Biopharmaceutics, vol. 11, No. 3, 1983.

(56) References Cited

OTHER PUBLICATIONS

Hirate, et al.,' First-pass metabolism of acetaminophen in rats after low and high doses, Biopharmaceutics & Drug Disposition, vol. 11, 245-252 (1990).
McPherson, Neuropathic Pain: An Update on Effective Management Strategies' https://www.medscape.org/viewarticle/530606_print. POSTED May 3, 2006.
Süleyman et al., "Anti-inflammatory and side effects of cyclooxygenase inhibitors", Pharmacological Reports, 2007, 59, 247-258.
Benyamin et al., "Opioid Complications and Side Effects" Pain Physician 2008: Opioid Special Issue: 11:S105-S120.
International Search Report and Written Opinion dated Jul. 20, 2018 in PCT/US2018/032417.
International Preliminary Report on Patentability dated Sep. 11, 2019 for PCT Application No. PCT/US2018/032417.

\* cited by examiner

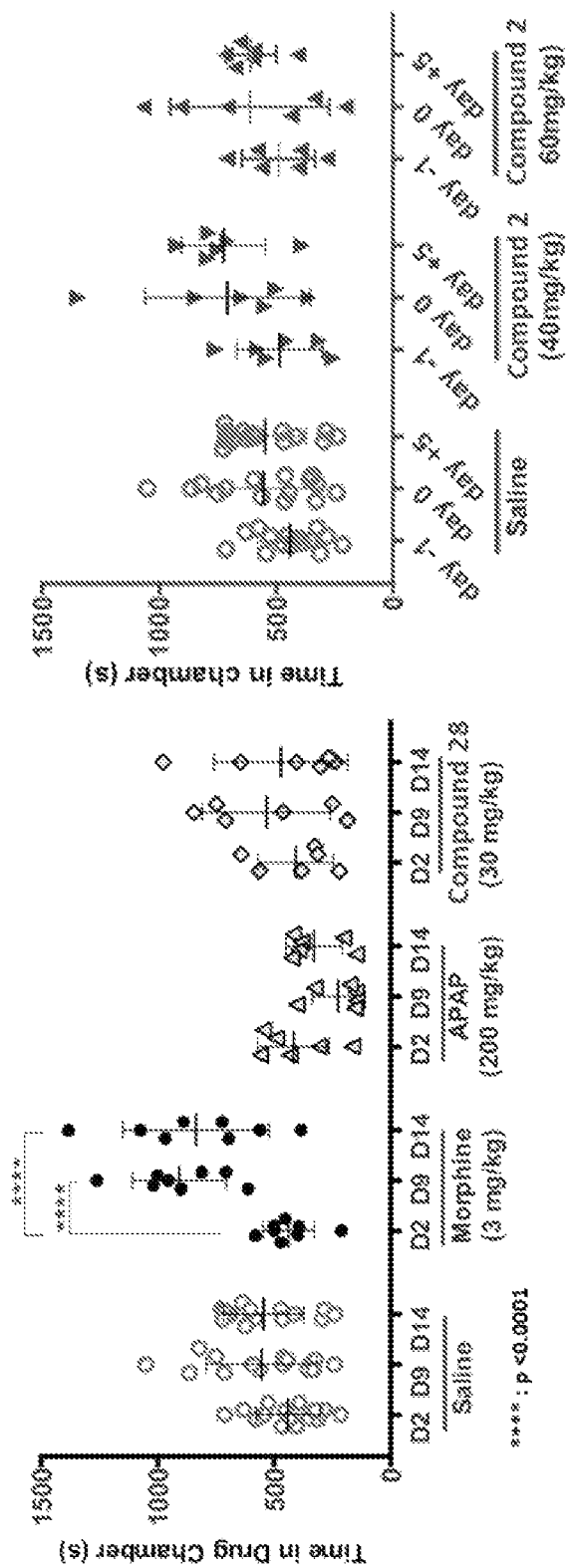

ANALGESIC COMPOUNDS

INCORPORATION BY REFERENCE TO ANY PRIORITY APPLICATIONS

Any and all applications for which a foreign or domestic priority claim is identified, for example, in the Application Data Sheet or Request as filed with the present application, are hereby incorporated by reference under 37 CFR 1.57, and Rules 4.18 and 20.6, such as U.S. Provisional Application No. 62/506,512, filed May 15, 2017 is hereby incorporated by reference in its entirety.

BACKGROUND

Field

The present application relates to the fields of chemistry, biochemistry and medicine. More particularly, disclosed herein are substituted bicyclo[1.1.1]pentyl compounds. Also disclosed herein are methods of using substituted bicyclo[1.1.1]pentyl compounds as an analgesic.

Description

Nonsteroidal anti-inflammatory compounds, or NSAIDs, are an extremely useful group of small molecule drugs, typified by acetylsalicylic acid, ibuprofen and naproxen. Acetaminophen, also known as paracetamol or APAP, is also an effective pain reliever often sold over the counter (without prescription). Opioids is another class of drugs used to treat pain, such as short-term pain. Each of these classes of drugs is associated with one or more undesirable side effects.

SUMMARY

Some embodiments described herein generally relate to a compound selected from Formulae (Ia), (Ib), (Ic), (Id), (Ie), (If), (Ig), (Ih), (Ik), (Im), (In), (Io), (Ip), (Iq), (Ir), (Is) and/or (It), or pharmaceutically acceptable salts of any of the foregoing. Other embodiments described herein generally relate to a pharmaceutical composition that include one or more compounds selected from Formulae (Ia), (Ib), (Ic), (Id), (Ie), (If), (Ig), (Ih), (Ik), (Im), (In), (Io), (Ip), (Iq), (Ir), (Is) and/or (It), or pharmaceutically acceptable salts of any of the foregoing.

Some embodiments described herein generally relate to a method of ameliorating and/or treating pain that can include administering to a subject suffering from pain an effective amount of one or more compounds selected from Formulae (Ia), (Ib), (Ic), (Id), (Ie), (If), (Ig), (Ih), (Ik), (Im), (In), (Io), (Ip), (Iq), (Ir), (Is) and/or (It), or pharmaceutically acceptable salts of any of the foregoing, or a pharmaceutical composition that includes one or more compounds selected from Formulae (Ia), (Ib), (Ic), (Id), (Ie), (If), (Ig), (Ih), (Ik), (Im), (In), (Io), (Ip), (Iq), (Ir), (Is) and/or (It), or pharmaceutically acceptable salts of any of the foregoing. Other embodiments described herein generally relate to using one or more compounds selected from Formulae (Ia), (Ib), (Ic), (Id), (Ie), (If), (Ig), (Ih), (Ik), (Im), (In), (Io), (Ip), (Iq), (Ir), (Is) and/or (It), or pharmaceutically acceptable salts of any of the foregoing, or a pharmaceutical composition that includes one or more compounds selected from Formulae (Ia), (Ib), (Ic), (Id), (Ie), (If), (Ig), (Ih), (Ik), (Im), (In), (Io), (Ip), (Iq), (Ir), (Is) and/or (It), or pharmaceutically acceptable salts of any of the foregoing, in the manufacture of a medicament for ameliorating and/or treating pain. Still other embodiments described herein generally relate to a compound selected from Formulae (Ia), (Ib), (Ic), (Id), (Ie), (If), (Ig), (Ih), (Ik), (Im), (In), (Io), (Ip), (Iq), (Ir), (Is) and/or (It), or pharmaceutically acceptable salts of any of the foregoing, or a pharmaceutical composition that includes one or more compounds selected from Formulae (Ia), (Ib), (Ic), (Id), (Ie), (If), (Ig), (Ih), (Ik), (Im), (In), (Io), (Ip), (Iq), (Ir), (Is) and/or (It), or pharmaceutically acceptable salts of any of the foregoing, that can be used for ameliorating and/or treating pain.

BRIEF DESCRIPTION OF THE DRAWINGS

FIG. 1 graphically depicts the results of a conditioned place preference (CPP) test performed on mice comparing the administration of morphine to some compounds described herein.

DETAILED DESCRIPTION

NSAIDs are often sold without prescription, and are variously used to treat pain, inflammation, and fever. However, NSAIDs can have undesirable side effects, including gastric upset and/or gastric bleeding. Some of these undesirable side effects of NSAIDs are known to be associated with inhibition of the COX-1 and/or COX-2 receptors. (See Suleyman et al. "Anti-inflammatory and side effects of cyclo-oxygenase inhibitors." *Pharmacological reports* 59.3 (2007): 247). Furthermore, both acetaminophen and NSAIDs are known to only be mildly effective in treating neuropathic pain. (See McPherson, "Neuropathic pain: an update on effective management strategies." *American Pharmacists Association* 2006 *Annual Meeting*, 2006).

Acetaminophen shares analgesic and antipyretic properties with NSAIDs. However, APAP has only weak anti-inflammatory properties, and is thus not an NSAID. Unlike many NSAIDs, acetaminophen does not cause gastric upset or bleeding in prescribed doses. Thus, APAP is an extremely useful drug for those wishing analgesia without adverse gastric side effects.

Acetaminophen has the structure:

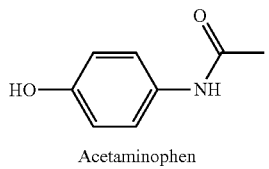

Acetaminophen

Acetaminophen is often combined with other drugs for relief of symptoms of influenza and the common cold, among other indications. It is particularly useful in combination with opioid analgesics, where it exhibits synergistic analgesic properties and allows patients to achieve adequate pain relief with lower doses of opioids. The most widely prescribed drug in the United States is a combination of acetaminophen and hydrocodone, with over 130 million prescriptions in the year 2010. Other acetaminophen-opioid combinations, including combinations with oxycodone, are also widely prescribed.

Acetaminophen poisoning is the most common cause of acute liver failure in the Western world, and acetaminophen accounts for the most drug overdoses in the English-speaking world. Acetaminophen is metabolized to form N-acetyl-p-benzoquinoneimine (NAPQI), which depletes glutathione in the liver, and if the glutathione is sufficiently depleted, as is the case with an acetaminophen overdose, the NAPQI metabolite injures hepatocytes leading to acute liver failure and often death. The acetaminophen-opioid combination drugs are commonly implicated in such toxicity, for various reasons. First, patients might not recognize that the prescribed pain relievers contain acetaminophen, and may supplement with additional acetaminophen if pain relief is inadequate. Second, continued administration of opioids can lead to tolerance and the need for increased dosages to obtain a comparable opioid analgesic effect, and users or abusers of the combination drugs may exceed safe dosages of acetaminophen as a consequence.

This has led the U.S. FDA to seek reduced amounts of acetaminophen in the opioid combination drugs and has also led an FDA advisory panel to recommend banning such drugs all together. Although the acetaminophen-opioid drugs remain on the market, there is a strong need for a less toxic replacement without the same hepatotoxicity risks.

Opioids are generally known to be associated with a number of common side effects and long term negative consequences. Common side effects of opioid administration may include, for example, sedation, dizziness, nausea, vomiting, constipation, physical dependence, tolerance and respiratory depression; and long term negative consequences of opioids may include, for example, psychological addiction and abuse. (See Benyamin, et al. "Opioid Complications and Side Effects" *Pain Physician* 11 (2008): S105-S120). Some of these side effects of opioids are known to be associated with the activation of an opiate receptor, such as opiate receptors $\delta_1$, $\delta_2$, $\kappa$, and/or $\mu$.

With the side effects and dangers associated with NSAIDs, acetaminophen and opioids, there is a desire in the medical community for compounds with comparable or improved analgesic properties that minimize and/or avoid one or more of the undesirable effects associated with NSAIDs, acetaminophen and/or opioids.

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more of the indicated substituents. If no substituents are indicated, it is meant that the indicated "optionally substituted" or "substituted" group may be substituted with one or more group(s) individually and independently selected from deuterium (D), halogen, hydroxy, $C_{1-4}$ alkoxy, $C_{1-8}$ alkyl, $C_{3-20}$ cycloalkyl, aryl, heteroaryl, heterocyclyl, $C_{1-6}$ haloalkyl, cyano, $C_{2-8}$ alkenyl, $C_{2-8}$ alkynyl, $C_{3-20}$ cycloalkenyl, aryl(alkyl), heteroaryl(alkyl), heterocyclyl(alkyl), acyl, thiocarbonyl, O-carbamyl, N-carbamyl, O-thiocarbamyl, N-thiocarbamyl, C-amido, N-amido, C-thioamido, N-thioamido, S-sulfonamido, N-sulfonamido, C-carboxy, O-carboxy, sulfenyl, sulfinyl, sulfonyl, haloalkoxy, an amino, a mono-substituted amine group and a di-substituted amine group.

As used herein, "$C_a$ to $C_b$" in which "a" and "b" are integers refer to the number of carbon atoms in a group. The indicated group can contain from "a" to "b", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "a" and "b" are designated, the broadest range described in these definitions is to be assumed.

If two "R" groups are described as being "taken together" the R groups and the atoms they are attached to can form a cycloalkyl, cycloalkenyl, aryl, heteroaryl or heterocycle. For example, without limitation, if $R^a$ and $R^b$ of an $NR^aR^b$ group are indicated to be "taken together," it means that they are covalently bonded, either indirectly through intermediate atoms, or directly to one another, to form a ring, for example:

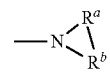

As used herein, the term "alkyl" refers to a fully saturated aliphatic hydrocarbon group. The alkyl moiety may be branched or straight chain. Examples of branched alkyl groups include, but are not limited to, iso-propyl, sec-butyl, t-butyl and the like. Examples of straight chain alkyl groups include, but are not limited to, methyl, ethyl, n-propyl, n-butyl, n-pentyl, n-hexyl, n-heptyl and the like. The alkyl group may have 1 to 30 carbon atoms (whenever it appears herein, a numerical range such as "1 to 30" refers to each integer in the given range; e.g., "1 to 30 carbon atoms" means that the alkyl group may consist of 1 carbon atom, 2 carbon atoms, 3 carbon atoms, etc., up to and including 30 carbon atoms, although the present definition also covers the occurrence of the term "alkyl" where no numerical range is designated). The alkyl group may also be a medium alkyl having 1 to 12 carbon atoms. The alkyl group could also be a lower alkyl having 1 to 6 carbon atoms. An alkyl group may be substituted or unsubstituted.

The term "alkenyl" used herein refers to a monovalent straight or branched chain radical of from two to thirty carbon atoms containing a carbon double bond(s) including, but not limited to, 1-propenyl, 2-propenyl, 2-methyl-1-propenyl, 1-butenyl, 2-butenyl and the like. An alkenyl group may be unsubstituted or substituted.

The term "alkynyl" used herein refers to a monovalent straight or branched chain radical of from two to thirty carbon atoms containing a carbon triple bond(s) including, but not limited to, 1-propynyl, 1-butynyl, 2-butynyl and the like. An alkynyl group may be unsubstituted or substituted.

As used herein, "cycloalkyl" refers to a completely saturated (no double or triple bonds) mono- or multi- cyclic hydrocarbon ring system. When composed of two or more rings, the rings may be joined together in a fused, bridged or spiro fashion. As used herein, the term "fused" refers to two rings which have two atoms and one bond in common.

For example, in the following structure, rings A and B are fused

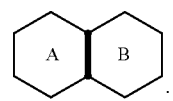

As used herein, the term "bridged cycloalkyl" refers to compounds wherein the cycloalkyl contains a linkage of one or more atoms connecting non-adjacent atoms. The following structures

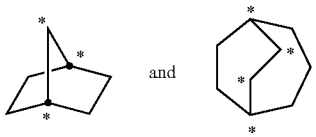 [SMILES: C1C[C@H]2CC[C@H]1C2 ; C1CC2CCC(C1)CC2]

are examples of "bridged" rings. As used herein, the term "spiro" refers to two rings which have one atom in common and the two rings are not linked by a bridge. Cycloalkyl groups can contain 3 to 30 atoms in the ring(s), 3 to 20 atoms in the ring(s), 3 to 10 atoms in the ring(s), 3 to 8 atoms in the ring(s) or 3 to 6 atoms in the ring(s). A cycloalkyl group may be unsubstituted or substituted. Examples of monocycloalkyl groups include, but are in no way limited to, cyclopropyl, cyclobutyl, cyclopentyl, cyclohexyl, cycloheptyl and cyclooctyl. Examples of fused cycloalkyl groups are decahydronaphthalenyl, dodecahydro-1H-phenalenyl and tetradecahydroanthracenyl; examples of bridged cycloalkyl groups are bicyclo[1.1.1]pentyl, adamantanyl, and norbornanyl; and examples of spiro cycloalkyl groups include spiro[3.3]heptane and spiro[4.5]decane.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). Cycloalkenyl groups can contain 3 to 30 atoms in the ring(s), 3 to 20 atoms in the ring(s), 3 to 10 atoms in the ring(s), 3 to 8 atoms in the ring(s) or 3 to 6 atoms in the ring(s). When composed of two or more rings, the rings may be connected together in a fused, bridged or spiro fashion. A cycloalkenyl group may be unsubstituted or substituted.

As used herein, "cycloalkynyl" refers to a mono- or multi-cyclic hydrocarbon ring system that contains one or more triple bonds in at least one ring. If there is more than one triple bond, the triple bonds cannot form a fully delocalized pi-electron system throughout all the rings. Cycloalkynyl groups can contain 8 to 30 atoms in the ring(s), 8 to 20 atoms in the ring(s) or 8 to 10 atoms in the ring(s). When composed of two or more rings, the rings may be joined together in a fused, bridged or spiro fashion. A cycloalkynyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a monocyclic or multicyclic aromatic ring system (a ring system with fully delocalized pi-electron system) that contain(s) one or more heteroatoms (for example, 1, 2 or 3 heteroatoms), that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" or "heteroalicyclyl" refers to three-, four-, five-, six-, seven-, eight-, nine-, ten-, up to 18-membered monocyclic, bicyclic and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatom(s) is an element other than carbon including, but not limited to, oxygen, sulfur and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused or spiro fashion. Additionally, any nitrogens in a heteroalicyclic may be quaternized. Heterocyclyl or heteroalicyclic groups may be unsubstituted or substituted. Examples of such "heterocyclyl" or "heteroalicyclyl" groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone and their benzo-fused analogs (e.g., benzimidazolidinone, tetrahydroquinoline and/or 3,4-methylenedioxyphenyl).

As used herein, "aralkyl" and "aryl(alkyl)" refer to an aryl group connected, as a substituent, via a lower alkylene group. The lower alkylene and aryl group of an aralkyl may be substituted or unsubstituted. Examples include but are not limited to benzyl, 2-phenylalkyl, 3-phenylalkyl and naphthylalkyl.

As used herein, "heteroaralkyl" and "heteroaryl(alkyl)" refer to a heteroaryl group connected, as a substituent, via a lower alkylene group. The lower alkylene and heteroaryl group of heteroaralkyl may be substituted or unsubstituted. Examples include but are not limited to 2-thienylalkyl, 3-thienylalkyl, furylalkyl, thienylalkyl, pyrrolylalkyl, pyridylalkyl, isoxazolylalkyl and imidazolylalkyl and their benzo-fused analogs.

A "heteroalicyclyl(alkyl)" and "heterocyclyl(alkyl)" refer to a heterocyclic or a heteroalicyclylic group connected, as a substituent, via a lower alkylene group. The lower alkylene and heterocyclyl of a (heteroalicyclyl)alkyl may be substituted or unsubstituted. Examples include but are not limited tetrahydro-2H-pyran-4-yl(methyl), piperidin-4-yl(ethyl), piperidin-4-yl(propyl), tetrahydro-2H-thiopyran-4-yl (methyl) and 1,3-thiazinan-4-yl(methyl).

"Lower alkylene groups" are straight-chained —CH$_2$— tethering groups, forming bonds to connect molecular fragments via their terminal carbon atoms. Examples include but are not limited to methylene (—CH$_2$—), ethylene (—CH$_2$CH$_2$—), propylene (—CH$_2$CH$_2$CH$_2$—) and butylene (—CH$_2$CH$_2$CH$_2$CH$_2$—). A lower alkylene group can be substituted by replacing one or more hydrogen of the lower alkylene group and/or by substituting both hydrogens on the same carbon with a cycloalkyl group

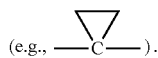

As used herein, the term "hydroxy" refers to a —OH group.

As used herein, "alkoxy" refers to the formula —OR wherein R is an alkyl, an alkenyl, an alkynyl, a cycloalkyl, a cycloalkenyl, aryl, heteroaryl, heterocyclyl, cycloalkyl (alkyl), aryl(alkyl), heteroaryl(alkyl) or heterocyclyl(alkyl) is defined herein. A non-limiting list of alkoxys is methoxy, ethoxy, n-propoxy, 1-methylethoxy (isopropoxy), n-butoxy, iso-butoxy, sec-butoxy, tert-butoxy, phenoxy and benzoxy. An alkoxy may be substituted or unsubstituted.

As used herein, "acyl" refers to a hydrogen, alkyl, alkenyl, alkynyl, aryl, heteroaryl, heterocyclyl, aryl(alkyl), heteroaryl(alkyl) and heterocyclyl(alkyl) connected, as substituents, via a carbonyl group. Examples include formyl, acetyl, propanoyl, benzoyl and acryl. An acyl may be substituted or unsubstituted.

A "cyano" group refers to a "—CN" group.

The term "halogen atom" or "halogen" as used herein, means any one of the radio-stable atoms of column 7 of the Periodic Table of the Elements, such as, fluorine, chlorine, bromine and iodine.

A "thiocarbonyl" group refers to a "—C(=S)R" group in which R can be the same as defined with respect to O-carboxy. A thiocarbonyl may be substituted or unsubstituted.

An "O-carbamyl" group refers to a "—OC(=O)N (R$_A$R$_B$)" group in which RA and R$_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An O-carbamyl may be substituted or unsubstituted.

An "N-carbamyl" group refers to an "ROC(=O)N (R$_A$)—" group in which R and R$_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-carbamyl may be substituted or unsubstituted.

An "O-thiocarbamyl" group refers to a "—OC(=S)—N (R$_A$R$_B$)" group in which R$_A$ and R$_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An O-thiocarbamyl may be substituted or unsubstituted.

An "N-thiocarbamyl" group refers to an "ROC(=S)N (R$_A$)—" group in which R and R$_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-thiocarbamyl may be substituted or unsubstituted.

A "C-amido" group refers to a "—C(=O)N(R$_A$R$_B$)" group in which R$_A$ and R$_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). A C-amido may be substituted or unsubstituted.

An "N-amido" group refers to a "RC(=O)N(R$_A$)—" group in which R and R$_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-amido may be substituted or unsubstituted.

A "C-thioamido" group refers to a "—C(=S)N(R$_A$R$_B$)" group in which R$_A$ and R$_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). A C-thioamido may be substituted or unsubstituted.

An "N-thioamido" group refers to a "RC(=S)N(R$_A$)—" group in which R and R$_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-thioamido may be substituted or unsubstituted.

An "S-sulfonamido" group refers to a "—SO$_2$N(R$_A$R$_B$)" group in which R$_A$ and R$_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An S-sulfonamido may be substituted or unsubstituted.

An "N-sulfonamido" group refers to a "RSO$_2$N(R$_A$)—" group in which R and R$_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-sulfonamido may be substituted or unsubstituted.

An "O-carboxy" group refers to a "RC(=O)O—" group in which R can be hydrogen, an alkyl, an alkenyl, an alkynyl, an alkoxy, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein. An O-carboxy may be substituted or unsubstituted.

The terms "ester" and "C-carboxy" refer to a "—C(=O) OR" group in which R can be the same as defined with respect to O-carboxy. An ester and C-carboxy may be substituted or unsubstituted.

A "sulfenyl" group refers to an "-SR" group in which R can be hydrogen, an alkyl, an alkenyl, an alkynyl, a cycloalkyl, a cycloalkenyl, aryl, heteroaryl, heterocyclyl, cycloalkyl (alkyl), aryl(alkyl), heteroaryl(alkyl) or heterocyclyl(alkyl). A sulfenyl may be substituted or unsubstituted.

A "sulfinyl" group refers to an "—S(=O)—R" group in which R can be the same as defined with respect to sulfenyl. A sulfinyl may be substituted or unsubstituted.

A "sulfonyl" group refers to an "SO$_2$R" group in which R can be the same as defined with respect to sulfenyl. A sulfonyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl, 1-chloro-2-fluoromethyl and 2-fluoroisobutyl. A haloalkyl may be substituted or unsubstituted.

As used herein, "haloalkoxy" refers to an alkoxy group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy, 1-chloro-2-fluoromethoxy and 2-fluoroisobutoxy. A haloalkoxy may be substituted or unsubstituted.

The term "amino" as used herein refers to a —NH$_2$ group.

A "mono-substituted amine" group refers to a "—NHR" group in which R can be an alkyl, an alkenyl, an alkynyl, a haloalkyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein. A mono-substituted amino may be substituted or unsubstituted. Examples of mono-substituted amino groups include, but are not limited to, —NH(methyl), —NH(phenyl) and the like.

A "di-substituted amine" group refers to a "—NR$_A$R$_B$" group in which RA and R$_B$ can be independently an alkyl, an alkenyl, an alkynyl, a haloalkyl, a cycloalkyl, a cycloalkenyl, aryl, heteroaryl, heterocyclyl, cycloalkyl(alkyl), aryl (alkyl), heteroaryl(alkyl) or heterocyclyl(alkyl), as defined herein. A di-substituted amino may be substituted or unsubstituted. Examples of di-substituted amino groups include, but are not limited to, —N(methyl)$_2$, —N(phenyl)(methyl), —N(ethyl)(methyl) and the like.

As used herein, the term "amino acid" refers to α-amino acids. Examples of suitable α-amino acids include, but are not limited to, alanine, asparagine, aspartic acid, cysteine, glutamic acid, glutamine, glycine, proline, serine, selenocysteine, tyrosine, arginine, histidine, isoleucine, leucine, lysine, methionine, phenylalanine, threonine, tryptophan and valine. Additional examples of suitable amino acids include, but are not limited to, ornithine, hypusine, 2-aminoisobutyric acid, dehydroalanine, citrulline, alpha-ethyl-glycine, alpha-propyl-glycine and norleucine.

Where the numbers of substituents is not specified (e.g. haloalkyl), there may be one or more substituents present. For example, "haloalkyl" may include one or more of the same or different halogens. As another example, "C$_1$-C$_3$ alkoxyphenyl" may include one or more of the same or different alkoxy groups containing one, two or three atoms.

As used herein, a radical indicates species with a single, unpaired electron such that the species containing the radical can be covalently bonded to another species. Hence, in this context, a radical is not necessarily a free radical. Rather, a radical indicates a specific portion of a larger molecule. The term "radical" can be used interchangeably with the term "group."

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), a sulfuric acid, a nitric acid and a phosphoric acid (such as 2,3-dihydroxypropyl dihydrogen phosphate). Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluenesulfonic, trifluoroacetic, benzoic, salicylic, 2-oxopentanedioic, or naphthalenesulfonic acid. Pharmaceutical salts can also be obtained by reacting a compound with a base to form a salt such as an ammonium salt, an alkali metal salt, such as a sodium, a potassium or a lithium salt, an alkaline earth metal salt, such as a calcium or a magnesium salt, a salt of a carbonate, a salt of a bicarbonate, a salt of organic bases such as dicyclohexylamine, N-methyl-D-glucamine, tris(hydroxymethyl)methylamine, C$_1$-C$_7$ alkylamine, cyclohexylamine, triethanolamine, ethylenediamine, and salts with amino acids such as arginine and lysine. For compounds of Formulae (Ia), (Ib), (Ic), (Id), (Ie), (If), (Ig), (Ih), (Ik), (Im), (In), (Io), (Ip), (Iq), (Ir), (Is) and/or (It), those skilled in the art understand that when a salt is formed by protonation of a nitrogen-based group (for example, NH$_2$), the nitrogen-based group can be associated with a positive charge (for example, NH$_2$ can become NH$_3^+$) and the positive charge can be balanced by a negatively charged counterion (such as Cl$^-$).

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition, it is understood that in any compound described herein having one or more double bond(s) generating geometrical isomers that can be defined as E or Z, each double bond may independently be E or Z, or a mixture thereof.

In some embodiments, in any compound described, all tautomeric forms are also intended to be included. For example, without limitation, a reference to the compound

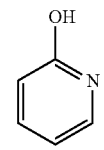

may be interpreted to include tautomer

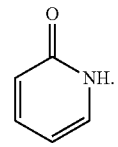

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

It is understood that the methods and combinations described herein include crystalline forms (also known as polymorphs, which include the different crystal packing arrangements of the same elemental composition of a compound), amorphous phases, salts, solvates, and hydrates. In some embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

Where a range of values is provided, it is understood that the upper and lower limit, and each intervening value between the upper and lower limit of the range is encompassed within the embodiments.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' including but not limited to,' or the like; the term 'comprising' as used herein is synonymous with 'including,' containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; and use of terms like 'preferably,' 'preferred,' 'desired,' or 'desirable,' and words of similar meaning should not be understood as implying that certain features are critical, essential, or even important to the structure or function, but instead as merely intended to highlight alternative or additional features that may or cannot be utilized in a particular embodiment. In addition, the term "comprising" is to be interpreted synonymously with the phrases "having at least" or "including at least". When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

Compounds

Some embodiments described herein generally relate to a compound, or a pharmaceutically acceptable salt thereof, selected from:

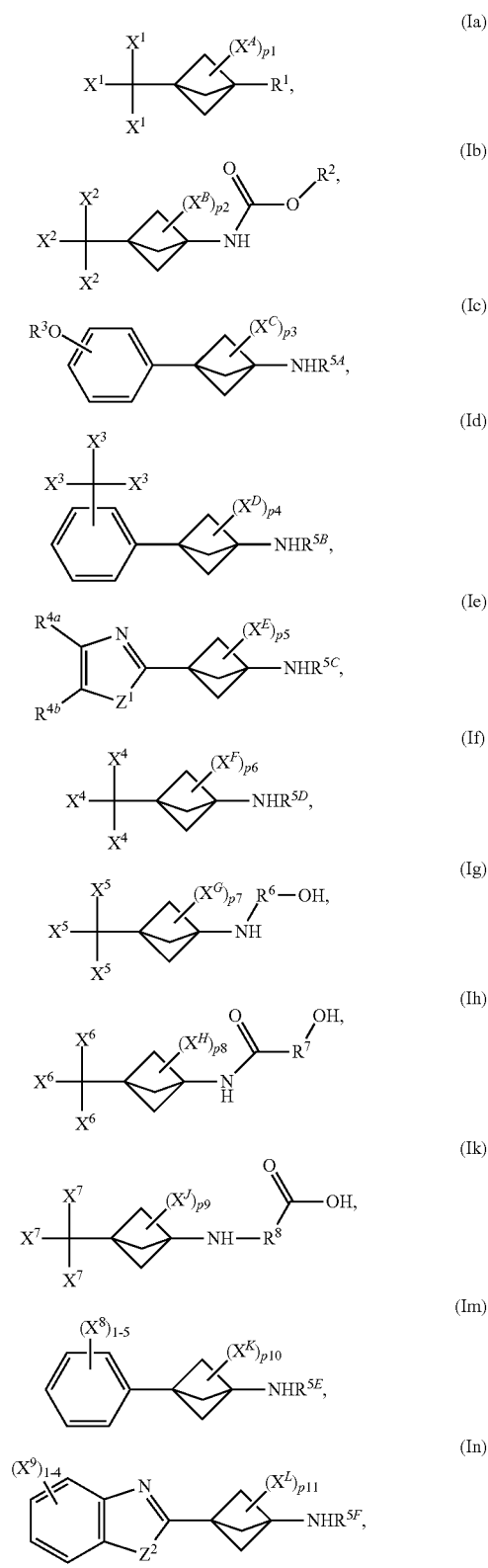

-continued

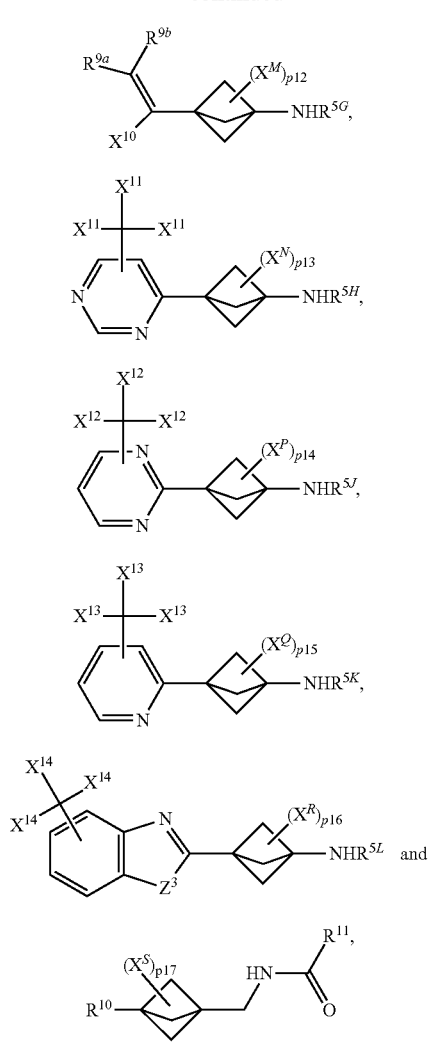

wherein: each $X^1$, each $X^2$, each $X^3$, each $X^4$, each $X^5$, each $X^6$, each $X^7$, each $X^{11}$, each $X^{12}$, each $X^{13}$ and each $X^{14}$ can be independently hydrogen, deuterium, an unsubstituted $C_{1-4}$ alkyl, fluoro or chloro, provided that at least two of $X^1$ is fluoro or chloro, provided that at least two of $X^2$ is fluoro or chloro, provided that at least two of $X^3$ is fluoro or chloro, provided that at least two of $X^4$ is fluoro or chloro, provided that at least two of $X^5$ is fluoro or chloro, provided that at least two of $X^6$ is fluoro or chloro, provided that at least two of $X^7$ is fluoro or chloro, provided that at least two of $X^{11}$ is fluoro or chloro, provided that at least two of $X^{12}$ is fluoro or chloro, provided that at least two of $X^{13}$ is fluoro or chloro, and provided that at least two of $X^{14}$ is fluoro or chloro; each $X^8$, each $X^9$ and $X^{10}$ can be independently deuterium, fluoro or chloro; $R^1$ can be an unsubstituted α-amino acid; $R^2$ and $R^3$ can be independently an unsubstituted $C_{1-4}$ alkyl; $R^{9a}$ and $R^{9b}$ can be independently an unsubstituted $C_{1-4}$ alkyl; $R^{5A}$, $R^{5B}$, $R^{5D}$, $R^{5E}$, $R^{5F}$, $R^{5G}$, $R^{5H}$, $R^{5J}$, $R^{6K}$ and $R^{5L}$ can be independently hydrogen, deuterium or an unsubstituted $C_{1-4}$ alkyl; $R^{5C}$ can be selected from hydrogen, deuterium, an unsubstituted $C_{1-4}$ alkyl and $C(=O)R^{12}$; $R^{4a}$ and $R^{4b}$ can be independently hydrogen, deuterium, an unsubstituted $C_{1-4}$ alkyl, a hydroxy substituted $C_{1-4}$ alkyl or $-C(X^{16})_3$, provided that at least one of $R^{4a}$ and $R^{4b}$ is $-C(X^{16})_3$; $R^6$, $R^7$ and $R^8$ can be independently $-(CH_2)_m$; $R^{10}$ can be selected from hydrogen, deuterium, halogen, hydroxy, an unsubstituted $C_{1-8}$ alkyl, an unsubstituted $C_{3-20}$ cycloalkyl and an unsubstituted $C_{1-8}$ haloalkyl; $R^{11}$ can be selected from hydrogen, deuterium, halogen, an unsubstituted $C_{1-30}$ alkyl, an unsubstituted $C_{2-30}$ alkenyl and an unsubstituted $C_{1-8}$ haloalkyl; $R^{12}$ can be selected from of hydrogen, deuterium, an unsubstituted $C_{1-30}$ alkyl and an unsubstituted $C_{2-30}$ alkenyl; each $X^{16}$ can be independently hydrogen, deuterium, an unsubstituted $C_{1-4}$ alkyl, fluoro or chloro, provided that at least two of $X^{16}$ is fluoro or chloro; $Z^1$, $Z^2$ and $Z^3$ can be independently nitrogen, oxygen or sulfur; m can be 1, 2, 3 or 4; each $X^A$, each $X^B$, each $X^C$, each $X^D$, each $X^E$, each $X^F$, each $X^G$, each $X^I$, each $X^J$, each $X^K$, each $X^L$, each $X^M$, each $X^N$, each $X^P$, each $X^Q$, each $X^R$ and each $X^S$ can be independently deuterium, chloro or fluoro; p1, p2, p3, p4, p5, p6, p7, p8, p9, p10, p11, p12, p13, p14, p15 and p16 can be independently 0, 1, 2, 3, 4, 5 or 6; and p17 can be 1, 2, 3, 4, 5 or 6.

Formula (Ia)

In some embodiments, the compound, or pharmaceutically acceptable salt thereof, can be a compound of Formula (Ia), or pharmaceutically acceptable salt thereof, having the structure:

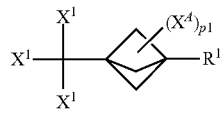

(Ia)

In some embodiments of Formula (Ia), each $X^1$ can be independently hydrogen, deuterium, an unsubstituted $C_{1-4}$ alkyl, fluoro or chloro, provided that at least two of $X^1$ is fluoro or chloro; $R^1$ can be an unsubstituted α-amino acid; each $X^A$ can be independently deuterium, chloro or fluoro; and p1 can be independently 0, 1, 2, 3, 4, 5 or 6.

In some embodiments of Formula (Ia), each $X^1$ can be fluoro. In some embodiments, each $X^1$ can be chloro. In some embodiments, two of $X^1$ can be fluoro, and one of $X^1$ can be chloro. In some embodiments, two of $X^1$ can be chloro, and one of $X^1$ can be fluoro. In some embodiments, two of $X^1$ can be fluoro, and one of $X^1$ can be hydrogen. In some embodiments, two of $X^1$ can be fluoro, and one of $X^1$ can be deuterium. In some embodiments, two of $X^1$ can be fluoro, and one of $X^1$ can be an unsubstituted $C_{1-4}$ alkyl. Examples of $C_{1-4}$ alkyl groups include methyl, ethyl, n-propyl, iso-propyl, n-butyl, iso-butyl and tert-butyl. In some embodiments, two of $X^1$ can be chloro, and one of $X^1$ can be hydrogen. In some embodiments, two of $X^1$ can be chloro, and one of $X^1$ can be deuterium. In some embodiments, two of $X^1$ can be chloro, and one of $X^1$ can be an unsubstituted $C_{1-4}$ alkyl. Examples of $C_{1-4}$ alkyl groups include methyl, ethyl, n-propyl, iso-propyl, n-butyl, iso-butyl and tert-butyl.

In some embodiments of Formula (Ia), $R^1$ can be an unsubstituted α-amino acid. Examples of unsubstituted α-amino acids are provided herein. In some embodiments, $R^1$ can be selected from alanine, asparagine, aspartic acid, cysteine, glutamic acid, glutamine, glycine, proline, serine, selenocysteine, tyrosine, arginine, histidine, isoleucine, leucine, lysine, methionine, phenylalanine, threonine, tryptophan and valine. When $R^1$ is an unsubstituted α-amino acid, the carboxylic acid portion of the unsubstituted α-amino acid can be transformed to a —NH group such that the unsubstituted α-amino acid is attached to the bicyclo[1.1.1]pentyl ring via the —NH group. For example, when R¹ is valine, R¹ has the structure
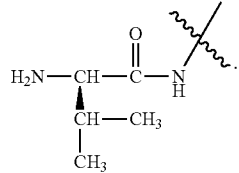
Other examples of unsubstituted α-amino acids wherein the carboxylic acid portion of the unsubstituted α-amino acid is transformed to a —NH group include, but are not limited to, the following:
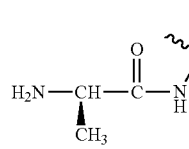 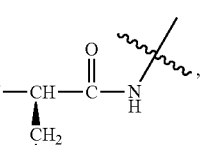
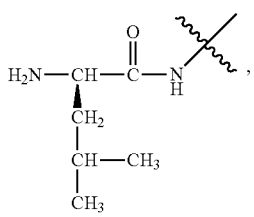
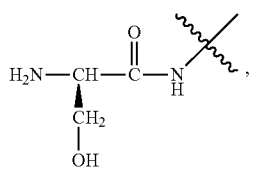
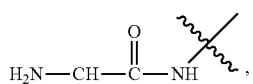
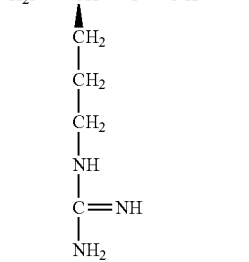
-continued
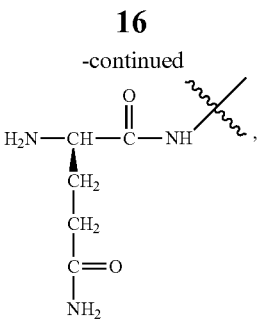
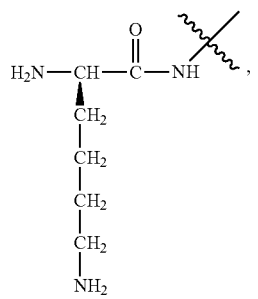
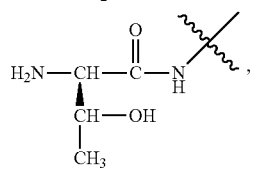
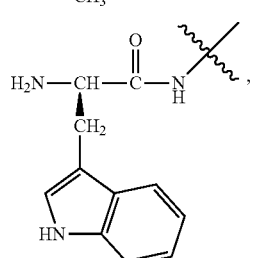
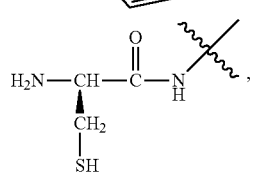
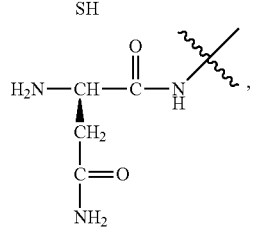
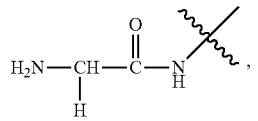
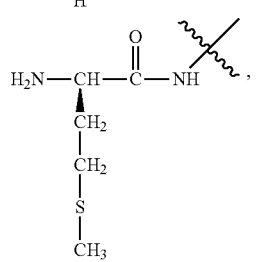

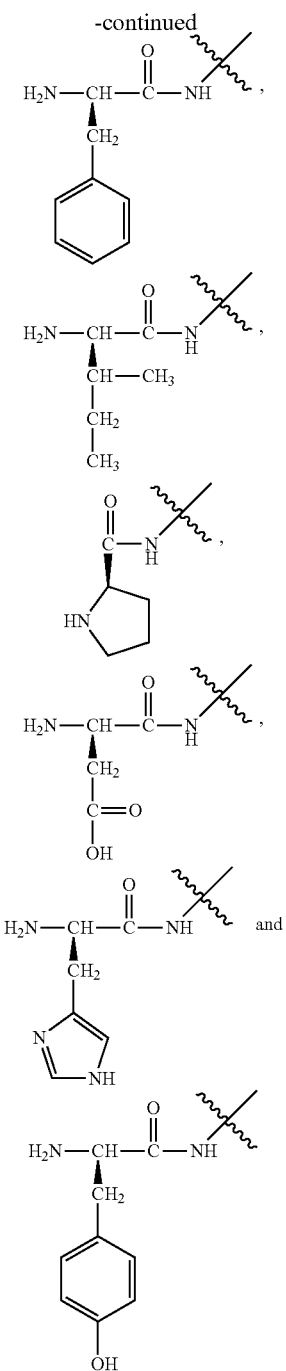

In some embodiments, $R^1$ can be $H_2N$—$CH(R'')$—$C$(=O)—NH—, wherein R" is a side chain of an α-amino acid. Alpha-amino acids are known to those skilled in the art and include but are not limited to, alanine, asparagine, aspartic acid, cysteine, glutamic acid, glutamine, glycine, proline, serine, selenocysteine, tyrosine, arginine, histidine, isoleucine, leucine, lysine, methionine, phenylalanine, threonine, tryptophan, valine, ornithine, hypusine, 2-aminoisobutyric acid, dehydroalanine, citrulline, alpha-ethylglycine, alpha-propyl-glycine and norleucine.

In some embodiments of Formula (Ia), p1 can be 0. In other embodiments, each $X^A$ can be deuterium, and p1 can be 6. In still other embodiments, each $X^A$ can be deuterium, and p1 can be 5. In yet still other embodiments, each $X^A$ can be deuterium, and p1 can be 4. In some embodiments, each $X^A$ can be deuterium, and p1 can be 3. In other embodiments, each $X^A$ can be deuterium, and p1 can be 2. In still other embodiments, each $X^A$ can be deuterium, and p1 can be 1. In some embodiments, each $X^A$ can be chloro, and p1 can be 6. In other embodiments, each $X^A$ can be chloro, and p1 can be 5. In still other embodiments, each $X^A$ can be chloro, and p1 can be 4. In yet still other embodiments, each $X^A$ can be chloro, and p1 can be 3. In some embodiments, each $X^A$ can be chloro, and p1 can be 2. In other embodiments, each $X^A$ can be chloro, and p1 can be 1. In some embodiments, each $X^A$ can be fluoro, and p1 can be 6. In other embodiments, each $X^A$ can be fluoro, and p1 can be 5. In still other embodiments, each $X^A$ can be fluoro, and p1 can be 4. In yet still other embodiments, each $X^A$ can be fluoro, and p 1 can be 3. In some embodiments, each $X^A$ can be fluoro, and p1 can be 2. In other embodiments, each $X^A$ can be fluoro, and p1 can be 1.

Formula (Ib)

In some embodiments, the compound, or pharmaceutically acceptable salt thereof, can be a compound of Formula (Ib), or pharmaceutically acceptable salt thereof, having the structure:

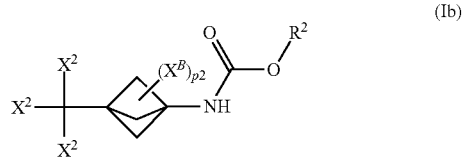

In some embodiments of Formula (Ib), each $X^2$ can be independently hydrogen, deuterium, an unsubstituted $C_{1-4}$ alkyl, fluoro or chloro, provided that at least two of $X^2$ is fluoro or chloro; $R^2$ can be an unsubstituted $C_{1-4}$ alkyl; each $X^B$ can be independently deuterium, chloro or fluoro; and p2 can be independently 0, 1, 2, 3, 4, 5 or 6.

In some embodiments of Formula (Ib), each $X^2$ can be fluoro. In some embodiments, each $X^2$ can be chloro. In some embodiments, two of $X^2$ can be fluoro, and one of $X^2$ can be chloro. In some embodiments, two of $X^2$ can be chloro, and one of $X^2$ can be fluoro. In some embodiments, two of $X^2$ can be fluoro, and one of $X^2$ can be hydrogen. In some embodiments, two of $X^2$ can be fluoro, and one of $X^2$ can be deuterium. In some embodiments, two of $X^2$ can be fluoro, and one of $X^2$ can be an unsubstituted $C_{1-4}$ alkyl. In some embodiments, two of $X^2$ can be chloro, and one of $X^2$ can be hydrogen. In some embodiments, two of $X^2$ can be chloro, and one of $X^2$ can be deuterium. In some embodiments, two of $X^2$ can be chloro, and one of $X^2$ can be an unsubstituted $C_{1-4}$ alkyl. Examples of $C_{1-4}$ alkyl groups include methyl, ethyl, n-propyl, iso-propyl, n-butyl, iso-butyl and tert-butyl.

In some embodiments of Formula (Ib), $R^2$ can be methyl. In other embodiments, $R^2$ can be ethyl. In still other embodiments, $R^2$ can be propyl, such as n-propyl or iso-propyl. In yet still other embodiments, $R^2$ can be butyl, for example, n-butyl, iso-butyl or tert-butyl.

In some embodiments of Formula (Ib), p2 can be 0. In other embodiments, each $X^B$ can be deuterium, and p2 can be 6. In still other embodiments, each $X^B$ can be deuterium, and p2 can be 5. In yet still other embodiments, each $X^B$ can be deuterium, and p2 can be 4. In some embodiments, each $X^B$ can be deuterium, and p2 can be 3. In other embodiments, each $X^B$ can be deuterium, and p2 can be 2. In still other embodiments, each $X^B$ can be deuterium, and p2 can be 1. In some embodiments, each $X^B$ can be chloro, and p2 can be 6. In other embodiments, each $X^B$ can be chloro, and p2 can be 5. In still other embodiments, each $X^B$ can be chloro, and p2 can be 4. In yet still other embodiments, each $X^B$ can be chloro, and p2 can be 3. In some embodiments, each $X^B$ can be chloro, and p2 can be 2. In other embodiments, each $X^B$ can be chloro, and p2 can be 1. In some embodiments, each $X^B$ can be fluoro, and p2 can be 6. In other embodiments, each $X^B$ can be fluoro, and p2 can be 5. In still other embodiments, each $X^B$ can be fluoro, and p2 can be 4. In yet still other embodiments, each $X^B$ can be fluoro, and p2 can be 3. In some embodiments, each $X^B$ can be fluoro, and p2 can be 2. In other embodiments, each $X^B$ can be fluoro, and p2 can be 1.

In some embodiments of Formula (Ib), when at least two of $X^2$ are halogen, such as fluoro and chloro, then $R^2$ cannot be an unsubstituted $C_{1-4}$ alkyl. In other embodiments, when at least two of $X^2$ are halogen, such as fluoro and chloro, and p2 is 0, then $R^2$ cannot be an unsubstituted $C_{1-4}$ alkyl. In still other embodiments, when at least two of $X^2$ are fluoro and p2 is 0, then $R^2$ cannot be an unsubstituted $C_{1-4}$ alkyl. In some embodiments, when one of $X^2$ is an unsubstituted $C_{1-4}$ alkyl, then $R^2$ cannot be an unsubstituted $C_{1-4}$ alkyl. In other embodiments, when one of $X^2$ is an unsubstituted $C_{1-4}$ alkyl and p2 is 0, then $R^2$ cannot be an unsubstituted $C_{1-4}$ alkyl. In still other embodiments, when one of $X^2$ is methyl and p2 is 0, then $R^2$ cannot be an unsubstituted $C_{1-4}$ alkyl. In some embodiments, when p2 is 0, then each of $X^2$ cannot be halogen, such as fluoro and chloro. In still other embodiments, when p2 is 0, then two of $X^2$ cannot be fluoro. In yet still other embodiments, when p2 is 0, then —$C(X^2)_3$ cannot be —$CF_3$. In some embodiments, when p2 is 0, then $R^2$ cannot be an unsubstituted $C_{1-4}$ alkyl. In other embodiments, when p2 is 0, then $R^2$ cannot be an unsubstituted $C_4$ alkyl. In some embodiments, when two of $X^2$ are fluoro, one of $X^2$ is methyl and p2 is 0, then $R^2$ cannot be an unsubstituted $C_4$ alkyl. In other embodiments, when three of $X^2$ is fluoro and p2 is 0, then $R^2$ cannot be an unsubstituted $C_4$ alkyl. In some embodiments, p2 cannot be 0. Examples of $C_{1-4}$ alkyl groups include methyl, ethyl, n-propyl, iso-propyl, n-butyl, iso-butyl and tert-butyl. Examples of $C_4$ alkyl groups include n-butyl, iso-butyl and tert-butyl. In still other embodiments, a compound of Formula (Ib), or a pharmaceutically acceptable salt thereof, cannot one or more of the following compounds,

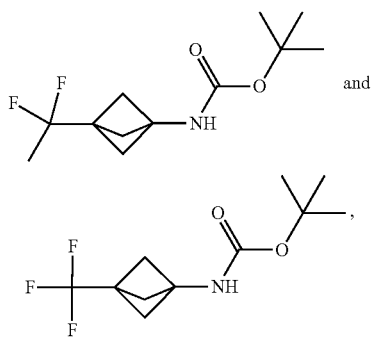

or a pharmaceutically acceptable salt of any of the foregoing.

Formula (Ic)

In some embodiments, the compound, or pharmaceutically acceptable salt thereof, can be a compound of Formula (Ic), or pharmaceutically acceptable salt thereof, having the structure:

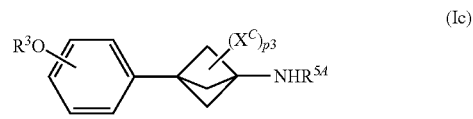

(Ic)

In some embodiments of Formula (Ic), $R^3$ can be an unsubstituted $C_{1-4}$ alkyl; $R^{5A}$ can be independently hydrogen, deuterium or an unsubstituted $C_{1-4}$ alkyl; each $X^C$ can be independently deuterium, chloro or fluoro; and p3 can be independently 0, 1, 2, 3, 4, 5 or 6.

In some embodiments of Formula (Ic), $R^3$ can be methyl. In other embodiments, $R^3$ can be ethyl. In still other embodiments, $R^3$ can be propyl, such as n-propyl or iso-propyl. In yet still other embodiments, $R^3$ can be butyl, for example, n-butyl, iso-butyl or tert-butyl.

In some embodiments of Formula (Ic), $R^{5A}$ can be hydrogen. In other embodiments, $R^{5A}$ can be deuterium. In still other embodiments, $R^{5A}$ can be an unsubstituted $C_{1-4}$ alkyl. Examples of $C_{1-4}$ alkyl groups include methyl, ethyl, n-propyl, iso-propyl, n-butyl, iso-butyl and tert-butyl.

In some embodiments of Formula (Ic), p3 can be 0. In other embodiments, each $X^C$ can be deuterium, and p3 can be 6. In still other embodiments, each $X^C$ can be deuterium, and p3 can be 5. In yet still other embodiments, each $X^C$ can be deuterium, and p3 can be 4. In some embodiments, each $X^C$ can be deuterium, and p3 can be 3. In other embodiments, each $X^C$ can be deuterium, and p3 can be 2. In still other embodiments, each $X^C$ can be deuterium, and p3 can be 1. In some embodiments, each $X^C$ can be chloro, and p3 can be 6. In other embodiments, each $X^C$ can be chloro, and p3 can be 5. In still other embodiments, each $X^C$ can be chloro, and p3 can be 4. In yet still other embodiments, each $X^C$ can be chloro, and p3 can be 3. In some embodiments, each $X^C$ can be chloro, and p3 can be 2. In other embodiments, each $X^C$ can be chloro, and p3 can be 1. In some embodiments, each $X^C$ can be fluoro, and p3 can be 6. In other embodiments, each $X^C$ can be fluoro, and p3 can be 5. In still other embodiments, each $X^C$ can be fluoro, and p3 can be 4. In yet still other embodiments, each $X^C$ can be fluoro, and p3 can be 3. In some embodiments, each $X^C$ can be fluoro, and p3 can be 2. In other embodiments, each $X^C$ can be fluoro, and p3 can be 1.

Formula (Id)

In some embodiments, the compound, or pharmaceutically acceptable salt thereof, can be a compound of Formula (Id), or pharmaceutically acceptable salt thereof, having the structure:

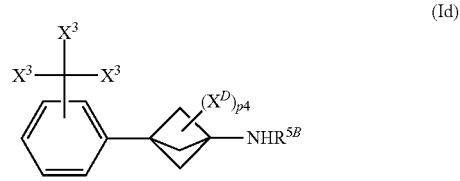

(Id)

In some embodiments of Formula (Id), each $X^3$ can be independently hydrogen, deuterium, an unsubstituted $C_{1-4}$ alkyl, fluoro or chloro, provided that at least two of $X^3$ is fluoro or chloro; $R^{5B}$ can be independently hydrogen, deuterium or an unsubstituted $C_{1-4}$ alkyl; each $X^D$ can be independently deuterium, chloro or fluoro; and p4 can be independently 0, 1, 2, 3, 4, 5 or 6.

In some embodiments of Formula (Id), each $X^3$ can be fluoro. In some embodiments, each $X^3$ can be chloro. In some embodiments, two of $X^3$ can be fluoro, and one of $X^3$ can be chloro. In some embodiments, two of $X^3$ can be chloro, and one of $X^3$ can be fluoro. In some embodiments, two of $X^3$ can be fluoro, and one of $X^3$ can be hydrogen. In some embodiments, two of $X^3$ can be fluoro, and one of $X^3$ can be deuterium. In some embodiments, two of $X^3$ can be fluoro, and one of $X^3$ can be an unsubstituted $C_{1-4}$ alkyl. In some embodiments, two of $X^3$ can be chloro, and one of $X^3$ can be hydrogen. In some embodiments, two of $X^3$ can be chloro, and one of $X^3$ can be deuterium. In some embodiments, two of $X^3$ can be chloro, and one of $X^3$ can be an unsubstituted $C_{1-4}$ alkyl. Examples of $C_{1-4}$ alkyl groups include methyl, ethyl, n-propyl, iso-propyl, n-butyl, iso-butyl and tert-butyl.

In some embodiments of Formula (Id), $R^{5B}$ can be hydrogen. In other embodiments, $R^{5B}$ can be deuterium. In still other embodiments, $R^{5B}$ can be an unsubstituted $C_{1-4}$ alkyl. Examples of $C_{1-4}$ alkyl groups include methyl, ethyl, n-propyl, iso-propyl, n-butyl, iso-butyl and tert-butyl.

In some embodiments of Formula (Id), p4 can be 0. In other embodiments, each $X^D$ can be deuterium, and p4 can be 6. In some embodiments, each $X^D$ can be deuterium, and p4 can be 5. In still other embodiments, each $X^D$ can be deuterium, and p4 can be 4. In yet still other embodiments, each $X^D$ can be deuterium, and p4 can be 3. In some embodiments, each $X^D$ can be deuterium, and p4 can be 2. In other embodiments, each $X^D$ can be deuterium, and p4 can be 1. In some embodiments, each $X^D$ can be chloro, and p4 can be 6. In other embodiments, each $X^D$ can be chloro, and p4 can be 5. In still other embodiments, each $X^D$ can be chloro, and p4 can be 4. In yet still other embodiments, each $X^D$ can be chloro, and p4 can be 3. In some embodiments, each $X^D$ can be chloro, and p4 can be 2. In other embodiments, each $X^D$ can be chloro, and p4 can be 1. In some embodiments, each $X^D$ can be fluoro, and p4 can be 6. In other embodiments, each $X^D$ can be fluoro, and p4 can be 5. In still other embodiments, each $X^D$ can be fluoro, and p4 can be 4. In yet still other embodiments, each $X^D$ can be fluoro, and p4 can be 3. In some embodiments, each $X^D$ can be fluoro, and p4 can be 2. In other embodiments, each $X^D$ can be fluoro, and p4 can be 1.

Formula (Ie)

In some embodiments, the compound, or pharmaceutically acceptable salt thereof, can be a compound of Formula (Ie), or pharmaceutically acceptable salt thereof, having the structure:

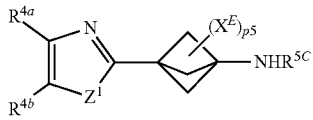

(Ie)

In some embodiments of Formula (Ie), $R^{4a}$ and $R^{4b}$ can be independently hydrogen, deuterium, an unsubstituted $C_{1-4}$ alkyl, a hydroxy substituted $C_{1-4}$ alkyl or $-C(X^{16})_3$, provided that at least one of $R^{4a}$ and $R^{4b}$ is $-C(X^{16})_3$; each $X^{16}$ can be independently hydrogen, deuterium, an unsubstituted $C_{1-4}$ alkyl, fluoro or chloro, provided that at least two of $X^{16}$ is fluoro or chloro; $R^{5C}$ can be selected from hydrogen, deuterium, an unsubstituted $C_{1-4}$ alkyl and $C(=O)R^{12}$; $R^{12}$ can be selected from hydrogen, deuterium, an unsubstituted $C_{1-30}$ alkyl and an unsubstituted $C_{2-30}$ alkenyl; each $X^E$ can be independently deuterium, chloro or fluoro; p5 can be independently 0, 1, 2, 3, 4, 5 or 6; and $Z^1$ can be nitrogen, oxygen or sulfur.

In some embodiments of Formula (Ie), $R^{4a}$ can be hydrogen, and $R^{4b}$ can be $-C(X^{16})_3$. In some embodiments, $R^{4a}$ can be deuterium, and $R^{4b}$ can be $-C(X^{16})_3$. In some embodiments, $R^{4a}$ can be methyl, and $R^{4b}$ can be $-C(X^{16})_3$. In some embodiments, $R^{4a}$ can be ethyl, and $R^{4b}$ can be $-C(X^{16})_3$. In some embodiments, $R^{4a}$ can be propyl, such as n-propyl or iso-propyl, and $R^{4b}$ can be $-C(X^{16})_3$. In some embodiments, $R^{4a}$ can be butyl, for example, n-butyl, iso-butyl or tert-butyl, and $R^{4b}$ can be $-C(X^{16})_3$. In other embodiments, $R^{4a}$ can be a hydroxy substituted $C_{1-4}$ alkyl (for example, HO—$CH_2$—), and $R^{4b}$ can be $-C(X^{16})_3$. In any embodiments of this paragraph, each $X^{16}$ can be fluoro. In any embodiments of this paragraph, each $X^{16}$ can be chloro. In any embodiments of this paragraph, two of $X^{16}$ can be fluoro, and one of $X^{16}$ can be chloro. In any embodiments of this paragraph, two of $X^{16}$ can be chloro, and one of $X^{16}$ can be fluoro. In any embodiments of this paragraph, two of $X^{16}$ can be fluoro, and one of $X^{16}$ can be hydrogen. In any embodiments of this paragraph, two of $X^{16}$ can be fluoro, and one of $X^{16}$ can be deuterium. In any embodiments of this paragraph, two of $X^{16}$ can be fluoro, and one of $X^{16}$ can be an unsubstituted $C_{1-4}$ alkyl. In any embodiments of this paragraph, two of $X^{16}$ can be chloro, and one of $X^{16}$ can be hydrogen. In any embodiments of this paragraph, two of $X^{16}$ can be chloro, and one of $X^{16}$ can be deuterium. In any embodiments of this paragraph, two of $X^{16}$ can be chloro, and one of $X^{16}$ can be an unsubstituted $C_{1-4}$ alkyl.

In some embodiments of Formula (Ie), $R^{4b}$ can be hydrogen, and $R^{4a}$ can be $-C(X^{16})_3$. In some embodiments, $R^{4b}$ can be deuterium, and $R^{4a}$ can be $-C(X^{16})_3$. In some embodiments, $R^{4b}$ can be methyl, and $R^{4a}$ can be $-C(X^{16})_3$. In some embodiments, $R^{4b}$ can be ethyl, and $R^{4a}$ can be $-C(X^{16})_3$. In some embodiments, $R^{4b}$ can be propyl, such as n-propyl or iso-propyl, and $R^{4a}$ can be $-C(X^{16})_3$. In some embodiments, $R^{4b}$ can be butyl, for example, n-butyl, iso-butyl or tert-butyl, and $R^{4a}$ can be $-C(X^{16})_3$. In other embodiments, $R^{4b}$ can be a hydroxy substituted $C_{1-4}$ alkyl (such as, HO—$CH_2$—), and $R^{4a}$ can be $-C(X^{16})_3$. In any embodiments of this paragraph, each $X^{16}$ can be fluoro. In any embodiments of this paragraph, each $X^{16}$ can be chloro. In any embodiments of this paragraph, two of $X^{16}$ can be fluoro, and one of $X^{16}$ can be chloro. In any embodiments of this paragraph, two of $X^{16}$ can be chloro, and one of $X^{16}$ can be fluoro. In any embodiments of this paragraph, two of $X^{16}$ can be fluoro, and one of $X^{16}$ can be hydrogen. In any embodiments of this paragraph, two of $X^{16}$ can be fluoro, and one of $X^{16}$ can be deuterium. In any embodiments of this paragraph, two of $X^{16}$ can be fluoro, and one of $X^{16}$ can be an unsubstituted $C_{1-4}$ alkyl. In any embodiments of this paragraph, two of $X^{16}$ can be chloro, and one of $X^{16}$ can be hydrogen. In any embodiments of this paragraph, two of $X^{16}$ can be chloro, and one of $X^{16}$ can be deuterium. In any embodiments of this paragraph, two of $X^{16}$ can be chloro, and one of $X^{16}$ can be an unsubstituted $C_{1-4}$ alkyl. Examples of $C_{1-4}$ alkyl groups, for example for $X^{16}$, include methyl, ethyl, n-propyl, iso-propyl, n-butyl, iso-butyl and tert-butyl.

In some embodiments of Formula (Ie), $R^{5C}$ can be hydrogen. In other embodiments, $R^{5C}$ can be deuterium. In still other embodiments, $R^{5C}$ can be an unsubstituted $C_{1-4}$ alkyl.

Examples of $C_{1-4}$ alkyl groups include methyl, ethyl, n-propyl, iso-propyl, n-butyl, iso-butyl and tert-butyl. In still other embodiments, $R^{5C}$ can be $C(\!=\!O)R^{12}$.

When $R^{5C}$ is $C(\!=\!O)R^{12}$, $R^{12}$ can be a variety of groups. In some embodiments, $R^{12}$ can be hydrogen. In other embodiments, $R^{12}$ can be deuterium. When $R^{12}$ is an alkyl group, the number of carbon atoms of the alkyl group can vary. The alkyl group can be a long alkyl having 1 to 30 carbons, a medium alkyl having 1 to 12 carbon atoms or a lower alkyl having 1 to 6 carbon atoms. In some embodiments, $R^{12}$ can be an unsubstituted $C_{1-6}$ alkyl. In other embodiments, $R^{12}$ can be an unsubstituted $C_{1-12}$ alkyl. In still other embodiments, $R^{12}$ can be an unsubstituted $C_{1-30}$ alkyl. In yet still other embodiments, $R^{12}$ can be an unsubstituted $C_{7-26}$ alkyl. In even still other embodiments, $R^{12}$ can be an unsubstituted $C_{12-26}$ alkyl. Examples of lower alkyl groups include methyl, ethyl, n-propyl, iso-propyl, n-butyl, iso-butyl, a tert-butyl, pentyl (straight and branched) and hexyl (straight and branched). Examples of unsubstituted $C_{1-30}$ alkyls include, but are not limited to, —$(CH_2)_6CH_3$, —$(CH_2)_8CH_3$, —$(CH_2)_{10}CH_3$, —$(CH_2)_{12}CH_3$, —$(CH_2)_{14}CH_3$, —$(CH_2)_{16}CH_3$, —$(CH_2)_{18}CH_3$, —$(CH_2)_{20}CH_3$, —$(CH_2)_{22}CH_3$ and —$(CH_2)_{24}CH_3$.

Similar to alkyls, alkenyls can be a long alkenyl having 2 to 30 carbons, a medium alkenyl having 2 to 12 carbon atoms or a lower alkenyl having 2 to 6 carbon atoms. In some embodiments, $R^{12}$ can be an unsubstituted $C_{2-30}$ alkenyl. In other embodiments, $R^{12}$ can be an unsubstituted $C_{14-22}$ alkenyl. Examples of unsubstituted $C_{2-30}$ alkenyls include, but are not limited to, —$(CH_2)_7CH\!=\!CH(CH_2)_3CH_3$, —$(CH_2)_7CH\!=\!CHCH_2CH\!=\!CH(CH_2)_4CH_3$, —$(CH_2)_7CH\!=\!CH(CH_2)_7CH_3$, —$(CH_2)_7CH\!=\!CHCH_2CH\!=\!CH(CH_2)_4CH_3$, —$(CH_2)_7CH\!=\!CH(CH_2)_7CH_3$, —$(CH_2)_7CH\!=\!CHCH_2CH\!=\!CHCH_2CH\!=\!CHCH_2CH_3$, —$(CH_2)_9CH\!=\!CH(CH_2)_5CH_3$, —$(CH_2)_3CH\!=\!CHCH_2CH\!=\!CHCH_2CH\!=\!CHCH_2CH\!=\!CH(CH_2)_4CH_3$, —$(CH_2)_{11}CH\!=\!CH(CH_2)_7CH_3$, —$(CH_2)_3CH\!=\!CHCH_2CH\!=\!CHCH_2CH\!=\!CHCH_2CH\!=\!CHCH_2CH_3$, —$(CH_2)_4CH\!=\!CHCH(CH_3)_2$ and —$(CH_2)_2CH\!=\!CHCH_2CH\!=\!CHCH_2CH\!=\!CHCH_2CH\!=\!CHCH_2CH\!=\!CHCH_2CH_3$.

In some embodiments, $R^{12}$ can be the aliphatic tail of a saturated or an unsaturated fatty acid. As an example, $R^{12}$ can be the aliphatic tail of caprylic acid (HOOC(*CH$_2$*)$_6$*CH$_3$*). In this example of caprylic acid, the aliphatic tail is bolded and italicized. When the saturated or an unsaturated fatty acid becomes part of a compound of Formula (Ie), the carbon of the carboxylic acid of the saturated or an unsaturated fatty acid becomes the carbon of C(=O)R$^{12}$ that is bold and underlined. For example, when $\overline{R}^{12}$ is the aliphatic tail of caprylic acid, the compound of Formula (Ie) can have the following structure:

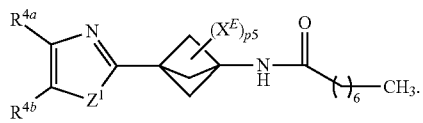

A non-limiting list of suitable saturated or an unsaturated fatty acids are myristoleic acid, palmitoleic, sapienic acid, linoleic acid, oleic acid, linoleiaidic acid, elaidic acid, alpha-linolenic acid, vaccenic acid, arachidonic acid, erucic acid, eicosapentaenoic acid, (E)-8-methylnon-6-enoic acid, docosahexaenoic acid, caprylic acid, capric acid, lauric acid, myristic acid, palmitic acid, stearic acid, arachidic acid, behenic acid, lignoceric acid and cerotic acid.

In some embodiments of Formula (Ie), p5 can be 0. In other embodiments, each $X^E$ can be deuterium, and p5 can be 6. In still other embodiments, each $X^E$ can be deuterium, and p5 can be 5. In yet still other embodiments, each $X^E$ can be deuterium, and p5 can be 4. In some embodiments, each $X^E$ can be deuterium, and p5 can be 3. In other embodiments, each $X^E$ can be deuterium, and p5 can be 2. In still other embodiments, each $X^E$ can be deuterium, and p5 can be 1. In some embodiments, each $X^E$ can be chloro, and p5 can be 6. In other embodiments, each $X^E$ can be chloro, and p5 can be 5. In still other embodiments, each $X^E$ can be chloro, and p5 can be 4. In yet still other embodiments, each $X^E$ can be chloro, and p5 can be 3. In some embodiments, each $X^E$ can be chloro, and p5 can be 2. In other embodiments, each $X^E$ can be chloro, and p5 can be 1. In some embodiments, each $X^E$ can be fluoro, and p5 can be 6. In other embodiments, each $X^E$ can be fluoro, and p5 can be 5. In still other embodiments, each $X^E$ can be fluoro, and p5 can be 4. In yet still other embodiments, each $X^E$ can be fluoro, and p5 can be 3. In some embodiments, each $X^E$ can be fluoro, and p5 can be 2. In other embodiments, each $X^E$ can be fluoro, and p5 can be 1.

In some embodiments of Formula (Ie), $Z^1$ can be nitrogen. In other embodiments, $Z^1$ can be oxygen. In still other embodiments, $Z^1$ can be sulfur.

Formula (If)

In some embodiments, the compound, or pharmaceutically acceptable salt thereof, can be a compound of Formula (If), or pharmaceutically acceptable salt thereof, having the structure:

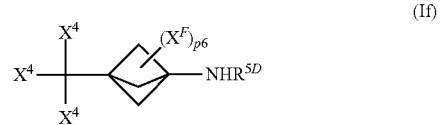

In some embodiments of Formula (If), each $X^4$ can be independently hydrogen, deuterium, an unsubstituted $C_{1-4}$ alkyl, fluoro or chloro, provided that at least two of $X^4$ is fluoro or chloro; $R^{5D}$ can be hydrogen, deuterium or an unsubstituted $C_{1-4}$ alkyl; each $X^F$ can be independently deuterium, chloro or fluoro; and p6 can be independently 0, 1, 2, 3, 4, 5 or 6.

In some embodiments of Formula (If), each $X^4$ can be fluoro. In some embodiments, each $X^4$ can be chloro. In some embodiments, two of $X^4$ can be fluoro, and one of $X^4$ can be chloro. In some embodiments, two of $X^4$ can be chloro, and one of $X^4$ can be fluoro. In some embodiments, two of $X^4$ can be fluoro, and one of $X^4$ can be hydrogen. In some embodiments, two of $X^4$ can be fluoro, and one of $X^4$ can be deuterium. In some embodiments, two of $X^4$ can be fluoro, and one of $X^4$ can be an unsubstituted $C_{1-4}$ alkyl. In some embodiments, two of $X^4$ can be chloro, and one of $X^4$ can be hydrogen. In some embodiments, two of $X^4$ can be chloro, and one of $X^4$ can be deuterium. In some embodiments, two of $X^4$ can be chloro, and one of $X^4$ can be an unsubstituted $C_{1-4}$ alkyl. Examples of $C_{1-4}$ alkyl groups include methyl, ethyl, n-propyl, iso-propyl, n-butyl, iso-butyl and tert-butyl.

In some embodiments of Formula (If), $R^{5D}$ can be hydrogen. In some embodiments, $R^{5D}$ can be deuterium. In some embodiments, $R^{5D}$ can be an unsubstituted $C_{1-4}$ alkyl, such as methyl, ethyl, n-propyl, iso-propyl, n-butyl, iso-butyl and tert-butyl.

In some embodiments of Formula (If), p6 can be 0. In other embodiments, each $X^F$ can be deuterium, and p6 can be 6. In still other embodiments, each $X^F$ can be deuterium, and p6 can be 5. In yet still embodiments, each $X^F$ can be deuterium, and p6 can be 4. In some embodiments, each $X^F$ can be deuterium, and p6 can be 3. In other embodiments, each $X^F$ can be deuterium, and p6 can be 2. In still other embodiments, each $X^F$ can be deuterium, and p6 can be 1. In some embodiments, each $X^F$ can be chloro, and p6 can be 6. In other embodiments, each $X^F$ can be chloro, and p6 can be 5. In still other embodiments, each $X^F$ can be chloro, and p6 can be 4. In yet still other embodiments, each $X^F$ can be chloro, and p6 can be 3. In some embodiments, each $X^F$ can be chloro, and p6 can be 2. In other embodiments, each $X^F$ can be chloro, and p6 can be 1. In some embodiments, each $X^F$ can be fluoro, and p6 can be 6. In other embodiments, each $X^F$ can be fluoro, and p6 can be 5. In still other embodiments, each $X^F$ can be fluoro, and p6 can be 4. In yet still other embodiments, each $X^F$ can be fluoro, and p6 can be 3. In some embodiments, each $X^F$ can be fluoro, and p6 can be 2. In other embodiments, each $X^F$ can be fluoro, and p6 can be 1.

In some embodiments of Formula (If), when at least two of $X^4$ are halogen, such as fluoro and chloro, then $R^{5D}$ cannot be hydrogen. In other embodiments, when at least two of $X^4$ are halogen, such as fluoro and chloro, and p6 is 0, then $R^{5D}$ cannot be hydrogen. In still other embodiments, when at least two of $X^4$ are fluoro and p6 is 0, then $R^{5D}$ cannot be hydrogen. In some embodiments, when at least two of $X^4$ are halogen, such as fluoro and chloro, then $R^{5D}$ cannot be an unsubstituted $C_{1-4}$ alkyl. In other embodiments, when at least two of $X^4$ are halogen, such as fluoro and chloro, and p6 is 0, then $R^{5D}$ cannot be an unsubstituted $C_{1-4}$ alkyl. In still other embodiments, when at least two of $X^4$ are fluoro, and p6 is 0, then $R^{5D}$ cannot be an unsubstituted $C_{1-4}$ alkyl. In some embodiments, when one of $X^4$ is an unsubstituted $C_{1-4}$ alkyl then $R^{5D}$ cannot be hydrogen. In other embodiments, when one of $X^4$ is an unsubstituted $C_{1-4}$ alkyl and p6 is 0, then $R^{5D}$ cannot be hydrogen. In still other embodiments, when one of $X^4$ is methyl and p6 is 0, then $R^{5D}$ cannot be hydrogen. In some embodiments, when one of $X^4$ is hydrogen, then $R^{5D}$ cannot be hydrogen. In other embodiments, when one of $X^4$ is hydrogen and p6 is 0, then $R^{5D}$ cannot be hydrogen. In some embodiment, when p6 is 0, then $R^{5D}$ cannot be hydrogen. In other embodiments, when p6 is 0, then $R^{5D}$ cannot be an unsubstituted $C_{1-4}$ alkyl. In still other embodiments, when p6 is 0, then $—C(X^4)_3$ cannot be $—CF_3$. In yet still other embodiments, when p6 is 0, then $—C(X^4)_3$ cannot be $—CCl_3$. In some embodiments, when $—C(X^4)_3$ is $—CF_3$ and p6 is 0, then $R^{5D}$ cannot be an unsubstituted $C_4$ alkyl. In some embodiments, p6 cannot be 0. Examples of $C_{1-4}$ alkyl groups include methyl, ethyl, n-propyl, iso-propyl, n-butyl, iso-butyl and tert-butyl. Examples of $C_4$ alkyl groups include n-butyl, iso-butyl and tert-butyl. In other embodiments, a compound of Formula (If), or a pharmaceutically acceptable salt thereof, cannot one or more of the following compounds,

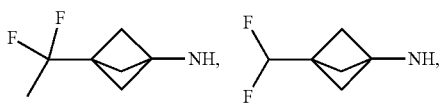

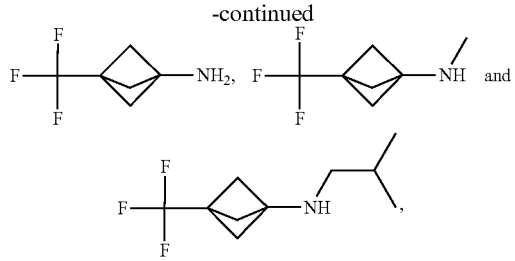

or a pharmaceutically acceptable salt of any of the foregoing.

Formula (Ig)

In some embodiments, the compound, or pharmaceutically acceptable salt thereof, can be a compound of Formula (Ig), or pharmaceutically acceptable salt thereof, having the structure:

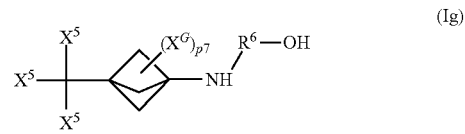

In some embodiments of Formula (Ig), each $X^5$ can be independently hydrogen, deuterium, an unsubstituted $C_{1-4}$ alkyl, fluoro or chloro, provided that at least two of $X^5$ is fluoro or chloro; $R^6$ can be $—(CH_2)_m—$; m can be 1, 2, 3 or 4; each $X^G$ can be independently deuterium, chloro or fluoro; and p7 can be independently 0, 1, 2, 3, 4, 5 or 6.

In some embodiments of Formula (Ig), each $X^5$ can be fluoro. In some embodiments, each $X^5$ can be chloro. In some embodiments, two of $X^5$ can be fluoro, and one of $X^5$ can be chloro. In some embodiments, two of $X^5$ can be chloro, and one of $X^5$ can be fluoro. In some embodiments, two of $X^5$ can be fluoro, and one of $X^5$ can be hydrogen. In some embodiments, two of $X^5$ can be fluoro, and one of $X^5$ can be deuterium. In some embodiments, two of $X^5$ can be fluoro, and one of $X^5$ can be an unsubstituted $C_{1-4}$ alkyl. In some embodiments, two of $X^5$ can be chloro, and one of $X^5$ can be hydrogen. In some embodiments, two of $X^5$ can be chloro, and one of $X^5$ can be deuterium. In some embodiments, two of $X^5$ can be chloro, and one of $X^5$ can be an unsubstituted $C_{1-4}$ alkyl. Examples of $C_{1-4}$ alkyl groups include methyl, ethyl, n-propyl, iso-propyl, n-butyl, iso-butyl and tert-butyl.

In some embodiments of Formula (Ig), $R^6$ can be $—(CH_2)_m—$, and m can be 1. In other embodiments, $R^6$ can be $—(CH_2)_m—$, and m can be 2. In still other embodiments, $R^6$ can be $—(CH_2)_m—$, and m can be 3. In yet still other embodiments, $R^6$ can be $—(CH_2)_m—$, and m can be 4.

In some embodiments of Formula (Ig), p7 can be 0. In other embodiments, each $X^G$ can be deuterium, and p7 can be 6. In still other some embodiments, each $X^G$ can be deuterium, and p7 can be 5. In yet still other embodiments, each $X^G$ can be deuterium, and p7 can be 4. In some embodiments, each $X^G$ can be deuterium, and p7 can be 3. In other embodiments, each $X^G$ can be deuterium, and p7 can be 2. In still other embodiments, each $X^G$ can be deuterium, and p7 can be 1. In some embodiments, each $X^G$ can be chloro, and p7 can be 6. In other embodiments, each $X^G$ can be chloro, and p7 can be 5. In still other embodiments, each $X^G$ can be chloro, and p7 can be 4. In yet still other embodiments, each $X^G$ can be chloro, and p7 can be 3.

In some embodiments, each $X^G$ can be chloro, and p7 can be 2. In other embodiments, each $X^G$ can be chloro, and p7 can be 1. In some embodiments, each $X^G$ can be fluoro, and p7 can be 6. In other embodiments, each $X^G$ can be fluoro, and p7 can be 5. In still other embodiments, each $X^G$ can be fluoro, and p7 can be 4. In yet still other embodiments, each $X^G$ can be fluoro, and p7 can be 3. In some embodiments, each $X^G$ can be fluoro, and p7 can be 2. In other embodiments, each $X^G$ can be fluoro, and p7 can be 1.

Formula (Ih)

In some embodiments, the compound, or pharmaceutically acceptable salt thereof, can be a compound of Formula (Ih), or pharmaceutically acceptable salt thereof, having the structure:

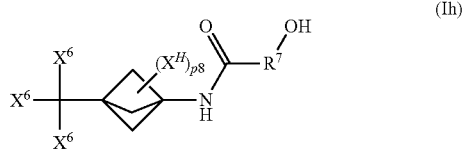

(Ih)

In some embodiments of Formula (Ih), each $X^6$ can be independently hydrogen, deuterium, an unsubstituted $C_{1-4}$ alkyl, fluoro or chloro, provided that at least two of $X^6$ is fluoro or chloro; $R^7$ can be —$(CH_2)_m$—; m can be 1, 2, 3 or 4; each $X^H$ can be independently deuterium, chloro or fluoro; and p8 can be independently 0, 1, 2, 3, 4, 5 or 6.

In some embodiments of Formula (Ih), each $X^6$ can be fluoro. In some embodiments, each $X^6$ can be chloro. In some embodiments, two of $X^6$ can be fluoro, and one of $X^6$ can be chloro. In some embodiments, two of $X^6$ can be chloro, and one of $X^6$ can be fluoro. In some embodiments, two of $X^6$ can be fluoro, and one of $X^6$ can be hydrogen. In some embodiments, two of $X^6$ can be fluoro, and one of $X^6$ can be deuterium. In some embodiments, two of $X^6$ can be fluoro, and one of $X^6$ can be an unsubstituted $C_{1-4}$ alkyl. In some embodiments, two of $X^6$ can be chloro, and one of $X^6$ can be hydrogen. In some embodiments, two of $X^6$ can be chloro, and one of $X^6$ can be deuterium. In some embodiments, two of $X^6$ can be chloro, and one of $X^6$ can be an unsubstituted $C_{1-4}$ alkyl. Examples of $C_{1-4}$ alkyl groups include methyl, ethyl, n-propyl, iso-propyl, n-butyl, iso-butyl and tert-butyl.

In some embodiments of Formula (Ih), $R^7$ can be —$(CH_2)_m$—, and m can be 1. In other embodiments, $R^7$ can be —$(CH_2)_m$—, and m can be 2. In still other embodiments, $R^7$ can be —$(CH_2)_m$—, and m can be 3. In yet still embodiments, $R^7$ can be —$(CH_2)_m$—, and m can be 4.

In some embodiments of Formula (Ih), p8 can be 0. In other embodiments, each $X^H$ can be deuterium, and p8 can be 6. In still other embodiments, each $X^H$ can be deuterium, and p8 can be 5. In yet still other embodiments, each $X^H$ can be deuterium, and p8 can be 4. In some embodiments, each $X^H$ can be deuterium, and p8 can be 3. In other embodiments, each $X^H$ can be deuterium, and p8 can be 2. In still other embodiments, each $X^H$ can be deuterium, and p8 can be 1. In some embodiments, each $X^H$ can be chloro, and p8 can be 6. In other embodiments, each $X^H$ can be chloro, and p8 can be 5. In still other embodiments, each $X^H$ can be chloro, and p8 can be 4. In yet still other embodiments, each $X^H$ can be chloro, and p8 can be 3. In some embodiments, each $X^H$ can be chloro, and p8 can be 2. In other embodiments, each $X^H$ can be chloro, and p8 can be 1. In some embodiments, each $X^H$ can be fluoro, and p8 can be 6. In other embodiments, each $X^H$ can be fluoro, and p8 can be 5. In still other embodiments, each $X^H$ can be fluoro, and p8 can be 4. In yet still other embodiments, each $X^H$ can be fluoro, and p8 can be 3. In some embodiments, each $X^H$ can be fluoro, and p8 can be 2. In other embodiments, each $X^H$ can be fluoro, and p8 can be 1.

Formula (Ik)

In some embodiments, the compound, or pharmaceutically acceptable salt thereof, can be a compound of Formula (Ik), or pharmaceutically acceptable salt thereof, having the structure:

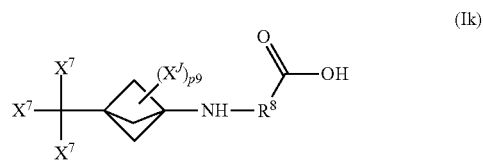

(Ik)

In some embodiments of Formula (Ik), each $X^7$ can be independently hydrogen, deuterium, an unsubstituted C1-4 alkyl, fluoro or chloro, provided that at least two of $X^7$ is fluoro or chloro; $R^8$ can be —$(CH_2)_m$—; m can be 1, 2, 3 or 4; each $X^J$ can be independently deuterium, chloro or fluoro; and p9 can be independently 0, 1, 2, 3, 4, 5 or 6.

In some embodiments of Formula (Ik), each $X^7$ can be fluoro. In some embodiments, each $X^7$ can be chloro. In some embodiments, two of $X^7$ can be fluoro, and one of $X^7$ can be chloro. In some embodiments, two of $X^7$ can be chloro, and one of $X^7$ can be fluoro. In some embodiments, two of $X^7$ can be fluoro, and one of $X^7$ can be hydrogen. In some embodiments, two of $X^7$ can be fluoro, and one of $X^7$ can be deuterium. In some embodiments, two of $X^7$ can be fluoro, and one of $X^7$ can be an unsubstituted $C_{1-4}$ alkyl. In some embodiments, two of $X^7$ can be chloro, and one of $X^7$ can be hydrogen. In some embodiments, two of $X^7$ can be chloro, and one of $X^7$ can be deuterium. In some embodiments, two of $X^7$ can be chloro, and one of $X^7$ can be an unsubstituted $C_{1-4}$ alkyl. Examples of $C_{1-4}$ alkyl groups include methyl, ethyl, n-propyl, iso-propyl, n-butyl, iso-butyl and tert-butyl.

In some embodiments of Formula (Ik), $R^8$ can be —$(CH_2)_m$—, and m can be 1. In other embodiments, $R^8$ can be —$(CH_2)_m$—, and m can be 2. In still other embodiments, $R^8$ can be —$(CH_2)_m$—, and m can be 3. In yet still other embodiments, $R^8$ can be —$(CH_2)_m$—, and m can be 4.

In some embodiments of Formula (Ik), p9 can be 0. In other embodiments, each $X^J$ can be deuterium, and p9 can be 6. In still other embodiments, each $X^J$ can be deuterium, and p9 can be 5. In yet still other embodiments, each $X^J$ can be deuterium, and p9 can be 4. In some embodiments, each $X^J$ can be deuterium, and p9 can be 3. In other embodiments, each $X^J$ can be deuterium, and p9 can be 2. In still other embodiments, each $X^J$ can be deuterium, and p9 can be 1. In some embodiments, each $X^J$ can be chloro, and p9 can be 6. In other embodiments, each $X^J$ can be chloro, and p9 can be 5. In still other embodiments, each $X^J$ can be chloro, and p9 can be 4. In yet still other embodiments, each $X^J$ can be chloro, and p9 can be 3. In some embodiments, each $X^J$ can be chloro, and p9 can be 2. In other embodiments, each $X^J$ can be chloro, and p9 can be 1. In some embodiments, each $X^J$ can be fluoro, and p9 can be 6. In other embodiments, each $X^J$ can be fluoro, and p9 can be 5. In still other embodiments, each $X^J$ can be fluoro, and p9 can be 4. In yet still other embodiments, each $X^J$ can be fluoro, and p9 can be 3. In some embodiments, each $X^J$ can be fluoro, and p9 can be 2. In other embodiments, each $X^J$ can be fluoro, and p9 can be 1.

Formula (Im)

In some embodiments, the compound, or pharmaceutically acceptable salt thereof, can be a compound of Formula (Im), or pharmaceutically acceptable salt thereof, having the structure:

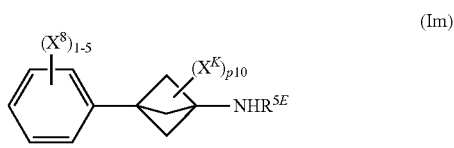

(Im)

In some embodiments of Formula (Im), each $X^8$ can be independently deuterium, fluoro or chloro; $R^{5E}$ can be hydrogen, deuterium or an unsubstituted $C_{1-4}$ alkyl; each $X^K$ can be independently deuterium, chloro or fluoro; and p10 can be independently 0, 1, 2, 3, 4, 5 or 6.

In any embodiments of Formula (Im) of this paragraph, five of $X^8$ can be deuterium. In any embodiments of this paragraph, four of $X^8$ can be deuterium. In any embodiments of this paragraph, three of $X^8$ can be deuterium. In any embodiments of this paragraph, two of $X^8$ can be deuterium. In any embodiments of this paragraph, one of $X^8$ can be deuterium. In any embodiments of this paragraph, five of $X^8$ can be fluoro. In any embodiments of this paragraph, four of $X^8$ can be fluoro. In any embodiments of this paragraph, three of $X^8$ can be fluoro. In any embodiments of this paragraph, two of $X^8$ can be fluoro. In any embodiments of this paragraph, one of $X^8$ can be fluoro. In any embodiments of this paragraph, five of $X^8$ can be chloro. In any embodiments of this paragraph, four of $X^8$ can be chloro. In any embodiments of this paragraph, three of $X^8$ can be chloro. In any embodiments of this paragraph, two of $X^8$ can be chloro. In any embodiments of this paragraph, one of $X^8$ can be chloro.

In some embodiments of Formula (Im), $R^{5E}$ can be hydrogen. In other embodiments, $R^{5E}$ can be deuterium. In still other embodiments, $R^{5E}$ can be an unsubstituted $C_{1-4}$ alkyl, for example, methyl, ethyl, n-propyl, iso-propyl, n-butyl, iso-butyl and tert-butyl.

In some embodiments of Formula (Im), p10 can be 0. In other embodiments, each $X^K$ can be deuterium, and p10 can be 6. In still other embodiments, each $X^K$ can be deuterium, and p10 can be 5. In yet still other embodiments, each $X^K$ can be deuterium, and p10 can be 4. In some embodiments, each $X^K$ can be deuterium, and p10 can be 3. In other embodiments, each $X^K$ can be deuterium, and p10 can be 2. In still other embodiments, each $X^K$ can be deuterium, and p10 can be 1. In some embodiments, each $X^K$ can be chloro, and p10 can be 6. In other embodiments, each $X^K$ can be chloro, and p10 can be 5. In still other embodiments, each $X^K$ can be chloro, and p10 can be 4. In yet still other embodiments, each $X^K$ can be chloro, and p10 can be 3. In some embodiments, each $X^K$ can be chloro, and p10 can be 2. In other embodiments, each $X^K$ can be chloro, and p10 can be 1. In some embodiments, each $X^K$ can be fluoro, and p10 can be 6. In other embodiments, each $X^K$ can be fluoro, and p10 can be 5. In still other embodiments, each $X^K$ can be fluoro, and p10 can be 4. In yet still other embodiments, each $X^K$ can be fluoro, and p10 can be 3. In some embodiments, each $X^K$ can be fluoro, and p10 can be 2. In other embodiments, each $X^K$ can be fluoro, and p10 can be 1.

In some embodiments of Formula (Im), when at least one of $X^8$ is halogen, such as fluoro and chloro, then $R^{5E}$ cannot be hydrogen. In other embodiments, when at least one of $X^8$ is halogen, such as fluoro and chloro, and p10 is 0, then $R^{5E}$ cannot be hydrogen. In still other embodiments, when at least one of $X^8$ is fluoro and p10 is 0, then $R^{5E}$ cannot be hydrogen. In some embodiments, when at least two of $X^8$ are halogen, such as fluoro and/or chloro, then $R^{5E}$ cannot be hydrogen. In other embodiments, when at least two of $X^8$ are halogen, such as fluoro and/or chloro, and p10 is 0, then $R^{5E}$ cannot be hydrogen. In still other embodiments, when at least two of $X^8$ are fluoro and p10 is 0, then $R^{5E}$ cannot be hydrogen. In some embodiments, when at least three of $X^8$ are halogen, such as fluoro and/or chloro, then $R^{5E}$ cannot be hydrogen. In other embodiments, when at least three of $X^8$ are halogen, such as fluoro and/or chloro, and p10 is 0, then $R^{5E}$ cannot be hydrogen. In still other embodiments, when at least three of $X^8$ are fluoro and p10 is 0, then $R^{5E}$ cannot be hydrogen. In some embodiments, when at least one of $X^8$ is deuterium, then $R^{5E}$ cannot be hydrogen. In other embodiments, when at least one of $X^8$ is deuterium and p10 is 0, then $R^{5E}$ cannot be hydrogen. In some embodiments, when at least two of $X^8$ is deuterium, then $R^{5E}$ cannot be hydrogen. In other embodiments, when at two one of $X^8$ is deuterium and p10 is 0, then $R^{5E}$ cannot be hydrogen. In some embodiments, when at least three of $X^8$ is deuterium, then $R^{5E}$ cannot be hydrogen. In other embodiments, when at least three of $X^8$ is deuterium and p10 is 0, then $R^{5E}$ cannot be hydrogen. In some embodiments, when at least one of $X^8$ is halogen, such as fluoro and chloro, then $R^{5E}$ cannot be an unsubstituted $C_{1-4}$ alkyl. In other embodiments, when at least one of $X^8$ is halogen, such as fluoro and chloro, and p10 is 0, then $R^{5E}$ cannot be an unsubstituted $C_{1-4}$ alkyl. In still other embodiments, when at least one of $X^8$ is fluoro and p10 is 0, then $R^{5E}$ cannot be an unsubstituted $C_{1-4}$ alkyl. In some embodiments, when at least two of $X^8$ is halogen, such as fluoro and chloro, then $R^{5E}$ cannot be an unsubstituted $C_{1-4}$ alkyl. In other embodiments, when at least two of $X^8$ is halogen, such as fluoro and chloro, and p10 is 0, then $R^{5E}$ cannot be an unsubstituted $C_{1-4}$ alkyl. In still other embodiments, when at least two of $X^8$ is fluoro and p10 is 0, then $R^{5E}$ cannot be an unsubstituted $C_{1-4}$ alkyl. In some embodiments, when at least three of $X^8$ is halogen, such as fluoro and chloro, then $R^{5E}$ cannot be an unsubstituted $C_{1-4}$ alkyl. In other embodiments, when at least three of $X^8$ is halogen, such as fluoro and chloro, and p10 is 0, then $R^{5E}$ cannot be an unsubstituted $C_{1-4}$ alkyl. In still other embodiments, when at least three of $X^8$ is fluoro and p10 is 0, then $R^{5E}$ cannot be an unsubstituted $C_{1-4}$ alkyl. In some embodiment, when p10 is 0, then $R^{5E}$ cannot be hydrogen. In other embodiments, when p10 is 0, then $R^{5E}$ cannot be an unsubstituted $C_{1-4}$ alkyl. In still other embodiments, when p10 is 0, then $R^{5E}$ cannot be deuterium. In still other embodiments, p10 cannot be 0. Examples of $C_{1-4}$ alkyl groups include methyl, ethyl, n-propyl, iso-propyl, n-butyl, iso-butyl and tert-butyl. In some embodiments, a compound of Formula (Im), or a pharmaceutically acceptable salt thereof, cannot be,

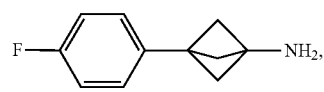

or a pharmaceutically acceptable salt thereof.

Formula (In)

In some embodiments, the compound, or pharmaceutically acceptable salt thereof, can be a compound of Formula (In), or pharmaceutically acceptable salt thereof, having the structure:

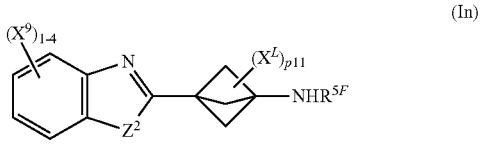

(In)

In some embodiments of Formula (In), each $X^9$ can be independently deuterium, fluoro or chloro; $R^{5E}$ can be hydrogen, deuterium or an unsubstituted $C_{1-4}$ alkyl; each $X^L$ can be independently deuterium, chloro or fluoro; p11 can be independently 0, 1, 2, 3, 4, 5 or 6; and $Z^2$ can be nitrogen, oxygen or sulfur.

In any embodiments of Formula (In) of this paragraph, four of $X^9$ can be deuterium. In any embodiments of this paragraph, three of $X^9$ can be deuterium. In any embodiments of this paragraph, two of $X^9$ can be deuterium. In any embodiments of this paragraph, one of $X^9$ can be deuterium. In any embodiments of this paragraph, four of $X^9$ can be fluoro. In any embodiments of this paragraph, three of $X^9$ can be fluoro. In any embodiments of this paragraph, two of $X^9$ can be fluoro. In any embodiments of this paragraph, one of $X^9$ can be fluoro. In any embodiments of this paragraph, four of $X^9$ can be chloro. In any embodiments of this paragraph, three of $X^9$ can be chloro. In any embodiments of this paragraph, two of $X^9$ can be chloro. In any embodiments of this paragraph, one of $X^9$ can be chloro.

In some embodiments of Formula (In), $R^{5F}$ can be hydrogen. In other embodiments, $R^{5F}$ can be deuterium. In still other embodiments, $R^{5F}$ can be an unsubstituted $C_{1-4}$ alkyl, such as methyl, ethyl, n-propyl, iso-propyl, n-butyl, iso-butyl and tert-butyl.

In some embodiments of Formula (In), p11 can be 0. In other embodiments, each $X^L$ can be deuterium, and p11 can be 6. In still other embodiments, each $X^L$ can be deuterium, and p11 can be 5. In yet still other embodiments, each $X^L$ can be deuterium, and p11 can be 4. In some embodiments, each $X^L$ can be deuterium, and p11 can be 3. In other embodiments, each $X^L$ can be deuterium, and p11 can be 2. In still other embodiments, each $X^L$ can be deuterium, and p11 can be 1. In some embodiments, each $X^L$ can be chloro, and p11 can be 6. In other embodiments, each $X^L$ can be chloro, and p11 can be 5. In still other embodiments, each $X^L$ can be chloro, and p11 can be 4. In yet still other embodiments, each $X^L$ can be chloro, and p11 can be 3. In some embodiments, each $X^L$ can be chloro, and p11 can be 2. In other embodiments, each $X^L$ can be chloro, and p11 can be 1. In some embodiments, each $X^L$ can be fluoro, and p11 can be 6. In other embodiments, each $X^L$ can be fluoro, and p11 can be 5. In still other embodiments, each $X^L$ can be fluoro, and p11 can be 4. In yet still other embodiments, each $X^L$ can be fluoro, and p11 can be 3. In some embodiments, each $X^L$ can be fluoro, and p11 can be 2. In other embodiments, each $X^L$ can be fluoro, and p11 can be 1.

In some embodiments of Formula (In), $Z^2$ can be nitrogen. In other embodiments, $Z^2$ can be oxygen. In still other embodiments, $Z^2$ can be sulfur.

Formula (Io)

In some embodiments, the compound, or pharmaceutically acceptable salt thereof, can be a compound of Formula (Io), or pharmaceutically acceptable salt thereof, having the structure:

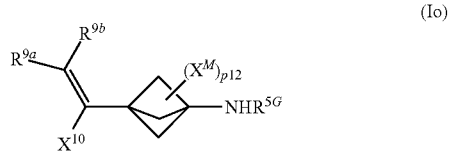

(Io)

In some embodiments of Formula (Io), $X^{10}$ can be deuterium, fluoro or chloro; $R^{9a}$ and $R^{9b}$ can be independently an unsubstituted $C_{1-4}$ alkyl; $R^{5G}$ can be hydrogen, deuterium or an unsubstituted $C_{1-4}$ alkyl; each $X^M$ can be independently deuterium, chloro or fluoro; and p12 can be independently 0, 1, 2, 3, 4, 5 or 6.

In some embodiments of Formula (Io), $R^{9a}$ can be methyl. In other embodiments, $R^{9a}$ can be ethyl. In still other embodiments, $R^{9a}$ can be propyl, such as n-propyl or iso-propyl. In yet still other embodiments, $R^{9a}$ can be butyl, for example, n-butyl, iso-butyl or tert-butyl. In some embodiments, including those of this paragraph, $R^{9b}$ can be methyl. In other embodiments, including those of this paragraph, $R^{9b}$ can be ethyl. In still other embodiments, including those of this paragraph, $R^{9b}$ can be propyl, such as n-propyl or iso-propyl. In yet still embodiments, including those of this paragraph, $R^{9b}$ can be butyl, for example, n-butyl, iso-butyl or tert-butyl.

In some embodiments of Formula (Io), $X^{10}$ can be deuterium. In other embodiments, $X^{10}$ can be fluoro. In still other embodiments, $X^{10}$ can be chloro.

In some embodiments of Formula (Io), $R^{5G}$ can be hydrogen. In other embodiments, $R^{5G}$ can be deuterium. In still other embodiments, $R^{5G}$ can be an unsubstituted $C_{1-4}$ alkyl. Examples of $C_{1-4}$ alkyl groups include methyl, ethyl, n-propyl, iso-propyl, n-butyl, iso-butyl and tert-butyl.

In some embodiments of Formula (Io), p12 can be 0. In other embodiments, each $X^M$ can be deuterium, and p12 can be 6. In still other embodiments, each $X^M$ can be deuterium, and p12 can be 5. In yet still other embodiments, each $X^M$ can be deuterium, and p12 can be 4. In some embodiments, each $X^M$ can be deuterium, and p12 can be 3. In other embodiments, each $X^M$ can be deuterium, and p12 can be 2. In still other embodiments, each $X^M$ can be deuterium, and p12 can be 1. In some embodiments, each $X^M$ can be chloro, and p12 can be 6. In other embodiments, each $X^M$ can be chloro, and p12 can be 5. In still other embodiments, each $X^M$ can be chloro, and p12 can be 4. In yet still other embodiments, each $X^M$ can be chloro, and p12 can be 3. In some embodiments, each $X^M$ can be chloro, and p12 can be 2. In other embodiments, each $X^M$ can be chloro, and p12 can be 1. In some embodiments, each $X^M$ can be fluoro, and p12 can be 6. In other embodiments, each $X^M$ can be fluoro, and p12 can be 5. In still other embodiments, each $X^M$ can be fluoro, and p12 can be 4. In yet still other embodiments, each $X^M$ can be fluoro, and p12 can be 3. In some embodiments, each $X^M$ can be fluoro, and p12 can be 2. In other embodiments, each $X^M$ can be fluoro, and p12 can be 1.

Formula (Ip)

In some embodiments, the compound, or pharmaceutically acceptable salt thereof, can be a compound of Formula (Ip), or pharmaceutically acceptable salt thereof, having the structure:

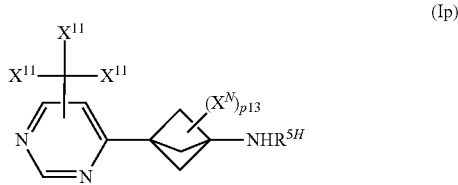

In some embodiments of Formula (Ip), each $X^{11}$ can be independently hydrogen, deuterium, an unsubstituted $C_{1-4}$ alkyl, fluoro or chloro, provided that at least two of $X^{11}$ is fluoro or chloro; $R^{5H}$ can be hydrogen, deuterium or an unsubstituted $C_{1-4}$ alkyl; each $X^N$ can be independently deuterium, chloro or fluoro; and p13 can be independently 0, 1, 2, 3, 4, 5 or 6.

In some embodiments of Formula (Ip), each $X^{11}$ can be fluoro. In some embodiments, each $X^{11}$ can be chloro. In some embodiments, two of $X^{11}$ can be fluoro, and one of $X^{11}$ can be chloro. In some embodiments, two of $X^{11}$ can be chloro, and one of $X^{11}$ can be fluoro. In some embodiments, two of $X^{11}$ can be fluoro, and one of $X^{11}$ can be hydrogen. In some embodiments, two of $X^{11}$ can be fluoro, and one of $X^{11}$ can be deuterium. In some embodiments, two of $X^{11}$ can be fluoro, and one of $X^{11}$ can be an unsubstituted $C_{1-4}$ alkyl. Examples of $C_{1-4}$ alkyl groups include methyl, ethyl, n-propyl, iso-propyl, n-butyl, iso-butyl and tert-butyl. In some embodiments, two of $X^{11}$ can be chloro, and one of $X^{11}$ can be hydrogen. In some embodiments, two of $X^{11}$ can be chloro, and one of $X^{11}$ can be deuterium. In some embodiments, two of $X^{11}$ can be chloro, and one of $X^{11}$ can be an unsubstituted $C_{1-4}$ alkyl. Examples of $C_{1-4}$ alkyl groups include methyl, ethyl, n-propyl, iso-propyl, n-butyl, iso-butyl and tert-butyl.

In some embodiments of Formula (Ip), $R^{5H}$ can be hydrogen. In other embodiments, $R^{5H}$ can be deuterium. In still other embodiments, $R^{5H}$ can be an unsubstituted $C_{1-4}$ alkyl, for example, methyl, ethyl, n-propyl, iso-propyl, n-butyl, iso-butyl and tert-butyl.

In some embodiments of Formula (Ip), p13 can be 0. In other embodiments, each $X^N$ can be deuterium, and p13 can be 6. In still other embodiments, each $X^N$ can be deuterium, and p13 can be 5. In yet still other embodiments, each $X^N$ can be deuterium, and p13 can be 4. In some embodiments, each $X^N$ can be deuterium, and p13 can be 3. In other embodiments, each $X^N$ can be deuterium, and p13 can be 2. In still other embodiments, each $X^N$ can be deuterium, and p13 can be 1. In some embodiments, each $X^N$ can be chloro, and p13 can be 6. In other embodiments, each $X^N$ can be chloro, and p13 can be 5. In still other embodiments, each $X^N$ can be chloro, and p13 can be 4. In yet still other embodiments, each $X^N$ can be chloro, and p13 can be 3. In some embodiments, each $X^N$ can be chloro, and p13 can be 2. In other embodiments, each $X^N$ can be chloro, and p13 can be 1. In some embodiments, each $X^N$ can be fluoro, and p13 can be 6. In other embodiments, each $X^N$ can be fluoro, and p13 can be 5. In still other embodiments, each $X^N$ can be fluoro, and p13 can be 4. In yet still other embodiments, each $X^N$ can be fluoro, and p13 can be 3. In some embodiments, each $X^N$ can be fluoro, and p13 can be 2. In other embodiments, each $X^N$ can be fluoro, and p13 can be 1.

Formula (Iq)

In some embodiments, the compound, or pharmaceutically acceptable salt thereof, can be a compound of Formula (Iq), or pharmaceutically acceptable salt thereof, having the structure:

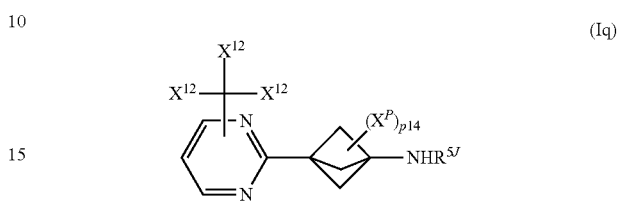

In some embodiments of Formula (Iq), each $X^{12}$ can be independently hydrogen, deuterium, an unsubstituted $C_{1-4}$ alkyl, fluoro or chloro, provided that at least two of $X^{12}$ is fluoro or chloro; $R^{5J}$ can be hydrogen, deuterium or an unsubstituted $C_{1-4}$ alkyl; each $X^P$ can be independently deuterium, chloro or fluoro; and p14 can be independently 0, 1, 2, 3, 4, 5 or 6.

In some embodiments of Formula (Iq), each $X^{12}$ can be fluoro. In some embodiments, each $X^{12}$ can be chloro. In some embodiments, two of $X^{12}$ can be fluoro, and one of $X^{12}$ can be chloro. In some embodiments, two of $X^{12}$ can be chloro, and one of $X^{12}$ can be fluoro. In some embodiments, two of $X^{12}$ can be fluoro, and one of $X^{12}$ can be hydrogen. In some embodiments, two of $X^{12}$ can be fluoro, and one of $X^{12}$ can be deuterium. In some embodiments, two of $X^{12}$ can be fluoro, and one of $X^{12}$ can be an unsubstituted $C_{1-4}$ alkyl. Examples of $C_{1-4}$ alkyl groups include methyl, ethyl, n-propyl, iso-propyl, n-butyl, iso-butyl and tert-butyl. In some embodiments, two of $X^{12}$ can be chloro, and one of $X^{12}$ can be hydrogen. In some embodiments, two of $X^{12}$ can be chloro, and one of $X^{12}$ can be deuterium. In some embodiments, two of $X^{12}$ can be chloro, and one of $X^{12}$ can be an unsubstituted $C_{1-4}$ alkyl. Examples of $C_{1-4}$ alkyl groups include methyl, ethyl, n-propyl, iso-propyl, n-butyl, iso-butyl and tert-butyl.

In some embodiments of Formula (Iq), $R^{5J}$ can be hydrogen. In other embodiments, $R^{5J}$ can be deuterium. In still other embodiments, $R^{5J}$ can be an unsubstituted $C_{1-4}$ alkyl, such as, methyl, ethyl, n-propyl, iso-propyl, n-butyl, iso-butyl and tert-butyl.

In some embodiments of Formula (Iq), p14 can be 0. In other embodiments, each $X^P$ can be deuterium, and p14 can be 6. In still other embodiments, each $X^P$ can be deuterium, and p14 can be 5. In yet still other embodiments, each $X^P$ can be deuterium, and p14 can be 4. In some embodiments, each $X^P$ can be deuterium, and p14 can be 3. In other embodiments, each $X^P$ can be deuterium, and p14 can be 2. In still other embodiments, each $X^P$ can be deuterium, and p14 can be 1. In some embodiments, each $X^P$ can be chloro, and p14 can be 6. In other embodiments, each $X^P$ can be chloro, and p14 can be 5. In still other embodiments, each $X^P$ can be chloro, and p14 can be 4. In yet still other embodiments, each $X^P$ can be chloro, and p14 can be 3. In some embodiments, each $X^P$ can be chloro, and p14 can be 2. In other embodiments, each $X^P$ can be chloro, and p14 can be 1. In some embodiments, each $X^P$ can be fluoro, and p14 can be 6. In other embodiments, each $X^P$ can be fluoro, and p14 can be 5. In still other embodiments, each $X^P$ can be fluoro, and p14 can be 4. In yet still other embodiments, each $X^P$ can be fluoro, and p14 can be 3. In some embodiments, each $X^P$ can be fluoro, and p14 can be 2. In other embodiments, each $X^P$ can be fluoro, and p14 can be 1.

Formula (Ir)

In some embodiments, the compound, or pharmaceutically acceptable salt thereof, can be a compound of Formula (Ir), or pharmaceutically acceptable salt thereof, having the structure:

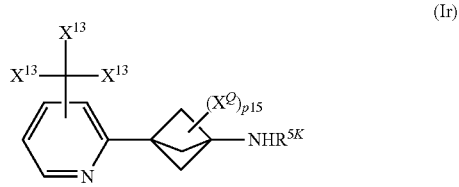

(Ir)

In some embodiments of Formula (Ir), each $X^{13}$ can be independently hydrogen, deuterium, an unsubstituted $C_{1-4}$ alkyl, fluoro or chloro, provided that at least two of $X^{13}$ is fluoro or chloro; $R^{5K}$ can be hydrogen, deuterium or an unsubstituted $C_{1-4}$ alkyl; each $X^Q$ can be independently deuterium, chloro or fluoro; and p15 can be independently 0, 1, 2, 3, 4, 5 or 6.

In some embodiments of Formula (Ir), each $X^{13}$ can be fluoro. In some embodiments, each $X^{13}$ can be chloro. In some embodiments, two of $X^{13}$ can be fluoro, and one of $X^{13}$ can be chloro. In some embodiments, two of $X^{13}$ can be chloro, and one of $X^{13}$ can be fluoro. In some embodiments, two of $X^{13}$ can be fluoro, and one of $X^{13}$ can be hydrogen. In some embodiments, two of $X^{13}$ can be fluoro, and one of $X^{13}$ can be deuterium. In some embodiments, two of $X^{13}$ can be fluoro, and one of $X^{13}$ can be an unsubstituted $C_{1-4}$ alkyl. Examples of $C_{1-4}$ alkyl groups include methyl, ethyl, n-propyl, iso-propyl, n-butyl, iso-butyl and tert-butyl. In some embodiments, two of $X^{13}$ can be chloro, and one of $X^{13}$ can be hydrogen. In some embodiments, two of $X^{13}$ can be chloro, and one of $X^{13}$ can be deuterium. In some embodiments, two of $X^{13}$ can be chloro, and one of $X^{13}$ can be an unsubstituted $C_{1-4}$ alkyl. Examples of $C_{1-4}$ alkyl groups include methyl, ethyl, n-propyl, iso-propyl, n-butyl, iso-butyl and tert-butyl.

In some embodiments of Formula (Ir), $R^{5K}$ can be hydrogen. In other embodiments, $R^{5K}$ can be deuterium. In still other embodiments, $R^{5K}$ can be an unsubstituted $C_{1-4}$ alkyl, for example, methyl, ethyl, n-propyl, iso-propyl, n-butyl, iso-butyl and tert-butyl.

In some embodiments of Formula (Ir), p15 can be 0. In other embodiments, each $X^Q$ can be deuterium, and p15 can be 6. In still other embodiments, each $X^Q$ can be deuterium, and p15 can be 5. In yet still other embodiments, each $X^Q$ can be deuterium, and p15 can be 4. In some embodiments, each $X^Q$ can be deuterium, and p15 can be 3. In other embodiments, each $X^Q$ can be deuterium, and p15 can be 2. In still other embodiments, each $X^Q$ can be deuterium, and p15 can be 1. In some embodiments, each $X^Q$ can be chloro, and p15 can be 6. In other embodiments, each $X^Q$ can be chloro, and p15 can be 5. In still other embodiments, each $X^Q$ can be chloro, and p15 can be 4. In yet still other embodiments, each $X^Q$ can be chloro, and p15 can be 3. In some embodiments, each $X^Q$ can be chloro, and p15 can be 2. In other embodiments, each $X^Q$ can be chloro, and p15 can be 1. In some embodiments, each $X^Q$ can be fluoro, and p15 can be 6. In other embodiments, each $X^Q$ can be fluoro, and p15 can be 5. In still other embodiments, each $X^Q$ can be fluoro, and p15 can be 4. In yet still other embodiments, each $X^Q$ can be fluoro, and p15 can be 3. In some embodiments, each $X^Q$ can be fluoro, and p15 can be 2. In other embodiments, each $X^Q$ can be fluoro, and p15 can be 1.

Formula (Is)

In some embodiments, the compound, or pharmaceutically acceptable salt thereof, can be a compound of Formula (Is), or pharmaceutically acceptable salt thereof, having the structure:

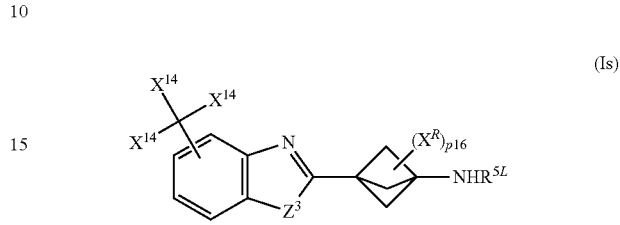

(Is)

In some embodiments of Formula (Is), each $X^{14}$ can be independently hydrogen, deuterium, an unsubstituted $C_{1-4}$ alkyl, fluoro or chloro, provided that at least two of $X^{14}$ is fluoro or chloro; $R^{5L}$ can be hydrogen, deuterium or an unsubstituted $C_{1-4}$ alkyl; each $X^R$ can be independently deuterium, chloro or fluoro; p16 can be independently 0, 1, 2, 3, 4, 5 or 6; and $Z^3$ can be nitrogen, oxygen or sulfur.

In some embodiments of Formula (Is), each $X^{14}$ can be fluoro. In some embodiments, each $X^{14}$ can be chloro. In some embodiments, two of $X^{14}$ can be fluoro, and one of $X^{14}$ can be chloro. In some embodiments, two of $X^{14}$ can be chloro, and one of $X^{14}$ can be fluoro. In some embodiments, two of $X^{14}$ can be fluoro, and one of $X^{14}$ can be hydrogen. In some embodiments, two of $X^{14}$ can be fluoro, and one of $X^{14}$ can be deuterium. In some embodiments, two of $X^{14}$ can be fluoro, and one of $X^{14}$ can be an unsubstituted $C_{1-4}$ alkyl. Examples of $C_{1-4}$ alkyl groups include methyl, ethyl, n-propyl, iso-propyl, n-butyl, iso-butyl and tert-butyl. In some embodiments, two of $X^{14}$ can be chloro, and one of $X^{14}$ can be hydrogen. In some embodiments, two of $X^{14}$ can be chloro, and one of $X^{14}$ can be deuterium. In some embodiments, two of $X^{14}$ can be chloro, and one of $X^{14}$ can be an unsubstituted $C_{1-4}$ alkyl. Examples of $C_{1-4}$ alkyl groups include methyl, ethyl, n-propyl, iso-propyl, n-butyl, iso-butyl and tert-butyl.

In some embodiments of Formula (Is), $R^{5L}$ can be hydrogen. In other embodiments, $R^{5L}$ can be deuterium. In still other embodiments, $R^{5L}$ can be an unsubstituted $C_{1-4}$ alkyl. Examples of $C_{1-4}$ alkyl groups include methyl, ethyl, n-propyl, iso-propyl, n-butyl, iso-butyl and tert-butyl.

In some embodiments of Formula (Is), p16 can be 0. In other embodiments, each $X^R$ can be deuterium, and p16 can be 6. In still other embodiments, each $X^R$ can be deuterium, and p16 can be 5. In yet still other embodiments, each $X^R$ can be deuterium, and p16 can be 4. In some embodiments, each $X^R$ can be deuterium, and p16 can be 3. In other embodiments, each $X^R$ can be deuterium, and p16 can be 2. In still other embodiments, each $X^R$ can be deuterium, and p16 can be 1. In some embodiments, each $X^R$ can be chloro, and p16 can be 6. In other embodiments, each $X^R$ can be chloro, and p16 can be 5. In still other embodiments, each $X^R$ can be chloro, and p16 can be 4. In yet still other embodiments, each $X^R$ can be chloro, and p16 can be 3. In some embodiments, each $X^R$ can be chloro, and p16 can be 2. In other embodiments, each $X^R$ can be chloro, and p16 can be 1. In some embodiments, each $X^R$ can be fluoro, and p16 can be 6. In other embodiments, each $X^R$ can be fluoro, and p16 can be 5. In still other embodiments, each $X^R$ can be fluoro, and p16 can be 4. In yet still other embodiments, each $X^R$ can be fluoro, and p16 can be 3. In some embodiments, each $X^R$ can be fluoro, and p16 can be 2. In other embodiments, each $X^R$ can be fluoro, and p16 can be 1.

In some embodiments of Formula (Is), $Z^3$ can be nitrogen. In other embodiments, $Z^3$ can be oxygen. In still other embodiments, $Z^3$ can be sulfur.

Formula (It)

In some embodiments, the compound, or pharmaceutically acceptable salt thereof, can be a compound of Formula (It), or pharmaceutically acceptable salt thereof, having the structure:

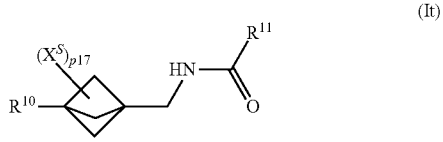

(It)

In some embodiments of Formula (It), $R^{10}$ can be selected from hydrogen, deuterium, halogen, hydroxy, an unsubstituted $C_{1-8}$ alkyl, an unsubstituted $C_{3-20}$ cycloalkyl and an unsubstituted $C_{1-8}$ haloalkyl; $R^{11}$ can be selected from hydrogen, deuerium, halogen, an unsubstituted $C_{1-30}$ alkyl, an unsubstituted $C_{2-30}$ alkenyl and an unsubstituted $C_{1-8}$ haloalkyl; each $X^S$ can be independently deuterium, chloro or fluoro; and p17 can be 0, 1, 2, 3, 4, 5 or 6.

In some embodiments of Formula (It), $R^{10}$ can be selected from hydrogen, deuterium, halogen, hydroxy, an unsubstituted $C_{1-8}$ alkyl, an unsubstituted $C_{3-20}$ cycloalkyl and an unsubstituted $C_{1-8}$ haloalkyl; $R^{11}$ can be selected from hydrogen, deuterium, halogen, an unsubstituted $C_{1-30}$ alkyl, an unsubstituted $C_{2-30}$ alkenyl and an unsubstituted $C_{1-8}$ haloalkyl; each $X^S$ can be independently deuterium, chloro or fluoro; and p17 can be 1, 2, 3, 4, 5 or 6.

In some embodiments of Formula (It), $R^{10}$ can be hydrogen. In other embodiments, $R^{10}$ can be deuterium. In still other embodiments, $R^{10}$ can be halogen, such as fluoro, chloro, bromo or iodo. In yet still other embodiments, $R^{10}$ can be hydroxy. In still other embodiments, $R^{10}$ can be an unsubstituted $C_{1-8}$ alkyl. Examples of suitable $C_{1-8}$ alkyl groups include methyl, ethyl, n-propyl, iso-propyl, n-butyl, iso-butyl, tert-butyl, pentyl (straight and branched), hexyl (straight and branched), heptyl (straight and branched) and octyl (straight and branched). In yet still other embodiments, $R^{10}$ can be an unsubstituted $C_{3-20}$ cycloalkyl. In even still other embodiments, $R^{10}$ can be an unsubstituted $C_{3-8}$ cycloalkyl. In some embodiments, $R^{10}$ can be an unsubstituted $C_{1-8}$ haloalkyl. Examples of suitable $C_{1-8}$ haloalkyls include, but are not limited to, $CF_3$, $CHF_2$, $CH_2F$, $CH_2CF_3$, $CH_2CHF_2$ and $CH_2CH_2F$.

In some embodiments of Formula (It), $R^{11}$ can be hydrogen. In other embodiments, $R^{11}$ can be deuterium. In still other embodiments, $R^{11}$ can be halogen, such as fluoro, chloro, bromo or iodo. In yet still other embodiments, $R^{11}$ can be an unsubstituted $C_{1-8}$ haloalkyl. Examples of suitable $C_{1-8}$ haloalkyls include, but are not limited to, $CF_3$, $CHF_2$, $CH_2F$, $CH_2CF_3$, $CH_2CHF_2$ and $CH_2CH_2F$.

When $R^{11}$ is an alkyl group, the number of carbon atoms of the alkyl group can vary. The alkyl group can be a long alkyl having 1 to 30 carbons, a medium alkyl having 1 to 12 carbon atoms or a lower alkyl having 1 to 6 carbon atoms. In some embodiments, $R^{11}$ can be an unsubstituted $C_{1-6}$ alkyl. In other embodiments, $R^{11}$ can be an unsubstituted $C_{2-6}$ alkyl. In still other embodiments, $R^{11}$ can be an unsubstituted $C_{1-8}$ alkyl. In still other embodiments, $R^{11}$ can be an unsubstituted $C_{1-12}$ alkyl. In yet still other embodiments, $R^{11}$ can be an unsubstituted $C_{1-30}$ alkyl. In some embodiments, $R^{11}$ can be an unsubstituted $C_{7-26}$ alkyl. In other embodiments, $R^{11}$ can be an unsubstituted $C_{12-26}$ alkyl. Examples of lower alkyl groups include methyl, ethyl, n-propyl, iso-propyl, n-butyl, iso-butyl, a tert-butyl, pentyl (straight and branched) and hexyl (straight and branched). Examples of suitable $C_{1-8}$ alkyl groups include methyl, ethyl, n-propyl, iso-propyl, n-butyl, iso-butyl, tert-butyl, pentyl (straight and branched), hexyl (straight and branched), heptyl (straight and branched) and octyl (straight and branched). Examples of unsubstituted $C_{1-30}$ alkyls include, but are not limited to, —$(CH_2)_6CH_3$, —$(CH_2)_8CH_3$, —$(CH_2)_{10}CH_3$, —$(CH_2)_{12}CH_3$, —$(CH_2)_{14}CH_3$, —$(CH_2)_{16}CH_3$, —$(CH_2)_{18}CH_3$, —$(CH_2)_{20}CH_3$, —$(CH_2)_{22}CH_3$ and —$(CH_2)_{24}CH_3$.

Similar to alkyls, alkenyls can be a long alkenyl having 2 to 30 carbons, a medium alkenyl having 2 to 12 carbon atoms or a lower alkenyl having 2 to 6 carbon atoms. In some embodiments, $R^{11}$ can be an unsubstituted $C_{2-30}$ alkenyl. In other embodiments, $R^{11}$ can be an unsubstituted $C_{2-16}$ alkenyl. In still other embodiments, $R^{11}$ can be an unsubstituted $C_{18}$ alkenyl. In yet still other embodiments, $R^{11}$ can be an unsubstituted $C_{20-30}$ alkenyl. Examples of unsubstituted $C_{2-30}$ alkenyls include, but are not limited to, —$(CH_2)_7CH$=$CH(CH_2)_3CH_3$, —$(CH_2)_7CH$=$CHCH_2CH$=$CH(CH_2)_4CH_3$, —$(CH_2)_7CH$=$CH(CH_2)_7CH_3$, —$(CH_2)_7CH$=$CHCH_2CH$=$CH(CH_2)_4CH_3$, —$(CH_2)_7CH$=$CH(CH_2)_7CH_3$, —$(CH_2)_7CH$=$CHCH_2CH$=$CHCH_2CH$=$CHCH_2CH_3$, —$(CH_2)_9CH$=$CH(CH_2)_5CH_3$, —$(CH_2)_3CH$=$CHCH_2CH$=$CHCH_2CH$=$CHCH_2CH$=$CH(CH_2)_4CH_3$, —$(CH_2)_{11}CH$=$CH(CH_2)_7CH_3$, —$(CH_2)_3CH$=$CHCH_2CH$=$CHCH_2CH$=$CHCH_2CH$=$CHCH_2CH$=$CHCH_2CH_3$, —$(CH_2)_4CH$=$CHCH(CH_3)_2$ and —$(CH_2)_2CH$=$CHCH_2CH$=$CHCH_2CH$=$CHCH_2CH$=$CHCH_2CH$=$CHCH_2CH_3$.

In some embodiments, $R^{11}$ can be the aliphatic tail of a saturated or an unsaturated fatty acid. As an example, $R^{11}$ can be the aliphatic tail of caprylic acid (HOO$\underline{C}$($CH_2$)$_6$$CH_3$). In this example of caprylic acid, the aliphatic tail is bolded and italicized. When the saturated or an unsaturated fatty acid becomes part of a compound of Formula (It), the carbon of the carboxylic acid of the saturated or an unsaturated fatty acid becomes the carbon of $\underline{C}$(O)$R^{11}$ that is bold and underlined. For example, when $R^{11}$ is the aliphatic tail of caprylic acid, the compound of Formula (It) can have the following structure:

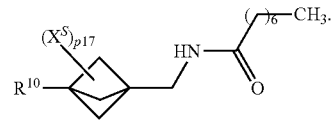

A non-limiting list of suitable saturated or an unsaturated fatty acids are myristoleic acid, palmitoleic, sapienic acid, linoleic acid, oleic acid, linoleiaidic acid, elaidic acid, alpha-linolenic acid, vaccenic acid, arachidonic acid, erucic acid, eicosapentaenoic acid, (E)-8-methylnon-6-enoic acid, docosahexaenoic acid, caprylic acid, capric acid, lauric acid, myristic acid, palmitic acid, stearic acid, arachidic acid, behenic acid, lignoceric acid and cerotic acid.

In some embodiments of Formula (It), p17 can be 0. In other embodiments, each $X^S$ can be deuterium, and p17 can be 6. In still other embodiments, each $X^S$ can be deuterium, and p17 can be 5. In yet still other embodiments, each $X^S$ can be deuterium, and p17 can be 4. In some embodiments, each $X^S$ can be deuterium, and p17 can be 3. In other embodiments, each $X^S$ can be deuterium, and p17 can be 2. In still other embodiments, each $X^S$ can be deuterium, and p17 can be 1. In some embodiments, each $X^S$ can be chloro, and p17 can be 6. In other embodiments, each $X^S$ can be chloro, and p17 can be 5. In still other embodiments, each $X^S$ can be chloro, and p17 can be 4. In yet still other embodiments, each $X^S$ can be chloro, and p17 can be 3. In some embodiments, each $X^S$ can be chloro, and p17 can be 2. In other embodiments, each $X^S$ can be chloro, and p17 can be 1. In some embodiments, each $X^S$ can be fluoro, and p17 can be 6. In other embodiments, each $X^S$ can be fluoro, and p17 can be 5. In still other embodiments, each $X^S$ can be fluoro, and p17 can be 4. In yet still other embodiments, each $X^S$ can be fluoro, and p17 can be 3. In some embodiments, each $X^S$ can be fluoro, and p17 can be 2. In other embodiments, each $X^S$ can be fluoro, and p17 can be 1.

In some embodiments of Formula (It), when p17 is 0, then $R^{10}$ cannot be hydrogen. In other embodiments, when p17 is 0, then $R^{10}$ cannot be deuterium. In still other embodiments, when p17 is 0, then $R^{10}$ cannot be halogen. In yet still other embodiments, when p17 is 0, then $R^{10}$ cannot be hydroxy. In some embodiments, when p17 is 0, then $R^{10}$ cannot be an unsubstituted $C_{1-8}$ alkyl. In other embodiments, when p17 is 0, then $R^{10}$ cannot be an unsubstituted $C_{3-20}$ cycloalkyl, or an unsubstituted $C_{3-8}$ cycloalkyl. In still other embodiments, when p17 is 0, then $R^{10}$ cannot be an unsubstituted $C_{1-8}$ haloalkyl. In some embodiments, when p17 is 0, then $R^{11}$ cannot be hydrogen. In other embodiments, when p17 is 0, then $R^{11}$ cannot be deuterium. In still other embodiments, when p17 is 0, then $R^{11}$ cannot be halogen. In some embodiments, when p17 is 0, then $R^{11}$ cannot be an unsubstituted $C_{1-30}$ alkyl, such as those described in this paragraph. In other embodiments, when p17 is 0, then $R^{11}$ cannot be an aliphatic tail of a saturated fatty acid. In some embodiments, when p17 is 0, then $R^{11}$ cannot be an unsubstituted $C_{2-30}$ alkenyl, such as those described in this paragraph. In other embodiments, when p17 is 0, then $R^{11}$ cannot be an aliphatic tail of an unsaturated fatty acid. In still other embodiments, when p17 is 0, then $R^{11}$ cannot be an unsubstituted $C_{1-8}$ haloalkyl. In some embodiments, $R^{10}$ cannot be hydrogen. In other embodiments, $R^{10}$ cannot be an unsubstituted $C_{1-6}$ alkyl. In still other embodiments, $R^{10}$ cannot be an unsubstituted $C_{3-10}$ cycloalkyl. In yet still other embodiments, $R^{10}$ cannot be halogen. In even still other embodiments, $R^{10}$ cannot be an unsubstituted $C_{1-8}$ haloalkyl. In some embodiments, $R^{11}$ cannot be an unsubstituted $C_{1-6}$ alkyl. In other embodiments, $R^{11}$ cannot be an unsubstituted $C_{1-8}$ haloalkyl. In still other embodiments, $R^{11}$ cannot be an unsubstituted $C_{17}$ alkenyl. In yet still other embodiments, $R^{11}$ cannot be an unsubstituted $C_{19}$ alkenyl. Examples of suitable halogen groups include fluoro, chloro, bromo and iodo. Examples of unsubstituted $C_{1-30}$ alkyls include, but are not limited to, $-(CH_2)_6CH_3$, $-(CH_2)_8CH_3$, $-(CH_2)_{10}CH_3$, $-(CH_2)_{12}CH_3$, $-(CH_2)_{14}CH_3$, $-(CH_2)_{16}CH_3$, $-(CH_2)_{18}CH_3$, $-(CH_2)_{20}CH_3$, $-(CH_2)_{22}CH_3$ and $-(CH_2)_{24}CH_3$. Examples of unsubstituted $C_{2-30}$ alkenyls include, but are not limited to, $-(CH_2)_7CH=CH(CH_2)_3CH_3$, $-(CH_2)_7CH=CHCH_2CH=CH(CH_2)_4CH_3$, $-(CH_2)_7CH=CH(CH_2)_7CH_3$, $-(CH_2)_7CH=CHCH_2CH=CH(CH_2)_4CH_3$, $-(CH_2)_7CH=CH(CH_2)_7CH_3$, $-(CH_2)_7CH=CHCH_2CH=CHCH_2CH=CHCH_2CH_3$, $-(CH_2)_9CH=CH(CH_2)_5CH_3$, $-(CH_2)_3CH=CH-CH_2CH=CHCH_2CH=CHCH_2CH=CH(CH_2)_4CH_3$, $-(CH_2)_{11}CH=CH(CH_2)_7CH_3$, $-(CH_2)_3CH=CHCH=CHCH_2CH=CHCH_2CH=CHCH_2$ $CH=CHCH_2$ $CH_3$, $-(CH_2)_4CH=CHCH(CH_3)_2$ and $-(CH_2)_2CH=CHCH_2CH=CHCH_2CH=CHCH_2CH=CHCH_2$ $CH=CHCH_2CH=CHCH_2CH_3$. Examples of suitable haloalkyl groups include, but are not limited to, chloromethyl, fluoromethyl, difluoromethyl, trifluoromethyl, 1-chloro-2-fluoromethyl and 2-fluoroisobutyl. Examples of suitable $C_{3-20}$ cycloalkyl groups include, but are not limited to, cyclopropyl, cyclobutyl, cyclopentyl, cyclohexyl, cycloheptyl and cyclooctyl. Examples of suitable $C_{1-8}$ alkyl groups include methyl, ethyl, n-propyl, iso-propyl, n-butyl, iso-butyl, tert-butyl, pentyl (straight and branched), hexyl (straight and branched), heptyl (straight and branched) and octyl (straight and branched). Examples of suitable $C_{17}$ alkenyl groups include, but are not limited to, $-(CH_2)_7$ $CH=CH(CH_2)_7CH_3$. Examples of suitable $C_{19}$ alkenyl groups include, but are not limited to, $-(CH_2)_3$ $CH=CHCH_2CH=CHCH_2CH=CHCH_2CH=CH(CH_2)_4$ $CH_3$. In some embodiments, a compound of Formula (It), or a pharmaceutically acceptable salt thereof, cannot one or more of the following compounds,

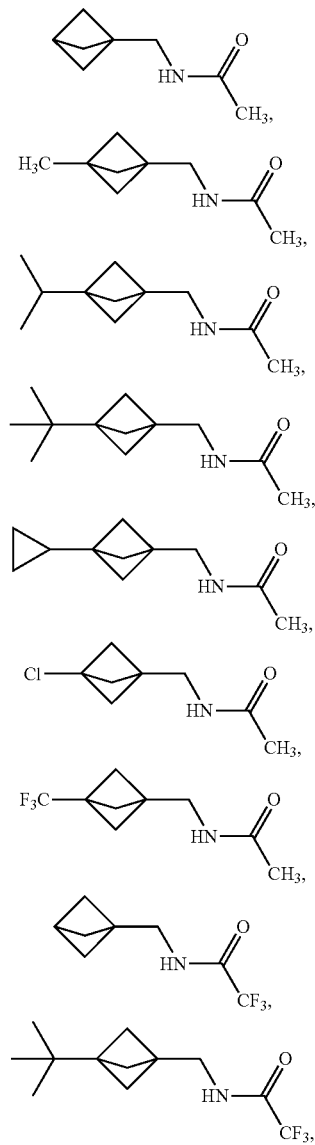

-continued

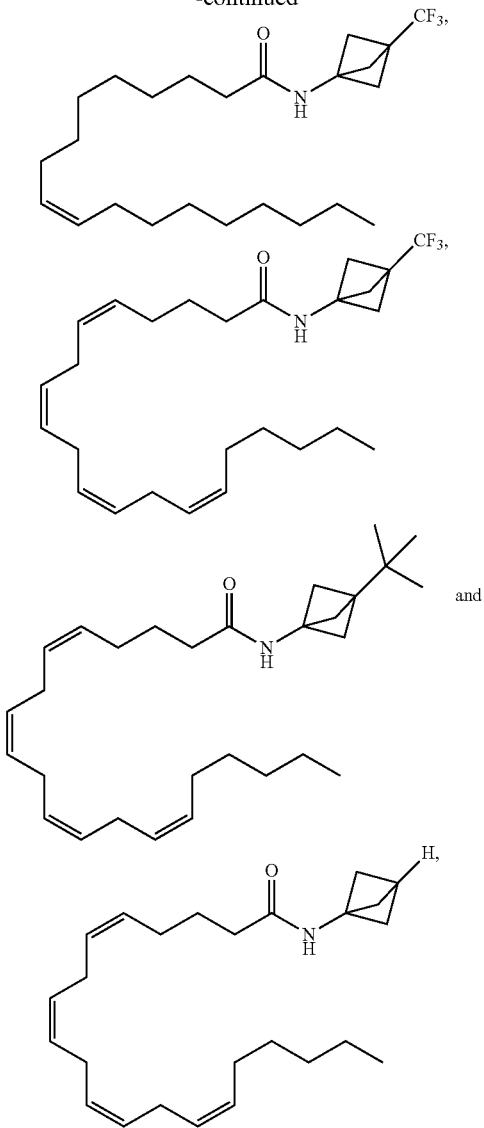

or a pharmaceutically acceptable salt of any of the foregoing.

In some embodiments of Formulae (Ia), (Ib), (Id), (If), (Ig), (Ih), (Ik), (Ip), (Ik), (Ir) and (Is), at least two of each of $X^1$, $X^2$, $X^3$, $X^4$, $X^5$, $X^6$, $X^7$, $X^{11}$, $X^{12}$, $X^{13}$ and $X^{14}$, respectively, cannot be fluoro. In other embodiments of Formulae (Ia), (Ib), (Id), (If), (Ig), (Ih), (Ik), (Ip), (Iq), (Ir) and (Is), three of each of $X^1$, $X^2$, $X^3$, $X^4$, $X^5$, $X^6$, $X^7$, $X^{11}$, $X^{12}$, $X^{13}$ and $X^{14}$, respectively, cannot be fluoro. In still other embodiments of Formulae (Ia), (Ib), (Id), (If), (Ig), (Ih), (Ik), (Ip), (Iq), (Ir) and (Is), at least two of each of $X^1$, $X^2$, $X^3$, $X^4$, $X^5$, $X^6$, $X^7$, $X^{11}$, $X^{12}$, $X^{13}$ and $X^{14}$, respectively, cannot be chloro. In yet still other embodiments of Formulae (Ia), (Ib), (Id), (If), (Ig), (Ih), (Ik), (Ip), (Iq), (Ir) and (Is), three of each of $X^1$, $X^2$, $X^3$, $X^4$, $X^5$, $X^6$, $X^7$, $X^{11}$, $X^{12}$, $X^{13}$ and $X^{14}$, respectively, cannot be chloro. In some embodiments of Formulae (Ia), (Ib), (Id), (If), (Ig), (Ih), (Ik), (Ip), (Iq), (Ir) and (Is), each of $X^1$, $X^2$, $X^3$, $X^4$, $X^5$, $X^6$, $X^7$, $X^{11}$, $X^{12}$, $X^{13}$ and $X^{14}$, respectively, are independently deuterium, an unsubstituted $C_{1-4}$ alkyl, fluoro or chloro, provided that at least two of each of $X^1$, $X^2$, $X^3$, $X^4$, $X^5$, $X^6$, $X^7$, $X^{11}$, $X^{12}$, $X^{13}$ and $X^{14}$, respectively, are fluoro or chloro. In other embodiments of Formulae (Ia), (Ib), (Id), (If), (Ig), (Ih), (Ik), (Ip), (Iq), (Ir) and (Is), each of $X^1$, $X^2$, $X^3$, $X^4$, $X^5$, $X^6$, $X^7$, $X^{11}$, $X^{12}$, $X^{13}$ and $X^{14}$, respectively, are independently hydrogen, deuterium, fluoro or chloro, provided that at least two of each of $X^1$, $X^2$, $X^3$, $X^4$, $X^5$, $X^6$, $X^7$, $X^{11}$, $X^{12}$, $X^{13}$ and $X^{14}$, respectively, are fluoro or chloro.

In some embodiments of Formulae (Ic), (Id), (Ie), (If), (Im), (In), (Io), (Ip), (Iq), (Ir) and (Is), each of $R^{5A}$, $R^{5B}$, $R^{5C}$, $R^{5D}$, $R^{5E}$, $R^{5F}$, $R^{5G}$, $R^{5H}$, $R^{5J}$, $R^{5K}$ and $R^{5L}$, respectively, cannot be hydrogen. In other embodiments of Formulae (Ic), (Id), (Ie), (If), (Im), (In), (Io), (Ip), (Iq), (Ir) and (Is), each of $R^{5A}$, $R^{5B}$, $R^{5C}$, $R^{5D}$, $R^{5E}$, $R^{5F}$, $R^{5G}$, $R^{5H}$, $R^{5J}$, $R^{5K}$ and $R^{5L}$, respectively, cannot be an unsubstituted $C_{1-4}$ alkyl, such as methyl, ethyl, n-propyl, iso-propyl, n-butyl, iso-butyl and tert-butyl.

In some embodiments of Formulae (Ia), (Ib), (Ic), (Id), (Ie), (If), (Ig), (Ih), (Ik), (Im), (In), (Io), (Ip), (Iq), (Ir), (Is) and (It), each of p1, p2, p3, p4, p5, p6, p7, p8, p9, p10, p11, p12, p13, p14, p15, p16 and p17, respectively, cannot be 0.

In some embodiments of Formula (Ie), when $R^{4a}$ is $-C(X^{16})_3$, then at least two of $X^{16}$ cannot be fluoro. In other embodiments of Formula (Ie), when $R^{4a}$ is $-C(X^{16})_3$, then $-C(X^{16})_3$ cannot be $-CF_3$. In still other embodiments of Formula (Ie), when $R^{4a}$ is $-C(X^{16})_3$, then at least two of $X^{16}$ cannot be chloro. In yet still other embodiments of Formula (Ie), when $R^{4a}$ is $-C(X^{16})_3$, then $-C(X^{16})_3$ cannot be $-CCl_3$. In some embodiments of Formula (Ie), when $R^{4b}$ is $-C(X^{16})_3$, then at least two of $X^{16}$ cannot be fluoro. In other embodiments of Formula (Ie), when $R^{4b}$ is $-C(X^{16})_3$, then $-C(X^{16})_3$ cannot be $-CF_3$. In still other embodiments of Formula (Ie), when $R^{4b}$ is $-C(X^{16})_3$, then at least two of $X^{16}$ cannot be chloro. In yet still other embodiments of Formula (Ie), when $R^{4b}$ is $-C(X^{16})_3$, then $-C(X^{16})_3$ cannot be $-CCl_3$.

In some embodiments of Formulae (Im), (In) and (Io), each $X^8$, each $X^9$ and $X^{10}$, respectively, can be deuterium or chloro. In other embodiments of Formulae (Im), (In) and (Io), each $X^8$, each $X^9$ and $X^{10}$, respectively, can be deuterium or fluoro. In still other embodiments, more than one of each $X^8$, each $X^9$ and $X^{10}$, respectively, is fluoro. For example, 2, 3, 4, or 5 of $X^8$, $X^9$ and $X^{10}$, respectively, is fluoro. In yet still other embodiments, more than one of each $X^8$, each $X^9$ and $X^{10}$, respectively, is chloro (such as 2, 3, 4, or 5 of $X^8$, $X^9$ and $X^{10}$, respectively, is chloro). In some embodiments, the rings to which $X^8$ and $X^9$ are respectively attached cannot be fully fluorinated. In other embodiments, the rings to which $X^8$ and $X^9$ are respectively attached cannot be fully chloronated. In some embodiments, $X^{10}$ cannot be fluoro. In other embodiments, $X^{10}$ cannot be chloro.

In some embodiments, the compound cannot be selected from:

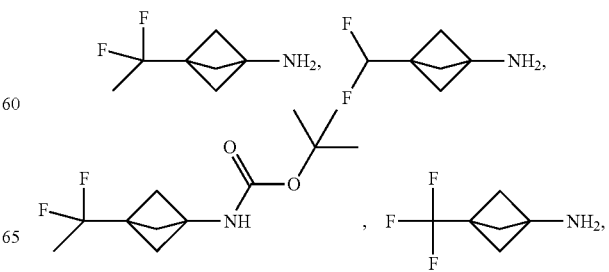

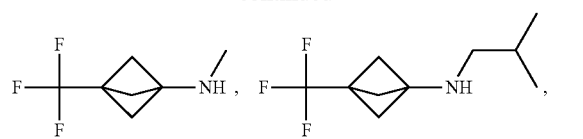
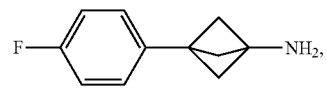
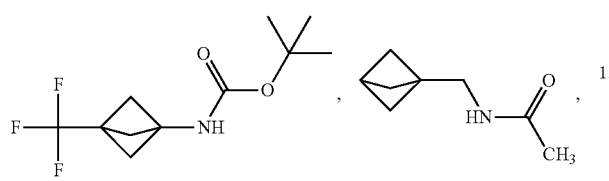
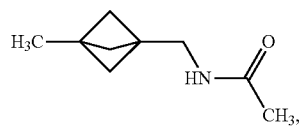
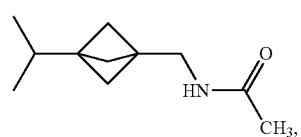
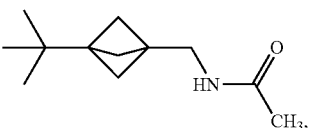
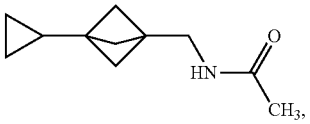
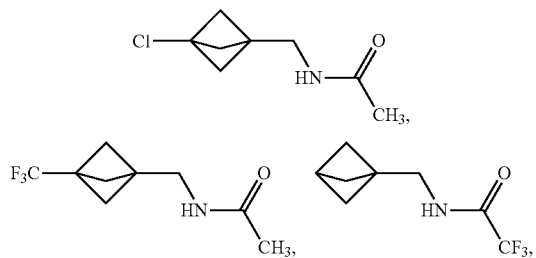
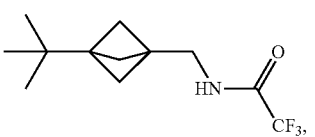
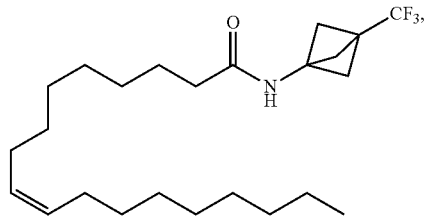

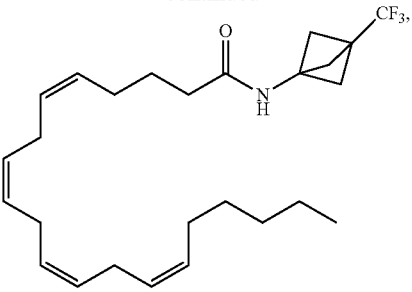
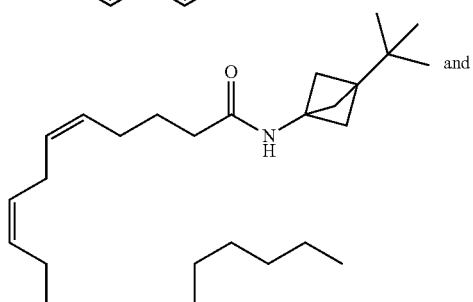

and

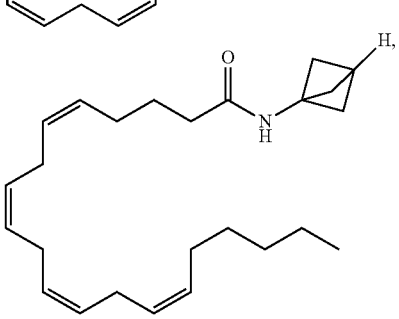

or a pharmaceutically acceptable salt of any of the foregoing.

Methods

The various compounds contemplated herein can be obtained from known starting materials by various routes known to those skilled in the art. Some suitable routes are illustrated in the Examples and following references: Radchenko et al., *Journal of Organic Chemistry* (2010) 75:5941-5952; U.S. Patent Publication No. 2008/0287468 (filed 11 Oct. 2007); WO 2002/059083 (filed 23 Oct. 2001); Nisato et al. *Journal of Heterocyclic Chemistry* (1985) 22:961-963; WO 2005/000810 (filed 22 Jun. 2004); WO 2007/036733 (filed 29 Sept. 2006); Lewin et al., *Journal of Medicinal Chemistry* (1998) 41:988-995; WO 2010/017047 (filed 27 Jul. 2009); WO 2013/033059 (filed 28 Aug. 2012). Salts can be formed using methods known to those skilled in the art and described herein, for example, reacting an amine with a suitable acid (such as HCl). In some embodiments, the pharmaceutically acceptable salt of a compound described herein (for example, a compound of Formulae (Ia), (Ib), (Ic), (Id), (Ie), (If), (Ig), (Ih), (Ik), (Im), (In), (Io), (Ip), (Iq), (Ir), (Is) and/or (It)) can be the HCl salt.

Pharmaceutical Compositions

Some embodiments described herein relate to a pharmaceutical composition, that can include an effective amount of one or more compounds described herein (for example, a compound of Formulae (Ia), (Ib), (Ic), (Id), (Ie), (If), (Ig), (Ih), (Ik), (Im), (In), (Io), (Ip), (Iq), (Ir), (Is) and/or (It), or pharmaceutically acceptable salts of any of the foregoing) and a pharmaceutically acceptable carrier, diluent, excipient or combination thereof.

The term "pharmaceutical composition" refers to a mixture of one or more compounds disclosed herein with other chemical components, such as diluents or carriers. The pharmaceutical composition facilitates administration of the compound to an organism. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, and salicylic acid. Pharmaceutical compositions will generally be tailored to the specific intended route of administration.

The term "physiologically acceptable" defines a carrier, diluent or excipient that does not abrogate the biological activity and properties of the compound nor cause appreciable damage or injury to an animal to which delivery of the composition is intended.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks appreciable pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the pH and isotonicity of human blood.

As used herein, an "excipient" refers to an essentially inert substance that is added to a pharmaceutical composition to provide, without limitation, bulk, consistency, stability, binding ability, lubrication, disintegrating ability etc., to the composition. A "diluent" is a type of excipient.

The pharmaceutical compositions described herein can be administered to a human patient per se, or in pharmaceutical compositions where they are mixed with other active ingredients, as in combination therapy, or carriers, diluents, excipients or combinations thereof. Proper formulation is dependent upon the route of administration chosen. Techniques for formulation and administration of the compounds described herein are known to those skilled in the art.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. Additionally, the active ingredients are contained in an amount effective to achieve its intended purpose. Many of the compounds used in the pharmaceutical combinations disclosed herein may be provided as salts with pharmaceutically compatible counterions.

Multiple techniques of administering a compound exist in the art including, but not limited to, oral, rectal, pulmonary, topical, aerosol, injection, infusion and parenteral delivery, including intramuscular, subcutaneous, intravenous, intramedullary injections, intrathecal, direct intraventricular, intraperitoneal, intranasal and intraocular injections.

One may also administer the compound in a local rather than systemic manner, for example, via injection or implantation of the compound directly into the affected area, often in a depot or sustained release formulation. Furthermore, one may administer the compound in a targeted drug delivery system, for example, in a liposome coated with a tissue-specific antibody. The liposomes will be targeted to and taken up selectively by the organ. For example, intranasal or pulmonary delivery to target a respiratory infection may be desirable.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions that can include a compound described herein formulated in a compatible pharmaceutical carrier may also be prepared, placed in an appropriate container, and labeled for treatment of an indicated condition.

Methods of Use

Some embodiments provided herein relate to a method of treating a disease or condition that can include administering to a subject an effective amount of a compound of Formulae (Ia), (Ib), (Ic), (Id), (Ie), (If), (Ig), (Ih), (Ik), (Im), (In), (Io), (Ip), (Iq), (Ir), (Is) and/or (It), or pharmaceutically acceptable salts of any of the foregoing. Other embodiments provided herein relate to a method of treating a disease or condition that can include contacting a cell in the central and/or peripheral nervous system of a subject with an effective amount of a compound of Formulae (Ia), (Ib), (Ic), (Id), (Ie), (If), (Ig), (Ih), (Ik), (Im), (In), (Io), (Ip), (Iq), (Ir), (Is) and/or (It), or pharmaceutically acceptable salts of any of the foregoing. In some embodiments, the subject can be at risk of developing a disease or condition that is responsive to acetaminophen and/or a NSAID. In some embodiments, the disease or condition can be one or more of the following: pain, fever, inflammation, ischemic injury (such as myocardial and/or cerebral) and/or neuronal injury. In some embodiments, the subject can be post-operative and has, or is believed to have or has actually developed post-operative pain. In some embodiments, the subject can be in need of treatment for acute pain and has, is believed to have or has actually developed acute pain. In some embodiments, the subject can be in need of treatment for chronic pain and has, is believed to have or has actually developed chronic pain. In some embodiments, the subject can be in need of treatment for neuropathic pain and has, is believed to have or has actually developed neuropathic pain. The basis for determining the need for treatment can be based on an underlying condition or conditions, from indication by the subject and/or on other bases known to practitioners. In some embodiments, a compound of Formulae (Ia), (Ib), (Ic), (Id), (Ie), (If), (Ig), (Ih), (Ik), (Im), (In), (Io), (Ip), (Iq), (Ir), (Is) and/or (It), or pharmaceutically acceptable salts of any of the foregoing, can be provided (such as administered) prophylactically, for example, prophylactically for pain (such as post-operative pain).

In some embodiments, a compound of Formulae (Ia), (Ib), (Ic), (Id), (Ie), (If), (Ig), (Ih), (Ik), (Im), (In), (Io), (Ip), (Iq), (Ir), (Is) and/or (It), or pharmaceutically acceptable salts of any of the foregoing, can contact a cell in the central nervous system, for example, the brain and/or spinal cord, and thereby treat a disease or condition described herein. In some embodiments, a compound of Formulae (Ia), (Ib), (Ic), (Id), (Ie), (If), (Ig), (Ih), (Ik), (Im), (In), (Io), (Ip), (Iq), (Ir), (Is) and/or (It), or pharmaceutically acceptable salts of any of the foregoing, can contact a cell in the peripheral nervous system, for example, the ganglia and/or nervous system outside the brain and spinal cord, and thereby treat a disease or condition described herein.

In some embodiments, a compound of Formulae (Ia), (Ib), (Ic), (Id), (Ie), (If), (Ig), (Ih), (Ik), (Im), (In), (Io), (Ip), (Iq), (Ir), (Is) and/or (It), or pharmaceutically acceptable salts of any of the foregoing, can contact a TRP (transient receptor potential) channels modulator (such as TRPV1 and/or TRPA1), and thereby treat a disease or condition described herein. In some embodiments, a compound of Formulae (Ia), (Ib), (Ic), (Id), (Ie), (If), (Ig), (Ih), (Ik), (Im), (In), (Io), (Ip), (Iq), (Ir), (Is) and/or (It), or pharmaceutically acceptable salts of any of the foregoing, can contact a cannabinoid receptors modulator (such as CB1 and/or CB2), and thereby treat a disease or condition described herein. In some embodiments, a compound of Formulae (Ia), (Ib), (Ic), (Id), (Ie), (If), (Ig), (Ih), (Ik), (Im), (In), (Io), (Ip), (Iq), (Ir), (Is) and/or (It), or pharmaceutically acceptable salts of any of the foregoing, can contact a serotonin receptor (for example, 5HT1, 5HT2, 5HT3, 5HT4, 5HT5, 5HT6 and/or 5HT7) and modulate its activity, and thereby treat a disease or condition described herein. In some embodiments, a compound of Formulae (Ia), (Ib), (Ic), (Id), (Ie), (If), (Ig), (Ih), (Ik), (Im), (In), (Io), (Ip), (Iq), (Ir), (Is) and/or (It), or pharmaceutically acceptable salts of any of the foregoing, can act as an anandamide reuptake inhibitor, and thereby treat a disease or condition described herein. In some embodiments, a compound of Formulae (Ia), (Ib), (Ic), (Id), (Ie), (If), (Ig), (Ih), (Ik), (Im), (In), (Io), (Ip), (Iq), (Ir), (Is) and/or (It), or pharmaceutically acceptable salts of any of the foregoing, can be a substrate for the fatty acid amide hydrolase (FAAH), and thereby treat a disease or condition described herein.

Some embodiments described herein generally relate to a method of treating pain of any etiology, including acute pain and chronic and neuropathic pain, and any pain in which acetaminophen is prescribed. Examples of pain include post-surgical pain; post-operative pain (including dental pain); migraine; headache and trigeminal neuralgia; pain associated with burn, wound and/or kidney stone; pain associated with trauma (including traumatic head injury); neuropathic pain (e.g., central and peripheral pain); pain associated with musculo- skeletal disorders; strains; sprains; contusions; fractures; myalgia; nociceptive pain (for example, rheumatoid arthritis and osteoarthritis pain); cystitis; visceral pain (such as, pancreatitis, inflammatory bowel disease and internal organ pain); ankylosing spondylitis; sero-negative (non-rheumatoid) arthropathies; non-articular rheumatism and peri-articular disorders; and mixed pain. Central pain includes post-stroke pain, pain associated with multiple sclerosis, spinal cord injury, migraine and HIV-related neuropathic pain. Peripheral pain includes postherpetic neuralgia and diabetic neuropathy. Mixed pain includes pain associated with cancer (including "breakthrough pain" and pain associated with terminal cancer), lower back and fibromyalgia. Examples of pain with an inflammatory component (in addition to some of those described above) include rheumatic pain, pain associated with mucositis and pain associated with dysmenorrhea. In some embodiments, a method and/or a composition described herein can be used for treating or preventing post-surgical pain. In some embodiments, a method and/or a composition described herein can be used for treating or preventing cancer pain or pain associated with a subject having cancer. In some embodiments, a method and/or a composition described herein can be used for treating or preventing osteoarthritis and/or rheumatoid arthritis pain. In some embodiments, a method and/or a composition described herein can be used for treating or preventing migraine pain. In some embodiments, a method and/or a composition described herein can be used for treating or preventing lower back pain and/or fibromyalgia pain. In some embodiments, a method and/or a composition described herein can be used for treating or preventing pain that is selected from pain associated with surgery, trauma, osteoarthritis, rheumatoid arthritis, lower back pain, fibromyalgia, postherpetic neuralgia, diabetic neuropathy, HIV-associated neuropathy and complex regional pain syndrome. Additionally information regarding pain is provided in Melnikova, I., "Pain market" (2010) 9(8):589-590, which is hereby incorporated by reference in its entirety.

In some embodiments, a compound of Formulae (Ia), (Ib), (Ic), (Id), (Ie), (If), (Ig), (Ih), (Ik), (Im), (In), (Io), (Ip), (Iq), (Ir), (Is) and/or (It), or pharmaceutically acceptable salts of any of the foregoing, can be used for treating or preventing pain and/or a fever (for example, in adults, children and/or infants, and in animal health to treat animals such as the cat, dog, or horse). As used herein, an "infant" is a human that is 1 year old or younger, a "child" is a human >1 to 17 years old, and an "adult" is a human 18 years or older. Compounds of Formulae (Ia), (Ib), (Ic), (Id), (Ie), (If), (Ig), (Ih), (Ik), (Im), (In), (Io), (Ip), (Iq), (Ir), (Is) and/or (It), or pharmaceutically acceptable salts of any of the foregoing, can be used to treat a variety and varying degrees of pain. In some embodiments, the pain can be acute pain (for example, acute pain following surgery, such as orthopedic surgery of adults, children, and/or infants). In some embodiments, the pain can be chronic pain (for example, pain lasting days, weeks, months, or years, and optionally following an initial event, such as an injury, trauma, surgery, or onset of disease).

In some embodiments, a compound of Formulae (Ia), (Ib), (Ic), (Id), (Ie), (If), (Ig), (Ih), (Ik), (Im), (In), (Io), (Ip), (Iq), (Ir), (Is) and/or (It), or pharmaceutically acceptable salts of any of the foregoing, can be used for treating and/or preventing a fever, such as endotoxin-induced fever (for example, endotoxin-induced fever in adults, children, and/or infants). In some embodiments, the fever can be selected from low-grade fever, moderate fever, high-grade fever and hyperpyrexia fever. In some embodiments, the fever can be selected from Pel-Ebstein fever, continuous fever, intermittent fever and remittent fever.

As described herein, compounds of Formulae (Ia), (Ib), (Ic), (Id), (Ie), (If), (Ig), (Ih), (Ik), (Im), (In), (Io), (Ip), (Iq), (Ir), (Is) and/or (It), or pharmaceutically acceptable salts of any of the foregoing, can be used in various subjects. In some embodiments, the subject can be a child and/or an infant, for example, a child or infant with a fever. In other embodiments, the subject can be an adult. In other embodiments, the subject can be an animal such as a cat, dog, or horse. As described herein, compounds of Formulae (Ia), (Ib), (Ic), (Id), (Ie), (If), (Ig), (Ih), (Ik), (Im), (In), (Io), (Ip), (Iq), (Ir), (Is) and/or (It), or pharmaceutically acceptable salts of any of the foregoing, can be administered by physicians and/or veterinarians as appropriate.

Some embodiments described herein relate to a method of delaying the onset of analgesia in a subject in need thereof, wherein the method can include administering to the subject an effective amount of Formulae (Ia), (Ib), (Ic), (Id), (Ie), (If), (Ig), (Ih), (Ik), (Im), (In), (Io), (Ip), (Iq), (Ir), (Is) and/or (It) , or pharmaceutically acceptable salts of any of the foregoing, that delays drug action by greater than 5 minutes, or 10 minutes, or 15 minutes, or 30 minutes, or 1 hour, or 2, hours, or 3 hours, or 4 hours, or 6 hours, or 8 hours, or 10 hours, or 12 hours, or 18 hours or 24 hours. Other embodiments described herein relate to a method of delaying the onset of analgesia in a subject in need thereof, wherein the method can include contacting a cell in the central and/or peripheral nervous system of a subject with an effective amount of Formulae (Ia), (Ib), (Ic), (Id), (Ie), (If), (Ig), (Ih), (Ik), (Im), (In), (Io), (Ip), (Iq), (Ir), (Is) and/or (It), or pharmaceutically acceptable salts of any of the foregoing, that delays drug action by greater than 5 minutes, or 10 minutes, or 15 minutes, or 30 minutes, or 1 hour, or 2, hours, or 3 hours, or 4 hours, or 6 hours, or 8 hours, or 10 hours, or 12 hours, or 18 hours or 24 hours.

In some embodiments, a compound of Formulae (Ia), (Ib), (Ic), (Id), (Ie), (If), (Ig), (Ih), (Ik), (Im), (In), (Io), (Ip), (Iq), (Ir), (Is) and/or (It), or pharmaceutically acceptable salts of any of the foregoing, may provide greater reduction or prevention of pain than acetaminophen in the early/acute phase (0-10 minutes). In some embodiments, a compound of Formulae (Ia), (Ib), (Ic), (Id), (Ie), (If), (Ig), (Ih), (Ik), (Im), (In), (Io), (Ip), (Iq), (Ir), (Is) and/or (It), or pharmaceutically acceptable salts of any of the foregoing, may provide greater reduction or prevention of pain than acetaminophen in the late/tonic phase (10-35 minutes).

As described herein, there can be a variety of advantages of using a compound described herein. Examples of such advantages include, but are not limited to, improved effectiveness, tolerance by a subject's body, inflammatory analgesic properties, osteoarthritis analgesic properties, incisional analgesic properties and neuropathic analgesic properties. Compounds described herein can have a longer metabolic half-life, for example, a longer metabolic half-life compared to APAP when both APAP and compounds described herein are administered by the same route and concentration. Additional advantage can include comparable or improved properties, such as those described herein, while minimizing and/or avoiding one or more side effects associated with NSAIDs, APAP and opioids. For example, a person of ordinary skill in the art would appreciate that the compounds described herein can avoid one or more undesirable side effects associated with inhibition of COX receptors and/or activation of opiate receptors, can have a lower likelihood for abuse or addiction compared to opioids, and can have a lower likelihood for loss of analgesic potency compared to opioids. Further advantages include lower dosages of compounds described herein, wherein the lower dosages achieves comparable or improved properties, such as inflammatory analgesic properties, osteoarthritis analgesic properties, incisional analgesic properties and/or neuropathic analgesic properties, compared to the same property achieved using a known NSAID, APAP or opioid. For example, a compound described herein can have comparable or improved osteoarthritis analgesic properties compared to a NSAID, such as celecoxib.

Furthermore, a person of ordinary skill in the art would appreciate that the compounds described would avoid many of the negative side effects associated with the NAPQI metabolite of acetaminophen. As described herein, acetaminophen can form the reactive metabolite, N-acetyl-p-benzoquinone imine (NAPQI), which is linked to liver toxicity. Acetaminophen is metabolically activated by cytochrome P450 enzymes to form NAPQI, and NAPQI depletes endogenous glutathione (GSH). The depletion of endogenous glutathione leaves cells vulnerable to oxidative damage. The formation of NAPQI is the result of the phenol or aniline ring of acetaminophen. Unlike acetaminophen, the compounds of the present application do not include a phenol or aniline ring and it is impossible to connect a substituent through a double bond (such as a carbonyl or imine group) at either end of bicyclo[1.1.1]pentane (i.e., at the 1 or 3 positions). As a result, one skilled in the art would not expect compounds described herein to form the reactive metabolite NAPQI.

As described herein, compounds of Formulae (Ia), (Ib), (Ic), (Id), (Ie), (If), (Ig), (Ih), (Ik), (Im), (In), (Io), (Ip), (Iq), (Ir), (Is) and/or (It), or pharmaceutically acceptable salts of any of the foregoing, can be administered by a variety of methods. In any of the methods described herein, administration can be by injection, infusion and/or intravenous administration over the course of 1 minute, 5 minutes, 10 minutes, 30 minutes, 1 hour, 2 hours, 6 hours, 12 hours, 24 hours or longer, or any intermediate time. Such administration can, in some circumstances, substitute for or significantly reduce the need for administration of an opiate. Some methods described herein can include intravenous administration to a subject in need thereof, for example, to a subject to manage post-operative or other acute or chronic pain, in either a bolus dose or by infusion over minutes, hours or days. Other methods described herein can include oral, intravenous, subcutaneous and/or intraperitoneal administration to a subject in need thereof, for example, to a subject to manage post-operative or other acute pain or chronic pain.

Other embodiments described herein relate to a method for selecting a therapy for managing or treating pain in a subject in need thereof, that can include evaluating whether the subject is at risk for hepatic toxicity from pain therapy, and selecting a therapy that includes a compound of Formulae (Ia), (Ib), (Ic), (Id), (Ie), (If), (Ig), (Ih), (Ik), (Im), (In), (Io), (Ip), (Iq), (Ir), (Is) and/or (It), or pharmaceutically acceptable salts of any of the foregoing, to reduce or eliminate such risk. The method can further include providing the selected therapy that includes a compound of Formulae (Ia), (Ib), (Ic), (Id), (Ie), (If), (Ig), (Ih), (Ik), (Im), (In), (Io), (Ip), (Iq), (Ir), (Is) and/or (It), or pharmaceutically acceptable salts of any of the foregoing, to the subject. In some embodiments, a compound of Formulae (Ia), (Ib), (Ic), (Id), (Ie), (If), (Ig), (Ih), (Ik), (Im), (In), (Io), (Ip), (Iq), (Ir), (Is) and/or (It), or pharmaceutically acceptable salts of any of the foregoing, can be of significant benefit in pain management in hospitals or other care facilities (for example, a nursing home).

As used herein, the terms "prevent" and "preventing," mean a subject does not experience and/or develop pain and/or fever. Examples of forms of prevention include prophylactic administration to a subject who is going to undergo surgery.

As used herein, the terms "treat," "treating," "treatment," "therapeutic," and "therapy" do not necessarily mean total cure or abolition of the disease or condition. Any alleviation of any undesired signs or symptoms of a disease or condition, to any extent can be considered treatment and/or therapy, for example the severity of the pain and/or fever is less compared to the severity of the pain and/or fever if the subject has not been administered/received the compound. Furthermore, treatment may include acts that may worsen the subject's overall feeling of well-being or appearance.

The terms "therapeutically effective amount" and "effective amount" are used to indicate an amount of an active compound, or pharmaceutical agent, that elicits the biological or medicinal response indicated. For example, a therapeutically effective amount of compound can be the amount needed to prevent, alleviate or ameliorate symptoms of disease or prolong the survival of the subject being treated. This response may occur in a tissue, system, animal or human and includes alleviation of the signs or symptoms of the disease being treated. Determination of an effective amount is well within the capability of those skilled in the art, in view of the disclosure provided herein. The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician. In cases of administration of a pharmaceutically acceptable salt, dosages may be calculated as the free base. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or conditions.

In general, however, a suitable dose will often be in the range of from about 0.15 mg/kg to about 100 mg/kg. For example, a suitable dose may be in the range from about 1 mg/kg to about 75 mg/kg of body weight per day, such as about 0.75 mg/kg to about 50 mg/kg of body weight of the recipient per day, about 1 mg/kg to 90 mg/kg of body weight of the recipient per day, or about 10 mg/kg to about 60 mg/kg of body weight of the recipient per day.

The compound may be administered in unit dosage form; for example, containing 1 to 2000 mg, 10 to 1000 mg or 5 to 500 mg of active ingredient per unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

As will be readily apparent to one skilled in the art, the useful in vivo dosage to be administered and the particular mode of administration will vary depending upon the age, weight, the severity of the affliction, and mammalian species treated, the particular compounds employed, and the specific use for which these compounds are employed. The determination of effective dosage levels, that is the dosage levels necessary to achieve the desired result, can be accomplished by one skilled in the art using routine methods, for example, human clinical trials, in vivo studies and in vitro studies. For example, useful dosages of compounds of Formulae (Ia), (Ib), (Ic), (Id), (Ie), (If), (Ig), (Ih), (Ik), (Im), (In), (Io), (Ip), (Iq), (Ir), (Is) and/or (It), or pharmaceutically acceptable salts thereof, can be determined by comparing their in vitro activity, and in vivo activity in animal models. Such comparison can be done against an established analgesic drug, such as acetaminophen.

Dosage amount and interval may be adjusted individually to provide plasma levels of the active moiety which are sufficient to maintain the modulating effects, or minimal effective concentration (MEC). The MEC will vary for each compound but can be estimated from in vivo and/or in vitro data. Dosages necessary to achieve the MEC will depend on individual characteristics and route of administration. However, HPLC assays or bioassays can be used to determine plasma concentrations. Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in animal health and veterinary medicine.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans Alternatively, the toxicity of particular compounds in an animal model, such as mice, rats, rabbits, dogs or monkeys, may be determined using known methods. The efficacy of a particular compound may be established using several recognized methods, such as in vitro methods, animal models, or human clinical trials. When selecting a model to determine efficacy, the skilled artisan can be guided by the state of the art to choose an appropriate model, dose, route of administration and/or regime.

Combination Drugs

One or more compounds of Formulae (Ia), (Ib), (Ic), (Id), (Ie), (If), (Ig), (Ih), (Ik), (Im), (In), (Io), (Ip), (Iq), (Ir), (Is) and/or (It), or pharmaceutically acceptable salts of any of the foregoing, can be provided alone or in combination with another drug(s). In some embodiments, the other drug(s) can be an opioid analgesic. Any of the known opioid analgesics can be combined with a compound of Formulae (Ia), (Ib), (Ic), (Id), (Ie), (If), (Ig), (Ih), (Ik), (Im), (In), (Io), (Ip), (Iq), (Ir), (Is) and/or (It), or pharmaceutically acceptable salts of any of the foregoing. As non-limiting examples, such opioid analgesics include morphine, codeine, hydrocodone, oxycodone, fentanyl, pethidine, methadone, pentazocine, sufentanil, levorphanol, dihydrocodeine, nalbuphine, butorphanol, tramadol, meptazinol, buprenorphine, dipipanone, alfentanil, remifentanil, oxymorphone, tapentadol, propoxyphene and hydromorphone.

In some embodiments, a compound of Formulae (Ia), (Ib), (Ic), (Id), (Ie), (If), (Ig), (Ih), (Ik), (Im), (In), (Io), (Ip), (Iq), (Ir), (Is) and/or (It), or pharmaceutically acceptable salts of any of the foregoing, can be provided in a dosage form (for example, an oral dosage form, an intravenous dosage form and/or an intraperitoneal dosage form), in combination with one of the following exemplary opioids: 1-20 mg hydrocodone (such as hydrocodone bitartrate), preferably 2.5 mg, 5 mg, 7.5 mg or 10 mg of hydrocodone or salt thereof; or 1-20 mg oxycodone, preferably 2.5 mg, 5 mg, 7.5 mg or 10 mg of oxycodone or salt thereof (such as the hydrochloride salt). In some embodiments, the amount of a compound of Formulae (Ia), (Ib), (Ic), (Id), (Ie), (If), (Ig), (Ih), (Ik), (Im), (In), (Io), (Ip), (Iq), (Ir), (Is) and/or (It), or pharmaceutically acceptable salts of any of the foregoing, can be in the range of about 20 to about 2000 mg, for example 20 ±0.5 to 2000 ±5 mg.

In some embodiments, a compound of Formulae (Ia), (Ib), (Ic), (Id), (Ie), (If), (Ig), (Ih), (Ik), (Im), (In), (Io), (Ip), (Iq), (Ir), (Is) and/or (It), or pharmaceutically acceptable salts of any of the foregoing, can be combined with one or more non-steroidal anti-inflammatory drugs (NSAIDs). As non-limiting examples, such NSAIDs include celecoxib, ketorolac, ketoprofen, indomethacin, sulindac, etodolac, mefenamic acid, meclofenamic acid, meclofenamate sodium, flufenamic acid, tolmetin, diclofenac, diclofenac sodium, ibuprofen, naproxen, naproxen sodium, fenoprofen, flurbiprofen, oxaprozin, piroxicam, meloxicam, ampiroxicam, droxicam, lornoxicam, cinnoxicam, sudoxicam, and tenoxicam, and pharmaceutically acceptable salts of the foregoing. In some embodiments, an NSAID can be a COX-2 inhibitor.

In some embodiments, a compound of Formulae (Ia), (Ib), (Ic), (Id), (Ie), (If), (Ig), (Ih), (Ik), (Im), (In), (Io), (Ip), (Iq), (Ir), (Is) and/or (It), or pharmaceutically acceptable salts of any of the foregoing, can be provided in a dosage form (for example, an oral dosage form, an intravenous dosage form and/or an intraperitoneal dosage form), in combination with one of the following exemplary NSAIDs: 10-1000 mg ibuprofen, for example 100 mg, 250 mg, 500 mg or 750 mg of ibuprofen or salt thereof; 100-1000 mg naproxen, for example 100 mg, 250 mg, 500 mg or 750 mg of naproxen or salt thereof (such as the sodium salt); 100-1000 mg ketorolac, for example 100 mg, 250 mg, 500 mg or 750 mg of ketorolac or salt thereof; 100-1000 mg ketoprofen, for example 100 mg, 250 mg, 500 mg or 750 mg of ketoprofen or salt thereof; or 10-1000 mg celecoxib, for example 100 mg, 250 mg, 500 mg or 750 mg of celecoxib or salt thereof. In some embodiments, the amount of a compound of Formulae (Ia), (Ib), (Ic), (Id), (Ie), (If), (Ig), (Ih), (Ik), (Im), (In), (Io), (Ip), (Iq), (Ir), (Is) and/or (It), or pharmaceutically acceptable salts of any of the foregoing, can be in the range of about 20 to about 2000 mg, for example 20 ±0.5 to 2000 ±5 mg.

Other combinations include combination of a compound of Formulae (Ia), (Ib), (Ic), (Id), (Ie), (If), (Ig), (Ih), (Ik), (Im), (In), (Io), (Ip), (Iq), (Ir), (Is) and/or (It), or pharmaceutically acceptable salts of any of the foregoing, with butalbital, codeine, dihydrocodeine, and/or aspirin. The other drug(s) can be provided using routes known to those skilled in the art and/or described herein. In some embodiments, a compound of Formulae (Ia), (Ib), (Ic), (Id), (Ie), (If), (Ig), (Ih), (Ik), (Im), (In), (Io), (Ip), (Iq), (Ir), (Is) and/or (It), or pharmaceutically acceptable salts of any of the foregoing, and another drug(s) can be provided in the same dosage form. In other embodiments, a compound of Formulae (Ia), (Ib), (Ic), (Id), (Ie), (If), (Ig), (Ih), (Ik), (Im), (In), (Io), (Ip), (Iq), (Ir), (Is) and/or (It), or pharmaceutically acceptable salts of any of the foregoing, and another drug(s) can be provided in the separate dosage forms. In some embodiments, a compound of Formulae (Ia), (Ib), (Ic), (Id), (Ie), (If), (Ig), (Ih), (Ik), (Im), (In), (Io), (Ip), (Iq), (Ir), (Is) and/or (It), or pharmaceutically acceptable salts of any of the foregoing, and another drug(s) can be by the same route (for example, both intravenously) or by different routes (for example, one orally and the other intraperitoneally). In some embodiments, a compound of Formulae (Ia), (Ib), (Ic), (Id), (Ie), (If), (Ig), (Ih), (Ik), (Im), (In), (Io), (Ip), (Iq), (Ir), (Is) and/or (It), or pharmaceutically acceptable salts of any of the foregoing, can be provided before another drug(s) (such as an opiate). In other embodiments, a compound of Formulae (Ia), (Ib), (Ic), (Id), (Ie), (If), (Ig), (Ih), (Ik), (Im), (In), (Io), (Ip), (Iq), (Ir), (Is) and/or (It), or pharmaceutically acceptable salts of any of the foregoing, can be provided simultaneously with another drug(s) (such as an opiate). In still other embodiments, a compound of Formulae (Ia), (Ib), (Ic), (Id), (Ie), (If), (Ig), (Ih), (Ik), (Im), (In), (Io), (Ip), (Iq), (Ir), (Is) and/or (It), or pharmaceutically acceptable salts of any of the foregoing, can be provided after another drug(s) (such as an opiate).

In some embodiments, a combination of a compound of Formulae (Ia), (Ib), (Ic), (Id), (Ie), (If), (Ig), (Ih), (Ik), (Im), (In), (Io), (Ip), (Iq), (Ir), (Is) and/or (It), or pharmaceutically acceptable salts of any of the foregoing, and an opioid analgesic can synergistically relieve pain. In some embodiments, the synergistic relief of pain can reduce opioid use. Some embodiments disclosed herein relate to a method of managing, treating and/or reducing pain that can include administering an effective amount of a combination of a compound of Formulae (Ia), (Ib), (Ic), (Id), (Ie), (If), (Ig), (Ih), (Ik), (Im), (In), (Io), (Ip), (Iq), (Ir), (Is) and/or (It), or pharmaceutically acceptable salts of any of the foregoing, and an opioid analgesic to a subject. Some embodiments disclosed herein relate to a method for reducing opioid use in pain management, that can include administering an amount of a compound of Formulae (Ia), (Ib), (Ic), (Id), (Ie), (If), (Ig), (Ih), (Ik), (Im), (In), (Io), (Ip), (Iq), (Ir), (Is) and/or (It), or pharmaceutically acceptable salts of any of the foregoing, in combination with an amount of an opioid analgesic, wherein the amount of the opioid analgesic in the combination is less than the amount of opioid analgesic needed to achieve approximately the same level of pain management when the opioid analgesic is administered alone. Methods known for evaluating pain management is known to those skilled in the art, for example, pain assessment tools. Some embodiments disclosed herein relate to a method for decreasing the risk of opioid dependency that can include administering an amount of a compound of Formulae (Ia), (Ib), (Ic), (Id), (Ie), (If), (Ig), (Ih), (Ik), (Im), (In), (Io), (Ip), (Iq), (Ir), (Is) and/or (It), or pharmaceutically acceptable salts of any of the foregoing, in combination with an amount of an opioid analgesic, wherein the amount of the opioid analgesic in the combination is less than the amount of opioid analgesic needed to achieve approximately the same level of pain management when the opioid analgesic is administered alone. Some embodiments disclosed herein relate to a method for treating pain and/or fever along with treating opioid dependency that can include administering an amount of a compound of Formulae (Ia), (Ib), (Ic), (Id), (Ie), (If), (Ig), (Ih), (Ik), (Im), (In), (Io), (Ip), (Iq), (Ir), (Is) and/or (It), or pharmaceutically acceptable salts of any of the forgoing, in combination with an amount of an opioid analgesic.

Examples

Additional embodiments are disclosed in further detail in the following examples, which are not in any way intended to limit the scope of the claims.

Compounds

The compounds of Formula (Ia), (Ib), (Ic), (Id), (Ie), (If), (Ig), (Ih), (Ik), (Im), (In), (Io), (Ip), (Iq), (Ir), (Is) and (It), and pharmaceutically acceptable salts of any of the foregoing, are provided illustrated in Table 1 can be prepared in various ways, including those techniques described herein and/or known to those skilled in the art as guided by the details provided herein. For example, the compounds of Formula (Ia), (Ib), (Ic), (Id), (Ie), (If), (Ig), (Ih), (Ik), (Im), (In), (Io), (Ip), (Iq), (Ir), (Is) and (It), and pharmaceutically acceptable salts of any of the foregoing, illustrated in Table 1 can be prepared as described in the Examples below. Those skilled in the art will understand that a number of structures shown in Table 1 are not stereospecific and/or are depicted as having unfilled valencies, and thus are generic to isotopic and/or stereochemical variants, including racemates, diastereomers, enantiomers and/or deuterated versions, which can be prepared in accordance with the guidance provided herein.

TABLE 1

| No. | Compound Structure |
|---|---|
| 1 | 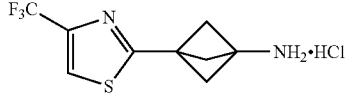 |
| 2 | 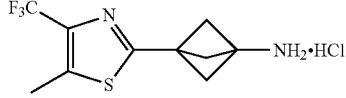 |
| 3 | 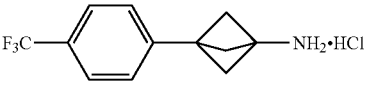 |
| 4 | 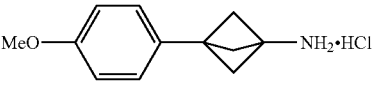 |
| 5 | 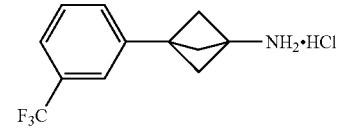 |
| 6 | 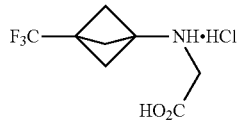 |
| 7 | 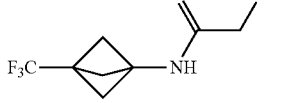 |
| 8 | 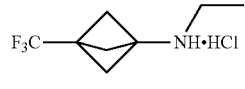 |
| 9 | 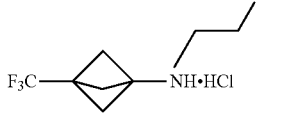 |
| 10 | 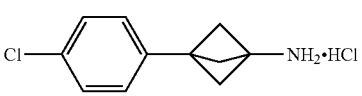 |
| 11 | 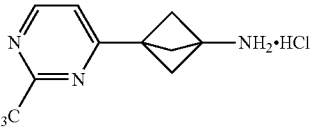 |
| 12 | 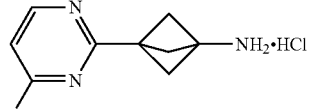 |
| 13 | 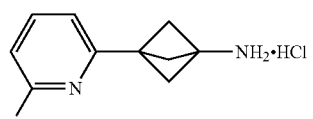 |
| 14 | 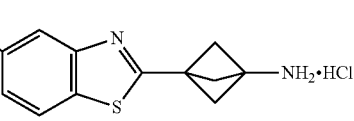 |
| 15 | 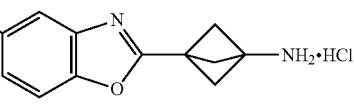 |
| 16 | 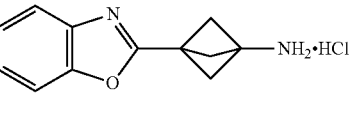 |
| 17 | 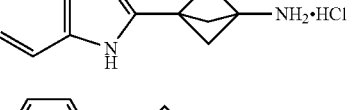 |
| 18 | 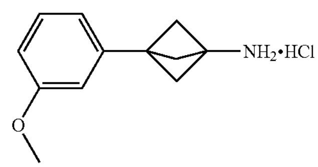 |
| 19 | 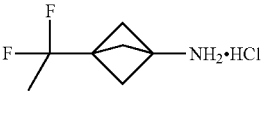 |
| 20 | 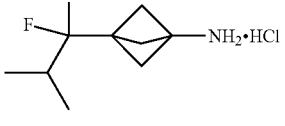 |
| 21 | 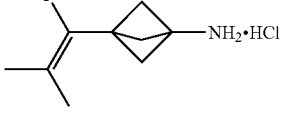 |
| 22 | 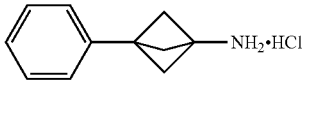 |

TABLE 1-continued

| No. | Compound Structure |
|---|---|
| 23 | 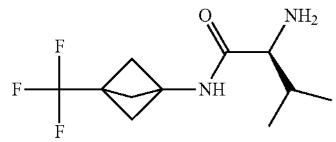 [SMILES: CC(C)[C@H](N)C(=O)NC12CC(C(F)(F)F)(C1)C2] |
| 24 | 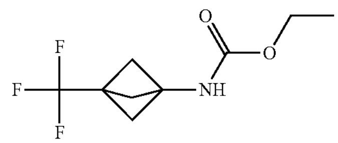 |
| 25 | 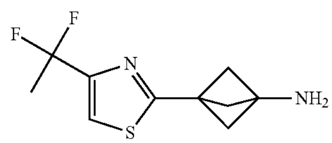 |
| 26 | 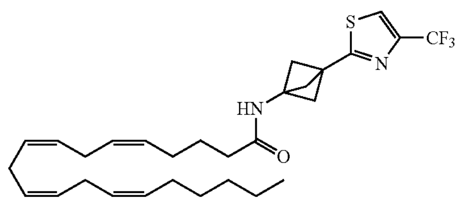 [SMILES: CCCCC/C=C\C/C=C\C/C=C\C/C=C\CCCC(=O)NC12CC(c3nc(C(F)(F)F)cs3)(C1)C2] |
| 27 | 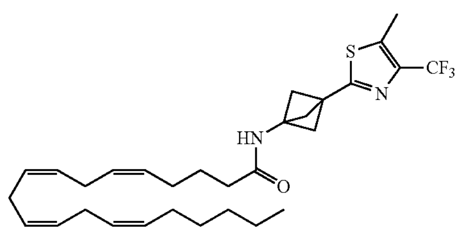 [SMILES: CCCCC/C=C\C/C=C\C/C=C\C/C=C\CCCC(=O)NC12CC(c3nc(C(F)(F)F)c(C)s3)(C1)C2] |

Example 1

3-(4-(Trifluoromethyl)thiazol-2-yl)bicyclo[1.1.1]pentan-1-amine hydrochloride (1)

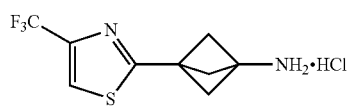

3-(Methoxycarbonyl)bicyclo-[1.1.1]pentane-1-carboxylic acid (70.0 g, 411 mmol) was added to a dry 1L $R_B$ F and dissolved in 400 mL DCM under $N_2$. Oxalyl chloride (34.8 mL, 411 mmol) was added followed by 1 drop of dry DMF. The reaction was stirred overnight at room temperature (rt) where it was determined to be complete by NMR. The solvent was removed in vacuo. 100 mL of dry toluene was added and removed in vacuo. Methyl 3-(chlorocarbonyl)bicyclo[1.1.1]pentane-1-carboxylate (78.0 g, 411 mmol) was dissolved in a total of 400 mL DCM and transferred to an addition funnel via cannula. 200 mL DCM was added under $N_2$ to a dry 2L $R_B$ F. The DCM was cooled to 0° C. and $NH_3$ was bubbled through the solution for 10 minutes. The DCM solution of methyl 3-(chlorocarbonyl)bicyclo[1.1.1]pentane-1-carboxylate was added slowly to the DCM $NH_3$ solution. $NH_3$ was bubbled through the suspension during the addition and for 30 minutes after the addition was complete. The ice bath was removed and the reaction was stirred for 2h where it was determined to be complete by NMR. The solvent was removed and the solid was stirred in 600 mL $Et_2O$ for 1 h and then filtered. The solid was dried to give 60.9g (88%) of methyl 3-carbamoylbicyclo[1.1.1]pentane-1-carboxylate 1-1 as a white solid. $^1$H NMR (400 MHz, DMSO-$d_6$) δ 7.36 (s, 1H), 7.03 (s, 1H), 3.60 (s, 3H), 2.12 (s, 6H).

Compound 1-1 (35.0 g, 207 mmol) was suspended in 400 mL THF. Phosphorus pentasulfide (22.9 g, 103 mmol) was added and the reaction was stirred for 12h where it was determined to be complete by crude NMR. The solid was removed by filtration. The precipitate was re-suspended in THF and filtered again. The filtrate was concentrated and the residue was absorbed onto Florisil® and purified by flash chromatography (SiO$_2$, EtOAc:Hexanes) to afford an off white solid. The solid was suspended in $Et_2O$ with stirring, filtered and dried under high vacuum to afford 19g (49%) of carbamothioylbicyclo-[1.1.1]pentane-1-carboxylate 1-2 as a white solid. LC/MS (APCI) m/z 186.0 [$C_8H_{11}NO_2S$+H]$^+$.

Compound 1-2 (5.11 g, 27.6 mmol) and NaHCO$_3$ (6.95 g, 83 mmol) was suspended in 20 mL EtOH. 3-Bromo-1,1,1-trifluoropropan-2-one (7.90 g, 41 4 mmol) in 20 mL EtOH was added and the reaction was stirred at 80° C. for 2 h where the reaction was determined to be complete by LCMS. The solvent was removed and the residue was partitioned between 75 mL water and 75 mL EtOAc. The layers were separated and the water layer was extracted with EtOAc (2×75 mL). The combined organics were dried (Na$_2$SO$_4$) and concentrated to give methyl 3-(imino((3,3,3-trifluoro-2-oxopropyl)thio)methyl)bicyclo[1.1.1]pentane-1-carboxylate 1-3 as an off white solid.

Compound 1-3 (8.15 g, 27 6 mmol) was dissolved in 40 mL DCM and Et$_3$N (7.69 mL, 55.2 mmol) was added under N$_2$. The flask was cooled to 0° C. and TFAA (4.99 mL, 35.9 mmol) was added dropwise. The bath was removed and the reaction was stirred to rt over 2 h where it was determined to be complete by LCMS. The reaction was concentrated and dissolved in 150 mL EtOAc. The organic layer was washed with saturated NaHCO$_3$ (1×100 mL), brine (1×100 mL), and dried (Na$_2$SO$_4$). The solvent was removed to give 8 g of an orange solid. The compound was recrystallized from 50 mL of heptane to give 6.12 g (80%) of methyl 3-(4-(trifluoromethyl)thiazol-2-yl)bicyclo[1.1.1]pentane-1-carboxylate 1-4 as an off white solid. LC/MS (APCI) m/z 278.0 [$C_{11}H_{10}F_3NO_2S$+H]$^+$.

Compound 1-4 (6.10 g, 22.0 mmol) was dissolved in 22 mL THF followed by 22 mL 2M NaOH. The reaction was stirred for 2 h where it was determined to be complete by LCMS. The THF was removed and the solution was cooled to 0° C. and the pH was adjusted to ~3 with 2M HCl. The mixture was allowed to stand in the refrigerator overnight and then filtered. The off-white solid was dissolved in EtOAc, dried (Na$_2$SO$_4$), and the solvent removed. The compound was dried overnight under high vacuum to give 5.19 g (90%) of 3-(4-(trifluoromethyl)thiazol-2-yl)bicyclo[1.1.1]pentane-1-carboxylic acid 1-5 as an off white solid. LC/MS (APCI) m/z 264.0 [$C_{10}H_8F_3NO_2S$+H]$^+$.

Compound 1-5 (5.19 g, 19.7 mmol) was dissolved in 66 mL of a 1:1 ratio of toluene:t-BuOH. Et$_3$N (5.50 mL, 39.4 mmol) and DPPA (4.67 mL, 21 7 mmol) were added under N$_2$. The reaction was stirred for 1 h and 8 g of 4 Å molecular sieves were added. The reaction was stirred for 3 h at rt and then stirred at 100° C. overnight. The reaction was cooled to rt and filtered through Celite rinsing with EtOAc. The solvent was removed until the compound was an off-white solid. The compound was dissolved in 80 mL EtOAc and washed with saturated NH₄Cl (50 mL), saturated NaHCO₃ (50 mL), brine (50 mL) and dried (Na₂SO₄). The solvent was removed to give 6.6 g of a beige solid that was suspended in 90 mL heptane and heated gently until all of the solid dissolved. The solution was carefully boiled down to reduce the solvent volume. Upon cooling, the solid was removed by filtration. The compound was dried under high vacuum overnight to give 5.89 g (89%) of tert-butyl (3-(4-(trifluoromethyl)thiazol-2-yl)bicyclo[1.1.1]pentan-1-yl)carbamate 1-6 as an off-white solid. LC/MS (APCI) m/z 335.1 $[C_{14}H_{17}F_3N_2O_2S+H]^+$.

Compound 1-6 (5.52 g, 16.5 mmol) was dissolved in 25 mL DCM. TFA (12.6 mL, 165 mmol) was added via syringe and the reaction was stirred for 1.5 h where it was determined to be complete by LCMS. The reaction was concentrated and 12 mL of 2M HCl in Et₂O was added. The mixture was stirred for 5 minutes and then the solvent was removed. The HCl addition was repeated two times. HCl (2N in Et₂O, 12 mL) was added followed by 20 mL Et₂O. The mixture was stirred vigorously and filtered. The solid was dried in the high vacuum oven overnight to give 4 g of an off white solid. The compound was dissolved in 10 mL of EtOH and approximately 5 mL of EtOH was boiled away. The mixture was cooled to rt and the resulting crystals were filtered and rinsed with MTBE. The compound was dried overnight under high vacuum to give 3.41 g (76%) of Compound 1 as a white solid. ¹H NMR (400 MHz, DMSO-d₆) δ 9.03 (s, 3H), 8.49-8.48 (s, 1H) 2.46 (s, 6H); LC/MS (APCI) m/z 235.0 $[C_9H_9F_3N_2S+H]^+$.

Example 2

3-(5-Methyl-4-(trifluoromethyl)thiazol-2-yl)bicyclo[1.1.1]pentan-1-amine hydrochloride (2)

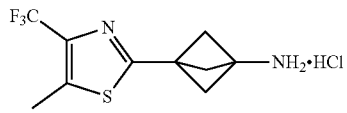

A suspension of methyl 3-carbamothioylbicyclo[1.1.1]pentane-1-carboxylate (8.45 g, 45.6 mmol) and NaHCO₃ (5.75 g, 68 4 mmol) in anhydrous EtOH (45.6 mL) was treated with 3-bromo-1,1,1-tributan-2-one (16.7 mL, 137 mmol). The resulting suspension was heated to 80° C. until complete (~2 h). The mixture was cooled to rt and concentrated to afford the crude intermediate as a semi-solid. The crude methyl 3-(imino((4,4,4-trifluoro-3-oxobutan-2-yl)thio)methyl)bicyclo[1.1.1]pentane-1-carboxylate was dissolved in anhydrous DCM (76 mL), cooled to 0° C. and treated with Et₃N (12.7 mL, 91.0 mmol) and TFAA (8.38 mL, 59.3 mmol). The resulting solution was stirred at rt. After stiffing overnight, additional Et₃N (6.36 mL, 45.6 mmol) and TFAA (6.44 mL, 45.6 mmol) was added and stiffing was continued for 2.5 h. 1N HCl (100 mL) was added and the mixture was extracted with DCM (4×100 mL). The combined organics were dried (Na₂SO₄) and concentrated to provide the crude product which was further purified by flash chromatography (SiO₂, EtOAc/Hexanes) to afford 13.3 g (97%) of methyl 3-(5-methyl-4-(trifluoromethyl)thiazol-2-yl)bicyclo[1.1.1]pentane-1-carboxylate 2-1 as a yellow oil. LC/MS (APCI) m/z 292.0 $[C_{12}H_{12}F_3NO_2S+H]^+$.

A solution of Compound 2-1 (13.3 g, 45.6 mmol) in THF (73.0 mL) and water (18.2 mL) was treated with LiOH.H₂O (4.21 g, 100 mmol) and allowed to stir at rt until complete (1 h). The solution was concentrated to ⅓ of the original volume, diluted with water (50 mL) and washed with Et₂O (50 mL). The aqueous layer was acidified with 1N HCl then extracted with EtOAc (4×100 mL). The combined organic layers were dried (Na₂SO₄) and concentrated to provide 11.7 g (92%) of 3-(5-methyl-4-(trifluoromethyl)thiazol-2-yl)bicyclo[1.1.1]pentane-1-carboxylic acid 2-2 as a white solid. LC/MS (APCI) m/z 278.0 $[C_{11}H_{10}F_3NO_2S+H]^+$.

A solution of Compound 2-2 (11.6 g, 41.8 mmol) in anhydrous toluene (105 mL) and tert-BuOH (105 mL) was treated with activated 3 Å mol sieves followed by Et₃N (11.7 mL, 84.0 mmol) and DPPA (10.8 mL, 50.2 mmol). The mixture was stirred at rt for 4 h followed by heating to 90° C. overnight. The mixture was cooled to rt and filter through a pad of Celite. The pad was washed with EtOAc and the filtrate was concentrated to provide the crude product as a viscous amber oil which was further purified by flash chromatography (SiO₂, EtOAc/Hexanes) to afford 12.7 g (87%) of tert-butyl (3-(5-methyl-4-(trifluoromethyl)thiazol-2-yl)bicyclo[1.1.1]pentan-1-yl)carbamate 2-3 as a white solid. LC/MS (APCI) m/z 349.1 $[C_{15}H_{19}F_3N_2O_2S+H]^+$.

A solution of Compound 2-3 (12.7 g, 36.5 mmol) in anhydrous DCM (91 mL) was cooled to 0° C. and treated with TFA (91 mL). The resulting solution was stirred at rt until complete (1 h). The solution was concentrated to provide a pale-yellow oil that was re-dissolved in anhydrous Et₂O (50 mL) and treated with 2N HCl in Et₂O (20 mL) while stiffing. A white precipitate formed immediately and stiffing became difficult. The mixture was further diluted with Et₂O to allow for efficient stiffing then the mixture was concentrated to ¼ of the original volume. The salt exchange process was repeated. The white suspension in Et₂O was filtered and the product was collected and washed with copious amounts of Et₂O to provide 9.97 g (96%) of Compound 2 as a white powder. ¹H NMR (400 MHz, DMSO-d₆) δ 8.93 (br s, NH, 3H), 2.57-2.52 (m, 3H), 2.41 (s, 6H); LC/MS (APCI) m/z 249.1 $[C_{10}H_{11}F_3N_2S+H]^+$.

Example 3

3-(4-(trifluoromethyl)phenyl)bicyclo[1.1.1]pentan-1-amine hydrochloride (3)

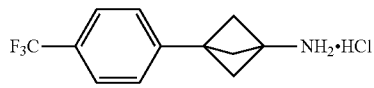

A suspension of ground Mg turnings (0.475 g, 19.6 mmol) in Et₂O (35.6 mL) was treated with 1,2-dibromoethane (0.046 mL, 0.533 mmol) followed by dropwise addition of 1-bromo-4-(trifluoromethyl)benzene (2.49 mL, 17.8 mmol). Once formation was complete (~1 h) as determined by consumption of Mg metal, the Grignard reagent was divided across three separate vials each containing a solution of propellane (18.0 mL, 5.90 mmol) at rt. The resulting mixtures were sealed and heated to 50° C. for 3 days after which the suspensions were cooled to 0° C. CO₂ (dried over anhydrous CaSO₄) was bubbled through the mixtures for 5 minutes. The mixtures were warmed to rt and stirred for an additional 10 minutes then diluted with EtOAc (50 mL) and water (20 mL). The mixtures were acidified with 1N HCl (20 mL) and extracted with EtOAc (3×50 mL). The combined organics were dried ($Na_2SO_4$) and concentrated to provide the crude product which was purified by flash chromatography ($SiO_2$, Hexanes/EtOAc) to provide 0.217 g (5%) of 3-(4-(trifluoromethyl)phenyl)bicyclo[1.1.1]pentane-1-carboxylic acid 3-1 as a semi-pure yellow solid which contains residual 4-(trifluoromethyl)benzoic acid. The product was used without further purification. $^1$H NMR (400 MHz, $CDCl_3$) δ 7.58 (d, J=8.2 Hz, 2H), 7.33 (d, J=8.1 Hz, 2H), 2.41 (s, 6H).

Compound 3-1 (0.216 g, 0.843 mmol) was dissolved in anhydrous toluene (2.11 mL) and t-BuOH (2.11 mL). The mixture was treated with powdered 3 Å mol sieves, $Et_3N$ (0.235 mL, 1.69 mmol), and DPPA (0.218 mL, 1.01 mmol). The resulting mixture was stirred at rt for 4 h then heated to 90° C. and allowed to stir overnight. The mixture was cooled and filtered through Celite. The mixture was diluted with EtOAc (100 mL) and washed with 10% citric acid (20 mL) then brine (20 mL). The combined organics were dried ($Na_2SO_4$) and concentrated to afford the crude product which was further purified by flash chromatography ($SiO_2$, Hexanes/EtOAc) to provide 0.091 g (33%) of tert-butyl (3-(4-(trifluoromethyl)phenyl)bicyclo[1.1.1]pentan-1-yl) carbamate 3-2 as a white solid. LC/MS (APCI) m/z 228.0 $[C_{17}H_{20}F_3NO_2-C_5H_8O_2+H]^+$.

A solution of Compound 3-2 (0.090 g, 0.275 mmol) in EtOAc (1.375 mL) was treated with 2N HCl (1.38 mL, 2.75 mmol) in $Et_2O$. The resulting solution was stirred at rt until complete. The resulting suspension was concentrated to dryness and the resulting solid was triturated and washed with $Et_2O$ to provide 48 mg (67%) of Compound 3 as a white solid. $^1$H NMR (400 MHz, DMSO-$d_6$) δ 8.74 (br s, 3H), 7.70 (d, J=8.2 Hz, 2H), 7.50 (d, J=8.1 Hz, 2H), 2.31 (s, 6H); LC/MS (APCI) m/z 228.0 $[C_{21}H_{12}F_3N+H]^+$.

Example 4

3-(4-Methoxyphenyl)bicyclo[1.1.1]pentan-1-amine hydrochloride (4)

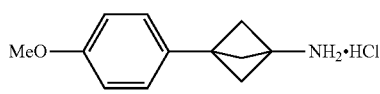

A solution of propellane (20.4 mL, 6.95 mmol) in $Et_2O$ (0.34M) was treated with a 1M solution of (4-chlorophenyl) magnesium bromide (6.95 mL, 6.95 mmol). The resulting mixture was heated to 50° C. in a sealed vial and allowed to stir for 4 days. The mixture was cooled to 0° C. and $CO_2$ (dried over anhydrous $CaSO_4$) was bubbled through the mixture for 5 minutes. The mixture was warmed to rt and stirred for an additional 10 minutes, diluted with EtOAc (50 mL) and acidified with 1N HCl. The mixture was further diluted with $H_2O$ (50 mL) and extracted with EtOAc (3×50 mL). The combined organic layers were dried ($Na_2SO_4$) and concentrated to provide the crude product which was purified by flash chromatography ($SiO_2$, Hexanes/EtOAc) to afford 0.626 g (41%) of 3-(4-chlorophenyl)bicyclo[1.1.1] pentane-1-carboxylic acid 4-1 as a white solid. $^1$H NMR (400 MHz, $CDCl_3$) δ 7.28 (d, J=7.4 Hz, 2H), 7.14 (d, J=7.4 Hz, 2H), 2.35 (s, 6H).

Compound 4-1 (413 mg, 1.86 mmol) was dissolved in t-BuOH (9.27 mL). Activated 3 Å MS (500 mg) were added followed by $Et_3N$ (517 μL, 3.71 mmol) and DPPA (480 μL, 2.23 mmol). The resulting solution was stirred at 30° C. for 4 h, and then heated to reflux overnight. The solution was cooled to rt and then concentrated under reduced pressure. The residual oil was diluted with EtOAc (50 mL) and $H_2O$ (50 mL), and extracted with EtOAc (3×20 mL). The combined organics were dried ($Na_2SO_4$) and concentrated to afford the crude product that was purified by flash chromatography ($SiO_2$, Hexanes/EtOAc) followed by RPLC (RediSep Rf Gold® C18Aq, $H_2O$: ACN) to provide tert-butyl (3-(4-chlorophenyl)bicyclo[1.1.1]pentan-1-yl)carbamate 4-2 (300 mg, 55%) as a white solid. LC/MS (APCI) m/z 194.0 $[C_{16}H_{20}ClNO_2-C_{16}H_9O+H]^+$.

To an oven dried vial was added anhydrous $Cs_2CO_3$ (0.250 g, 0.766 mmol), t-BuBrettPhos (4.95 mg, 10.2 μmol), and Compound 4-2 (0.150 g, 0.511 mmol). The vial was flushed with $N_2$ then anhydrous MeOH (0.103 mL, 2.55 mmol) was added. In a separate oven dried vial, t-BuBrettPhos Pd G3 (8.72 mg, 10.2 μmol) was added followed by dioxane (1.02 mL). The suspension was stirred for ~1 minute to obtain a homogenous solution. The solution containing the Pd catalyst was then transferred to the vial containing the arylchloride and the resulting suspension was stirred at 50° C. overnight. The mixture was cooled to rt, concentrated and directly purified by flash chromatography ($SiO_2$, Hexanes/EtOAc) to provide 0.102 g (69%) of tert-butyl (3-(4-methoxyphenyl)bicyclo[1.1.1]pentan-1-yl)carbamate as a solid 4-3. LC/MS (APCI) m/z 188.0 $[C_{17}H_{23}NO_3-C_5H_8O_2+H]^+$.

A solution of Compound 4-3 (0.138 g, 0.477 mmol) in EtOAc (2.38 mL) was treated with 2N HCl in $Et_2O$ (2.38 mL, 4.77 mmol). The resulting solution was stirred at rt until complete. Once complete, the resulting suspension was concentrated to dryness and the resulting solid was triturated and washed with $Et_2O$ to provide 99 mg (92%) of Compound 4 as a white solid. $^1$H NMR (400 MHz, DMSO-$d_6$) δ 8.74-8.59 (br s, NH, 3H), 7.17 (d, J=8.7 Hz, 2H), 6.88 (d, J=8.6 Hz, 2H), 3.73 (s, 3H), 2.21 (s, 6H); LC/MS (APCI) m/z 173.1 $[C_{12}H_{15}NO-NH_3+H]^+$.

Example 5

3-(3-(trifluoromethyl)phenyl)bicyclo[1.1.1]pentan-1-amine hydrochloride (5)

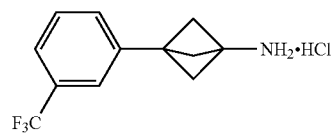

A suspension of ground Mg turnings (0.178 g, 7.33 mmol) in $Et_2O$ (6.67 mL) was treated with 1,2-dibromoethane (0.017 mL, 0.200 mmol) followed by dropwise addition of 1-bromo-3-(trifluoromethyl)benzene (0.932 mL, 6.67 mmol) in 5 mL of anhydrous $Et_2O$. Once formation was complete (~1 h) as determined by consumption of Mg metal, the Grignard reagent was added to a solution of propellane (18.2 mL, 6.00 mmol) at rt. The resulting mixture was sealed and heated to 50° C. for 4 days after which the suspension was cooled to 0° C. $CO_2$ (dried over anhydrous $CaSO_4$) was bubbled through the mixture for 5 minutes. The mixture was warmed to rt and stirred for an additional 10 minutes then diluted with EtOAc (50 mL) and water (20 mL). The mixture was acidified with 1N HCl (20 mL) and extracted with EtOAc (3×50 mL). The combined organics were dried (Na$_2$SO$_4$) and concentrated to provide the crude product which was purified by flash chromatography (SiO$_2$, Hexanes/EtOAc) to provide 0.272 g (16%) of 3-(3-(trifluoromethyl)phenyl)bicyclo[1.1.1]pentane-1-carboxylic acid 5-1 as a beige solid. $^1$H NMR (400 MHz, CDCl$_3$) δ 7.52-7.51 (m, 1H), 7.47-7.35 (m, 3H), 2.40 (s, 6H).

A solution of Compound 5-1 (0.272 g, 1.06 mmol) in a mixture of toluene (2.66 mL) and t-BuOH (2.66 mL) was treated with powdered 3 Å mol sieves, Et$_3$N (0.296 mL, 2.13 mmol), and DPPA (0.275 mL, 1.28 mmol). The resulting mixture was stirred at rt for 4 h then heated to 90° C. and allowed to stir overnight. The mixture was cooled and filtered through Celite. The mixture was diluted with H$_2$O (50 mL) and extracted with EtOAc (4×50 mL). The combined organics were dried (Na$_2$SO$_4$) and concentrated to afford the crude product which was further purified by flash chromatography (SiO$_2$, Hexanes/EtOAc) to afford 0.173 g (50%) of tert-butyl (3-(3-(trifluoromethyl)phenyl)bicyclo[1.1.1]pentan-1-yl)carbamate 5-2 as a soft yellow solid. LC/MS (APCI) m/z 128.1 [C$_{17}$H$_{20}$F$_3$NO—C$_5$H$_8$O$_2$+H]$^+$.

A solution of Compound 5-2 (0.173 g, 0.529 mmol) in EtOAc (2.64 mL) was treated with 2N HCl in Et$_2$O (2.64 mL, 5.29 mmol) and allowed to stir at rt until complete. Once complete, the resulting suspension was concentrated to dryness and the resulting solid was triturated and washed with Et$_2$O to provide 0.110 g (79%) of Compound 5 as a white solid. $^1$H NMR (400 MHz, DMSO-d$_6$) δ 8.80 (br s, NH, 3H), 7.66-7.59 (m, 4H), 2.34 (s, 6H); LC/MS (APCI) m/z 128.1 [C$_{12}$H$_{12}$F$_3$N+H]$^+$.

Example 6

(3-(trifluoromethyl)bicyclo[1.1.1]pentan-1-yl)glycine hydrochloride (6)

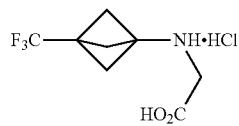

A solution of tert-butyl (3-(trifluoromethyl)bicyclo[1.1.1]pentan-1-yl)carbamate (7.00 g, 27.9 mmol) in anhydrous DMF (55.7 mL) was cooled to 0° C. and NaH (1.67 g, 41.8 mmol) was added. The resulting solution was stirred for 10 minutes followed by the addition of tert-butyl bromoacetate (4.97 mL, 33.4 mmol). The resulting suspension was warmed to rt while stirring. Once complete (2 h), the mixture was carefully quenched with 10% citric acid (~50 mL) and diluted with H$_2$O (~50 mL). The reaction was extracted with EtOAc (3×150 mL) and the combined organics dried (Na$_2$SO$_4$), concentrated and the crude product purified by flash chromatography (SiO$_2$, Hexanes/EtOAc) to provide 9.44 g (93%) of tert-butyl N-(tert-butoxycarbonyl)-N-(3-(trifluoromethyl)bicyclo[1.1.1]pentan-1-yl)glycinate 6-1 as a viscous colorless oil which solidified to a white solid upon standing. LC/MS (APCI) m/z 266.1 [C$_{17}$H$_{26}$F$_3$NO$_3$—C$_5$H$_8$O+H]$^+$.

A solution of Compound 6-1 (9.43 g, 25.8 mmol) in DCM (34.4 mL) was treated with TFA (17.2 mL) and allowed to stir at rt for 36 h at which point additional TFA (10 mL) was added. Stirring was resumed for an additional 24 h. The solution was concentrated and the crude residue was purified by RP-HPLC (C$_{18}$ SiO$_2$, H$_2$O/ACN buffered with 0.1% formic acid) to afford the desired product as a white semisolid. The material was suspended in Et$_2$O and treated with 2N HCl in ether to generate the HCl salt, concentrated, treated again with 2N HCl in Et$_2$O, and then concentrated again. The resulting solid was washed with Et$_2$O and dried to afford 5.07 g (80%) of Compound 6 as a white solid. $^1$H NMR (400 MHz, DMSO-d$_6$) δ 11.39 (br s, 2H), 3.84 (s, 2H), 2.27 (s, 6H); LC/MS (APCI) m/z 210.1 [C$_8$H$_{10}$F$_2$NO+H]$^+$.

Example 7

2-Hydroxy-N-(3-(trifluoromethyl)bicyclo[1.1.1]pentan-1-yl)acetamide (7)

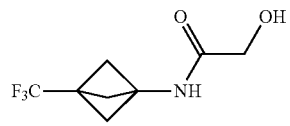 [SMILES: O=C(CO)NC12CC(C(F)(F)F)(C1)C2]

A solution of 3-(trifluoromethyl)bicyclo[1.1.1]pentan-1-amine hydrochloride (12.0 g, 64 0mmol) in DMF (128 mL) at 0° C. was treated with 2-tertiary-butoxyaceticacid (8.23 mL, 64.0 mmol) and N,N-diisopropylethylamine (22.3 mL, 128 mmol). HATU (26.8 g, 70.4 mmol) was added and the resulting solution was stirred at rt overnight. The mixture was concentrated to approximately 1/3 of the original volume, diluted with H$_2$O (200 mL) and extracted with EtOAc (3×150 mL). The combined organics were washed with 10% citric acid (100 mL), water (100 mL) then brine (100 mL). The organic layer was dried (Na$_2$SO$_4$) and concentrated to afford the crude product which was further purified by flash chromatography (SiO$_2$, Hexanes/EtOAc) to provide 14.0 g (82%) of 2-(tert-butoxy)-N-(3-(trifluoromethyl)bicyclo[1.1.1]pentan-1-yl)acetamide 7-1 as a white solid. LC/MS (APCI) m/z 210.1 [C$_{22}$H$_{18}$F$_3$NO$_2$—C$_4$H$_8$+H]$^+$.

A solution of Compound 7-1 (14.0 g, 52.6 mmol) in anhydrous DCM (70.2 mL) was treated with TFA (35.1 mL) and allowed to stir at rt overnight. The mixture was concentrated to afford the crude product which was further purified by flash chromatography (C$_{18}$ SiO$_2$, H$_2$O/ACN buffered with 0.1% formic acid) to provide 9.67 g (88%) of Compound 7 as a white solid. $^1$H NMR (400 MHz, DMSO-d$_6$) δ 8.52 (br s, NH, 1H), 5.46 (br s, OH, 1H), 3.76 (s, 2H), 2.23 (s, 6H); LC/MS (APCI) m/z 210.1 [C$_8$H$_{10}$F$_3$NO$_2$+H]$^+$.

Example 8

N-Ethyl-3-(trifluoromethyl)bicyclo[1.1.1]pentan-1-amine hydrochloride (8)

A solution of tert-butyl (3-(trifluoromethyl)bicyclo[1.1.1]pentan-1-yl)carbamate (0.200 g, 0.796 mmol) in anhydrous DMF (3.98 mL) was cooled to 0° C. and NaH (0.048 g, 1.194 mmol) was added as a 60% dispersion in mineral oil. The resulting solution was stirred for 10 minutes followed by the addition of iodoethane (0.077 mL, 0.955 mmol). The resulting suspension was allowed to warm to rt and stirring was continued for 1.5 h. The mixture was carefully quenched with 10% citric acid, diluted with H$_2$O (20 mL) and extracted with EtOAc (4×20 mL). The combined organics were dried (Na$_2$SO$_4$) and concentrated to afford the crude product which was further purified by flash chromatography (SiO$_2$, Hexanes/EtOAc) to provide 0.125 g (56%) of tert-butyl ethyl(3-(trifluoromethyl)bicyclo[1.1.1]pentan-1-yl) carbamate 8-1 the desired product as a soft solid. LC/MS (APCI) m/z 180.1 [C$_{13}$H$_{20}$F$_3$NO$_2$.C$_5$H$_8$O$_2$+H]$^+$.

A solution of Compound 8-1 (0.125 g, 0.448 mmol) in EtOAc (2.24 mL) was treated with a 2N HCl solution in Et$_2$O (2.24 mL, 4.48 mmol) and allowed to stir at rt until complete. The mixture was concentrated and the resulting white solid triturated with Et$_2$O to provide 84.6 mg (88%) of Compound 8 as white solid. $^1$H NMR (400 MHz, DMSO-d$_6$) δ 9.84 (br s, NH, 2H), 2.92 (q, J=7.3 Hz, 2H), 2.31 (s, 6H), 1.20 (t, J=7.2 Hz, 3H); LC/MS (APCI) m/z 180.1 [C$_8$H$_{12}$F$_3$N+H]$^+$.

Example 9

2-((3-(Trifluoromethyl)bicyclo[1.1.1]pentan-1-yl) amino)ethan-1-ol hydrochloride (9)

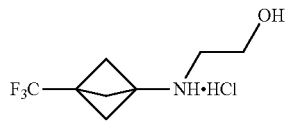

A solution of tert-butyl (3-(trifluoromethyl)bicyclo[1.1.1] pentan-1-yl)carbamate (0.200 g, 0.796 mmol) in anhydrous DMF (3.98 mL) was cooled to 0° C. and NaH (0.0480 g, 1.19 mmol) was added as 60% dispersion in mineral oil. The resulting solution was stirred for 10 minutes followed by the addition of 2-bromoethoxy-t-butyldimethylsilane (0.205 mL, 0.955 mmol). The resulting suspension was allowed to warm to rt and stirred for an additional 1 h. The mixture was carefully quenched with 10% citric acid, diluted with H$_2$O (20 mL) and extracted with EtOAc (4×20 mL). The combined organics were dried (Na$_2$SO$_4$) and concentrated to afford the crude product which was further purified by flash chromatography (SiO$_2$, Hexanes/EtOAc) to provide 0.196 g (60%) of N-(2-((tert-butyldimethylsilyl)oxyethyl)-3-(trifluoromethyl)bicyclo[1.1.1]pentan-1-amine 9-1 as a clear, colorless oil. LC/MS (APCI) m/z 310.2 [C$_{19}$H$_{34}$F$_3$NO$_3$.C$_5$H$_8$O$_2$30 H]$^+$.

A solution of Compound 9-1 (0.196 g, 0.479 mmol) in DCM (2 mL) was treated with TFA (2 mL) and allowed to stir at rt overnight. The solution was concentrated and the resulting residue was dissolved in Et$_2$O (~1 mL). A 2N solution of HCl in Et$_2$O (1 mL) was added to produce a white precipitate which was triturated with Et$_2$O to provide 104 mg (94%) of Compound 9 as white solid. $^1$H NMR (400 MHz, D$_2$O with DDS Na salt as internal standard) δ 3.85-3.81 (m, 2H), 3.21-3.17 (m, 2H), 2.42 (s, 6H); LC/MS (APCI) m/z 196.1 [C$_8$H$_{12}$F$_3$NO+H]$^+$.

Example 10

3-(4-Chlorophenyl)bicyclo[1.1.1]pentan-1-amine hydrochloride (10)

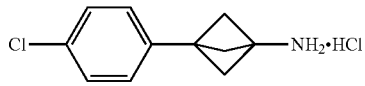

To a solution of tert-butyl (3-(4-chlorophenyl)bicyclo [1.1.1]pentan-1-yl)carbamate (300 mg, 1.02 mmol) in EtOAc (5.10 mL) was added HCl (2N in Et$_2$O, 5.11 mL, 10.2 mmol). The resulting solution was stirred for 2 days at rt. The suspension was concentrated, and the residual solid was triturated with Et$_2$O (2×20 mL). The precipitate was collected by filtration, and the filter cake was washed with Et$_2$O (30 mL). The white solid was dried under vacuum to afford Compound 10 (227 mg, 97%) as a white solid. $^1$H NMR (400 MHz, DMSO-d$_6$) δ 8.87 (br s, 3H), 7.41-7.37 (m, 2H), 7.31-7.27 (m, 2H), 2.26 (s, 6H). LC/MS (APCI) m/z 194.0 [C$_{11}$H$_{12}$ClN+H]$^+$.

Example 11

3-(2-(Trifluoromethyl)pyrimidin-4-yl)bicyclo[1.1.1] pentan-1-amine hydrochloride (11)

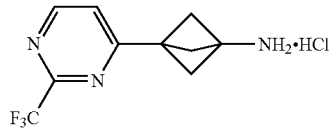

A solution of 3-(methoxycarbonyl)bicyclo[1.1.1]pentane-1-carboxylic acid (5.00 g, 29.4 mmol) in a mixture of toluene (73.5 mL) and t-BuOH (73.5 mL) was treated with powdered 3Å mol sieves, Et$_3$N (8.19 mL, 58.8 mmol) and DPPA (7.61 mL, 35.3 mmol). The resulting mixture was stirred at rt for 4 h then heated to 90° C. and allowed to stir overnight. The mixture was cooled and filtered through a pad of Celite. The mixture was diluted with H$_2$O (50 mL) and extracted with EtOAc (4×50 mL). The combined organics were dried (Na$_2$SO$_4$) and concentrated to afford the crude product which was further purified by flash chromatography (SiO$_2$, Hexanes/EtOAc) to afford 4.56 g (64%) of methyl 3-((tert-butoxycarbonyl)amino)bicyclo[1.1.1]pentane-1-carboxylate 11-1 as a white solid. LC/MS (APCI) m/z 142.1 [C$_{12}$H$_{19}$NO$_4$—C$_5$H$_8$O$_2$+H]$^+$.

To a solution of Compound 11-1 (3.05 g, 12.6 mmol) in THF (21.1 mL), MeOH (21.1 mL), and H$_2$O (21.1 mL) at 0° C. was added LiOH.H$_2$O (1.59 g, 37.9 mmol). The reaction was warmed to rt and stirred overnight. The reaction was concentrated in vacuo to remove THF and MeOH and then diluted with water to 50 mL. The aqueous layer was washed with Et$_2$O and then acidified to pH 3 with 1N HCl. The aqueous layer was extracted with EtOAc (3×50 mL). The combined organic layers were washed with brine, dried over Na$_2$SO$_4$, filtered and concentrated in vacuo to provide 3-((tert-butoxycarbonyl)amino)bicyclo[1.1.1]pentane-1-carboxylic acid 11-2 (2.56 g, 89%) as a white solid. LC/MS (APCI) m/z 128.0 [C$_{11}$H$_{17}$NO$_4$—C$_5$H$_9$O$_2$+H]$^+$.

A solution of Compound 11-2 (1.01 g, 4.44 mmol) in Et$_2$O (22.2 mL) was cooled to −5° C. and treated with MeMgBr (3.0M in Et$_2$O, 4.90 mL, 14.6 mmol). After 30 min, the reaction was warmed to rt. After 16 h, the reaction was cooled to 0° C. and quenched with sat. aqueous NH$_4$Cl solution (5 mL). Upon warming to rt the reaction was diluted with DCM and H$_2$O. The combined organic layers were dried (Na$_2$SO$_4$) and concentrated under reduced pressure to afford tert-butyl (3-acetylbicyclo[1.1.1]pentan-1-yl)carbamate 11-3 (522 mg, 52%) as a white solid. LC/MS (APCI) m/z 126.1 [C$_{12}$H$_{19}$NO$_3$—C$_5$H$_9$O$_2$+H]$^+$.

A solution of Compound 11-3 (376 mg, 1.67 mmol) in DMF (3.33 mL) was treated with 1,1-dimethoxy-N,N-dimethylmethanamine (266 μL, 2.00 mmol) and heated to 100° C. After 2 h, additional 1,1-dimethoxy-N,N-dimethylmethanamine (266 μL, 2.00 mmol) was added and the reaction was again heated to 100° C. After 2 h, the reaction was concentrated in vacuo and then dissolved in EtOH (8.3 mL) and treated with 2,2,2-trifluoroacetamidine (319 μl, 3.51 mmol) and NaOEt (20% in EtOH, 1.37 mL, 3.51 mmol). The reaction mixture was heated to 110° C. using a Biotage Initiator microwave reactor for 3h, cooled to rt and then concentrated in vacuo. The crude reaction mixture was partitioned between DCM and H$_2$O and then the aqueous layer was extracted with DCM (3×30 mL). The combined organic layers were dried (Na$_2$SO$_4$), filtered and concentrated in vacuo. The crude product was purified by column chromatography to provide a yellow oil which was further purified by reverse phase column chromatography to provide tert-butyl (3-(2-(trifluoromethyl)pyrimidin-4-yl)bicyclo[1.1.1]pentan-1-yl)carbamate 11-4 (168 mg, 31%) as a white solid. LC/MS (APCI) m/z 230.0 [C$_{15}$H$_{18}$N$_3$O$_2$—C$_5$H$_9$O$_2$+H]$^+$.

To a solution of Compound 11-4 (161 mg, 0.490 mmol) in EtOAc (2.4 mL) was added HCl (2N in Et$_2$O, 2.93 mL, 5.87 mmol). The resulting solution was stirred for 2 days at rt. The suspension was concentrated, and the residual solid was triturated with Et$_2$O (2×20 mL). The precipitate was collected by filtration, and the filter cake was washed with Et$_2$O (30 mL). The white solid was dissolved in 1:1 ACN:H$_2$O and lyophilized to obtain Compound 11 (116 mg, 89%) as a white solid. $^1$H NMR (400 MHz, DMSO-d$_6$) δ 9.04 (d, J=5.1 Hz, 1H), 8.82 (s, 3H), 7.85 (d, J=5.1 Hz, 1H), 2.41 (s, 6H); $^{19}$F NMR (376 MHz, DMSO-d$_6$, unreferenced) δ-69.06; LC/MS (APCI) m/z 230.0 [C$_{10}$H$_{10}$F$_3$N$_3$+H]$^+$.

Example 12

3-(4-(Trifluoromethyl)pyrimidin-2-yl)bicyclo[1.1.1]pentan-1-amine hydrochloride (12)

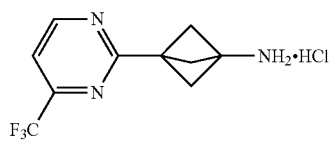

Representative Procedure (reaction was performed in 3 parallel batches using a total of 1.99 g, 12.69 mmol, 3-(methoxycarbonyl)bicyclo[1.1.1]pentane-1-carboxylic acid): A solution of 3-(methoxycarbonyl)bicyclo[1.1.1]pentane-1-carboxylic acid (727 mg, 4.27 mmol), 4-(trifluoromethyl)pyrimidine (561 μL, 5.12 mmol), H$_2$SO$_4$ (273 μL, 5.12 mmol), AgNO$_3$ (218 mg, 1.28 mmol) in a mixture of 1:1 H$_2$O/ACN (14.2 mL) was treated with sodium persulfate (712 mg, 2.99 mmol) and heated to 80° C. After 2 h, the reaction was cooled to rt and the combined reaction mixtures were concentrated in vacuo. MeOH (50 mL) was added followed by 3 drops of conc. H$_2$SO$_4$. The solution was heated to 70° C. for 1 h and then cooled to rt and filtered over Celite. The filtrate was concentrated to ~5 mL and the solution was slowly added to a cooled solution of sat. aq. NaHCO$_3$ (100 mL). The aqueous layer was then extracted with EtOAc (3×50 mL). The combined organic layers were dried (Na$_2$SO$_4$), filtered and concentrated in vacuo. The crude product was purified by normal followed by reverse phase column chromatography to provide methyl 3-(4-(trifluoromethyl)pyrimidin-2-yl)bicyclo[1.1.1]pentane-1-carboxylate 12-1 (181 mg, 4%) as a white solid. LC/MS (APCI) m/z 273.0 [C$_{12}$H$_{11}$F$_3$N$_2$O$_2$+H]$^+$.

A solution of Compound 12-1 (261 mg, 0.959 mmol) in 1:1 ACN:H$_2$O (4.8 mL) was treated with HCl (3N in H$_2$O, 640 μL, 1.92 mmol) and heated to 75° C. After 90 min, the reaction was cooled to rt and then lyophilized to provide 3-(4-(trifluoromethyl)pyrimidin-2-yl)bicyclo[1.1.1]pentane-1-carboxylic acid 12-2 (239 mg, 97%) as a white solid. LC/MS (APCI) m/z 259.0 [C$_{11}$H$_9$F$_3$N$_2$O$_{2+}$H]$^+$.

Compound 12-2 (239 mg, 0.925 mmol) was dissolved in t-BuOH (4.63 mL). Activated 3 Å MS (400 mg) were added followed by Et$_3$N (387 μL, 2.78 mmol) and DPPA (259 μL, 1.20 mmol). The resulting solution was stirred at 35° C. for 4 h, and then heated to 80° C. overnight. The solution was cooled to rt and then concentrated under reduced pressure. The residual oil was diluted with EtOAc (50 mL) and H$_2$O (50 mL), and extracted with EtOAc (3×20 mL). The combined organics were dried (Na$_2$SO$_4$) and concentrated to afford the crude product that was purified by flash chromatography (SiO$_2$, Hexanes/EtOAc) to provide tert-butyl (3-(4-(trifluoromethyl)pyrimidin-2-yl)bicyclo[1.1.1]pentan-1-yl)carbamate 12-3 (119 mg, 39%) as a white solid. LC/MS (APCI) m/z 230.0 [C$_{15}$H$_{18}$F$_3$N$_3$O$_2$—C$_5$H$_9$O$_2$+H]$^+$.

A solution of Compound 12-3 (119 mg, 0.360 mmol) in anhydrous DCM (1.81 mL) was cooled to 0° C. and treated with TFA (278 μL, 3.61 mmol) at rt. After 1 h, additional TFA was added. After an additional 30 min, the reaction was concentrated in vacuo and Et$_2$O (8 mL) was added causing a white solid to crash out of solution. The heterogeneous solution was treated with HCl (2N in Et$_2$O, 3.0 mL, 6.00 mmol) and the reaction mixture was stirred for 2 min The reaction mixture was concentrated in vacuo and the process was repeated an additional 2 times. The suspension was concentrated, and the residual solid was triturated with Et$_2$O. The precipitate was collected by filtration, and the filter cake was washed with Et$_2$O. The white solid was dissolved in 1:1 ACN:H$_2$O and lyophilized to obtain Compound 12 (90.1 mg, 94%) as a white solid. $^1$H NMR (400 MHz, DMSO-d$_6$, 60° C.) δ 9.15 (d, J=5.1 Hz, 1H), 8.86 (s, 3H), 7.91 (d, J=5.1 Hz, 1H), 2.44 (s, 6H); $^{19}$F NMR (376 MHz, DMSO-d$_6$, 60° C., unreferenced) δ-68.65; LC/MS (APCI) m/z 230.0 [C$_{10}$H$_{10}$F$_3$N$_3$+H]$^+$.

Example 13

3-(6-(Trifluoromethyl)pyridin-2-yl)bicyclo[1.1.1]pentan-1-amine hydrochloride (13)

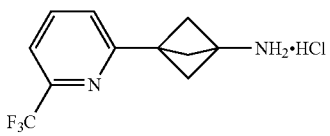

Representative Procedure (reaction was performed in 8 parallel batches using a total of 8.00 g, 47.0 mmol, 3-(methoxycarbonyl)bicyclo[1.1.1]pentane-1-carboxylic acid): A solution of 3-(methoxycarbonyl)bicyclo[1.1.1]pentane-1-carboxylic acid (1.00 g, 5.88 mmol), 2-(trifluoromethyl)pyridine (0.900 mL, 7.80 mmol), $H_2SO_4$ (0.430 mL, 7.80 mmol), and $AgNO_3$ (200 mg, 1.18 mmol) in a mixture of 1:1 $H_2O$:ACN (19.8 mL) was heated to 80° C. and treated with sodium persulfate (1.40 g, 5.88 mmol) in water (5 mL) dropwise. After 1 h, the reaction was cooled to rt and the combined reaction mixtures were concentrated in vacuo. MeOH (50 mL) was added followed by 5 drops of conc. $H_2SO_4$. The solution was heated to 70° C. for 1 h and then cooled to rt and filtered over Celite. The filtrate was concentrated to ~5 mL and the solution was slowly added to a cooled solution of sat aq. $NaHCO_3$ (100 mL). The aqueous layer was then extracted with EtOAc (3×50 mL). The combined organic layers were dried over $Na_2SO_4$, filtered and concentrated in vacuo. The crude product was purified by normal followed by reverse phase column chromatography to provide methyl 3-(6-(trifluoromethyl)pyridin-2-yl)bicyclo[1.1.1]pentane-1-carboxylate 13-1 (600 mg, 5%) as a white solid. LC/MS (APCI) m/z 272.0 $[C_{13}H_{12}F_3NO_2+H]^+$.

A solution of methyl Compound 13-1 (600 mg, 2.12 mmol) in 1:1 ACN:$H_2O$ (11 mL) was treated with HCl (2N in $H_2O$, 3.38 mL, 6.64 mmol) and heated to 80° C. After 1 h, the reaction was cooled to rt and then lyophilized to provide 3-(6-(trifluoromethyl)pyridin-2-yl)bicyclo[1.1.1]pentane-1-carboxylic acid 13-2 (500 mg, 88%) as an off-white solid. LC/MS (APCI) m/z 258.0 $[C_{12}H_{10}F_3NO_2+H]^+$.

A solution of Compound 13-2 (500 mg, 1.94 mmol) was dissolved in 1:1 toluene: tBuOH (9.8 mL) and treated with activated 3 Å MS (400 mg), followed by $Et_3N$ (699 μL, 5.02 mmol), and DPPA (503 μL, 2.33 mmol). The resulting solution was stirred at 35° C. for 4 h, and then heated to 80° C. overnight. The solution was cooled to rt and concentrated to afford the crude product that was then purified by flash chromatography ($SiO_2$, Hexanes/EtOAc) to provide tert-butyl (3-(6-(trifluoromethyl)pyridin-2-yl)bicyclo[1.1.1]pentan-1-yl)carbamate 13-3 (338 mg, 53%) as a white solid. LC/MS (APCI) m/z 329.0 $[C_{16}H_{19}F_3N_2O_2+H]^+$.

A solution of Compound 13-3 (132 mg, 0.402 mmol) in anhydrous DCM (3.00 mL) was cooled to 0° C. and treated with TFA (310 μL, 4.02 mmol) at rt. After 1 h, additional TFA was added. After an additional 30 min, the reaction was concentrated in vacuo and $Et_2O$ (8 mL) was added causing a white solid to crash out of solution. The heterogeneous solution was treated with HCl (2N in $Et_2O$, 2.0 mL, 4.00 mmol) and the reaction mixture was stirred for 2 min. The reaction mixture was concentrated in vacuo and the process was repeated once more. The suspension was concentrated, and the residual solid was triturated with $Et_2O$. The precipitate was collected by filtration, and the filter cake was washed with $Et_2O$. The white solid was dissolved in 1:1 ACN:$H_2O$ and lyophilized to obtain Compound 13 (87.9 mg, 83%) as a white solid. $^1H$ NMR (400 MHz, DMSO-$d_6$) δ 8.78 (s, 3H), 8.08 (t, J=7.8 Hz, 1H), 7.81 (d, J=7.7 Hz, 1H), 7.71 (d, J=7.8 Hz, 1H), 2.37 (s, 6H); $^{19}F$ NMR (376 MHz, DMSO-$d_6$, unreferenced) δ−66.43; LC/MS (APCI) m/z 229.0 $[C_{11}H_{11}F_3N_2+H]^+$.

Example 14

3-(5-(trifluoromethyl)benzo[d]thiazol-2-yl)bicyclo[1.1.1]pentan-1-amine hydrochloride (14)

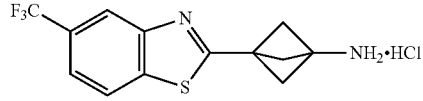

A solution of 2-amino-4-(trifluoromethyl)benzenethiol hydrochloride (0.707 g, 3.08 mmol) and 3-((tert-butoxycarbonyl)amino)bicyclo[1.1.1]pentane-1-carboxylic acid (0.700 g, 3.08 mmol) in 1N aqueous HCl (15.4 mL) was microwaved at 160° C. for 60 minutes. The mixture was concentrated and diluted with EtOAc (50 mL) and water (20 mL). The mixture was neutralized with saturated aqueous $NaHCO_3$ (30 mL) and extracted with EtOAc (4×30 mL). The combined organics were dried ($Na_2SO_4$) and concentrated to provide a yellow residue which was further purified by flash chromatography ($SiO_2$, DCM/0-10% MeOH containing 7N $NH_3$) to provide a pale-yellow oil that solidified upon standing. The material was re-dissolved in EtOAc/$Et_2O$ and treated with 2N HCl in $Et_2O$ to generate the HCl salt. The resulting precipitate was collected via filtration and washed with $Et_2O$ to provide 100 mg (10%) of Compound 14 as an off-white solid. $^1H$ NMR (400 MHz, DMSO-d6) δ 9.01 (br s, NH, 3H), 8.39-8.35 (m, 3H), 7.79 (dd, J=1.7, 8.5 Hz, 1H), 2.52 (s, 6H); LC/MS (APCI) m/z 285.0 $[C_{13}H_{11}F_3N_2S+H]^+$.

Example 15

3-(5-(Trifluoromethyl)benzo[d]oxazol-2-yl)bicyclo[1.1.1]pentan-1-amine hydrochloride (15)

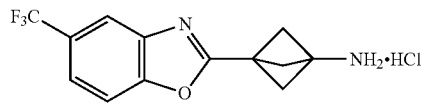

A solution of 3-(methoxycarbonyl)bicyclo[1.1.1]pentane-1-carboxylic acid (0.650 g, 3.82 mmol) in DCM (19.1 mL) was cooled to 0° C. and treated with 2 drops of DMF followed by oxalyl chloride (0.401 mL, 4.58 mmol). The mixture was stirred at rt for 1 h then concentrated. The residue was taken up in DCM (19.1 mL), cooled to 0° C. and treated with Hünig's base (2.00 mL, 11.5 mmol) followed by 2-amino-4-(trifluoromethyl)phenol (0.677 g, 3.82 mmol). The mixture was stirred at rt for 1.5 h then concentrated to provide a crude residue which was further purified by flash chromatography ($SiO_2$, EtOAc/Hexanes) to afford 0.819 g (65%) of methyl 3-((2-hydroxy-5-(trifluoromethyl)phenyl)

carbamoyl)bicyclo[1.1.1]pentane-1-carboxylate 15-1 as an off-white solid. LC/MS (APCI) m/z 330.0 $[C_{15}H_{14}F_3NO_4+H]^+$.

A solution of Compound 15-1 (0.800 g, 2.430 mmol) in TFA (12.2 mL) and AcOH (12.2 mL) was heated at 100° C. in a sealed microwave vial overnight. The mixture was cooled to rt and concentrated to provide crude methyl 3-(5-(trifluoromethyl)benzo[d]oxazol-2-yl)bicyclo[1.1.1]pentane-1-carboxylate 15-2 that also contained 3-(5-(trifluoromethyl)benzo[d] oxazol-2-yl)bicyclo[1.1.1]pentane-1-carboxylic acid 15-3. The mixture was used without further purification. LC/MS (APCI) m/z 312.0 $[C_{15}H_{12}F_3NO_3+H]^+$.

A crude mixture of Compound 15-2 and Compound 15-3 (0.756 g, 2.43 mmol) was dissolved in THF (12.1 mL) and treated with 1M aqueous LiOH (5.34 mL, 5.34 mmol) and allowed to stir overnight. The mixture was acidified with 1N HCl and concentrated. The crude material was triturated with hexanes to provide 0.541 g (75%) of Compound 15-3 as an off-white solid which was used without further purification. LC/MS (APCI) m/z 298.0 $[C_{14}H_{10}F_3NO_3+H]^+$.

A solution of Compound 15-3 (0.540 g, 1.82 mmol) in a mixture of toluene (4.54 mL) and tert-BuOH (4.54 mL) was treated with powdered 3 Å mol sieves, Et$_3$N (0.506 mL, 3.63 mmol) and DPPA (0.471 mL, 2.18 mmol). The resulting mixture was stirred at rt for 4 h then heated to 90° C. and allowed to stir overnight. The mixture was cooled and filtered through a pad of Celite. The mixture was diluted with EtOAc (100 mL) and washed with 10% citric acid (20 mL) then brine (20 mL). The combined organics were dried (Na$_2$SO$_4$) and concentrated to afford the crude product which was further purified by flash chromatography (SiO$_2$, hexanes/EtOAc) to afford 0.299 g (45%) of tert-butyl (3-(5-(trifluoromethyl)benzo[d]oxazol-2-yl)bicyclo[1.1.1]pentan-1-yl)carbamate 15-4 as a white solid. LC/MS (APCI) m/z 282.1 $[C_{18}H_{19}F_3N_2O_3—C_4H_8+H]^+$.

A solution of Compound 15-4 (0.299 g, 0.812 mmol) in EtOAc (4.06 mL) was treated with 2N HCl in Et$_2$O (4.06 mL, 8.12 mmol). The resulting solution was stirred at rt until complete. The mixture was concentrated and the resulting solid was triturated with Et$_2$O and collected via filtration to provide 0.215 g (87%) of Compound 15 as a white solid. $^1$H NMR (400 MHz, DMSO-d$_6$) δ 8.91 (br s, NH, 3H), 8.16 (s, 1H), 7.96 (d, J=8.6 Hz, 1H), 7.80 (dd, J=1.7, 8.6 Hz, 1H), 2.54 (s, 6H); LC/MS (APCI) m/z 269.0 $[C_{13}H_{11}F_3N_2O+H]^+$.

Example 16

3-(5-chlorobenzo[d]oxazol-2-yl)bicyclo[1.1.1]pentan-1-amine hydrochloride (16)

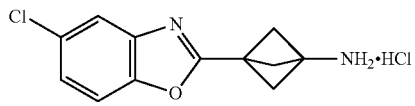

A solution of 3-(methoxycarbonyl)bicyclo[1.1.1]pentane-1-carboxylic acid (0.650 g, 3.82 mmol) in DCM (19.1 mL) was cooled to 0° C. and treated with 2 drops of DMF followed by oxalyl chloride (0.401 mL, 4.58 mmol). The mixture was stirred at rt for 1 h then concentrated. The residue was taken up in DCM (19.1 mL), cooled to 0° C. and treated with Hünig's base (2.00 mL, 11.5 mmol) followed by 2-amino-4-chlorophenol (0.548 g, 3.82 mmol). The mixture was stirred at rt for 1.5 h then concentrated to provide a crude residue which was further purified by flash chromatography (SiO$_2$, EtOAc/Hexanes) to afford 0.604 g (54%) of methyl 3-((5-chloro-2-hydroxyphenyl)carbamoyl)bicyclo[1.1.1]pentane-1-carboxylate 16-1 as a brown solid. LC/MS (APCI) m/z 296.0 $[C_{14}H_{14}ClN_2O_4+H]^+$.

A solution of Compound 16-1 (0.600 g, 2.03 mmol) in TFA (10.1 mL) and AcOH (10.1 mL) was heated at 100° C. in a sealed microwave vial overnight. The mixture was cooled to rt and concentrated to provide crude methyl 3-(5-chlorobenzo[d]oxazol-2-yl)bicyclo[1.1.1]pentane-1-carboxylate which was re-dissolved in THF (10.1 mL) and treated with 1M aqueous LiOH (4.46 mL, 4.46 mmol). The resulting mixture was allowed to stir at rt overnight. The mixture was concentrated and the resulting residue was triturated with hexanes to provide 0.450 g (84%) of semi-pure 3-(5-chlorobenzo[d]oxazol-2-yl)bicyclo[1.1.1]pentane-1-carboxylic acid 16-2 as a light maroon powder. LC/MS (APCI) m/z 263.9 $[C_{13}H_{10}ClNO_3+H]^+$.

A solution of Compound 16-2 (0.450 g, 1.71 mmol) in a mixture of toluene (4.27 mL) and t-BuOH (4.27 mL) was treated with powdered 3 Å molecular sieves, Et$_3$N (0.476 mL, 3.41 mmol) and DPPA (0.442 mL, 2.05 mmol). The resulting mixture was stirred at rt for 4 h then heated to 90° C. and allowed to stir overnight. The mixture was cooled and filtered through a pad of Celite. The mixture was diluted with EtOAc (100 mL) and washed with 10% citric acid (20 mL) then brine (20 mL). The combined organics were dried (Na$_2$SO$_4$) and concentrated to afford the crude product which was further purified by flash chromatography (SiO$_2$, hexanes/EtOAc) to afford 0.356 g (62%) of tert-butyl (3-(5-chlorobenzo[d]oxazol-2-yl)bicyclo[1.1.1]pentan-1-yl)carbamate 16-3 as a light orange solid. LC/MS (APCI) m/z 335.0 $[C_{17}H_{19}ClN_2O_3+H]^+$.

A solution of Compound 16-3 (0.356 g, 1.06 mmol) in EtOAc (5.32 mL) was treated with 2N HCl in Et$_2$O (5.32 mL, 10.6 mmol). The resulting solution was stirred at rt for 2 days. The resulting suspension was concentrated, re-suspended in Et$_2$O and filtered. The collected solid was washed with Et$_2$O and dried to provide 0.230 g (80%) of Compound 16 as a white solid. $^1$H NMR (400 MHz, DMSO-d$_6$) δ 8.97 (br s, NH, 3H), 7.85 (d, J=2.1 Hz, 1H), 7.77 (d, J=8.7 Hz, 1H), 7.47 (dd, J=2.1, 8.7 Hz, 1H), 2.52 (s, 6H); LC/MS (APCI) m/z 235.0 $[C_{12}H_{11}ClN_2O+H]^+$.

Example 17

3-(5-fluoro-1H-benzo[d]imidazol-2-yl)bicyclo[1.1.1]pentan-1-amine hydrochloride (17)

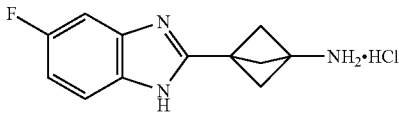

A solution of 2-amino-4-fluoroaniline (0.278 g, 2.20 mmol) and 3-((tert-butoxycarbonyl)amino)bicyclo[1.1.1]pentane-1-carboxylic acid (0.500 g, 2.20 mmol) in a 1N aqueous HCl (11.0 mL) was microwaved at 160° C. for 50 minutes. The dark mixture was filtered through a plug of C$_{18}$ silica gel and washed with ACN. The filtrate was concentrated to provide the crude product which was further purified by flash chromatography (C$_{18}$ SiO$_2$, H$_2$O/ACN buffered with 0.1% formic acid) to afford the desired product. The material was re-dissolved in EtOAc/Et$_2$O and treated with 2N HCl in ether to generate the HCl salt. The resulting precipitate was collected via filtration and washed with Et₂O to provide 0.250 g (45%) of Compound 17 as an off-white solid. ¹H NMR (400 MHz, DMSO-d₆) δ 9.17 (br s, NH, 3H), 7.76 (dd, J=4.5, 8.9 Hz, 1H), 7.60 (dd, J=2.3, 8.7 Hz, 1H), 7.36 (dt, J=2.3, 9.4 Hz, 1H), 2.60 (s, 6H); LC/MS (APCI) m/z 218.1 [C₁₂H₁₂FN₃+H]⁺.

Example 18

3-(3-Methoxyphenyl)bicyclo[1.1.1]pentan-1-amine hydrochloride (18)

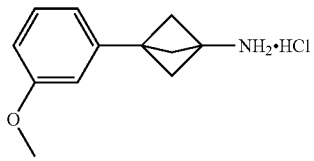

Mg turnings (0.260 g, 10 7 mmol) were added to an oven dried sealed tube fitted with a septa and N₂ balloon. Anhydrous Et₂O (20 mL) was added followed by 1-bromo-3-methoxybenzene (1.35 mL, 10.7 mmol) and 46 µL of 1,2-dibromoethane. The flask was sealed and stirred at reflux for 3 h. After cooling to rt, the flask was fitted with septa and N₂ balloon. The flask was charged with propellane solution (31.3 mL, 10 7 mmol), sealed, and stirred at 60° C. for 3 days. The flask was cooled to 0° C. under N₂ and CO₂ was bubbled through the solution for 10 minutes. Et₂O (40 mL) and 10 mL 2N NaOH was added. The mixture was filtered through Celite. The layers were separated and the organic layers were washed with 2M NaOH (20 mL). The combined water layers were acidified to pH 1 with 2N HCl. The water layers were extracted with EtOAc (3×75 mL). The combined organic layers were washed with brine and dried (MgSO₄) to give 950 mg of crude residue. The material was absorbed onto Celite and purified by reverse phase chromatography to give 350 mg (15%) of 3-(3-methoxyphenyl)bicyclo[1.1.1]pentane-1-carboxylic acid 18-1 as a white solid. ¹H NMR (400 MHz, DMSO-d₆) δ 12.43 (s, 1H), 7.24-7.21 (m, 1H), 6.82-6.78 (m, 2H), 6.76-6.75 (m, 1H), 3.74 (s, 3H), 2.20 (s, 6H).

Compound 18-1 (0.688 g, 3.15 mmol) was added to a 100 mL RBF and sealed under N₂. Et₃N (0.879 mL, 6.30 mmol) and DPPA (0.800 mL, 3.71 mmol) were added. The reaction was stirred for 1 h. 4 Å molecular sieves were added and the reaction was stirred for 3 h. The reaction was then refluxed overnight. The solvent was evaporated and the residue was absorbed onto Florisil and purified by flash chromatography (SiO₂, EtOAc/Hexanes) to afford 437 mg (48%) of tert-butyl (3-(3-methoxyphenyl)bicyclo[1.1.1]pentan-1-yl)carbamate 18-2. ¹H NMR (400 MHz, DMSO-d₆) δ 7.57 (s, 1H), 7.22-7.18 (m, 1H), 6.79-6.71 (m, 2H), 6.74-6.73 (m, 1H), 3.73 (s, 3H), 2.13 (s, 6H), 1.39 (s, 9H).

Compound 18-2 (0.535 g, 1.85 mmol) was dissolved in 2 mL DCM and 1 mL TFA was added. The reaction was stirred at rt for 3 h where it was determined to be complete by LCMS. The reaction was concentrated and 5 mL 1N HCl in Et₂O was added with stiffing. The mixture was concentrated and the cycle was repeated three times. 1N HCl in Et₂O (5 mL) and 10 mL Et₂O was added with stiffing. The white precipitate was filtered and rinsed with Et₂O. The solid was dried overnight under high vacuum to give 340 mg (81%) of Compound 18 as a white powder. ¹H NMR (400 MHz, DMSO-d₆) δ 8.90 (br s, NH, 3H), 7.25-7.22 (m, 1H), 6.84-6.70 (m, 3H), 3.74 (s, 3H), 2.25 (s, 6H); LC/MS (APCI) m/z 190.1 [C₁₂H₁₅NO+H]⁺.

Example 19

3-(1,1-Difluoroethyl)bicyclo[1.1.1]pentan-1-amine hydrochloride (19)

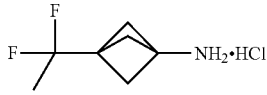

In an oven-dried round bottom flask fitted with a septum, a 0.305M solution of propellane (62.0 mL, 18.9 mmol) was injected followed by a 0.5M solution of p-tolylmagnesium bromide (37.8 mL, 18.9 mmol). The septum was replaced with a glass stopper wrapped with Teflon tape and the resulting cloudy mixture was stirred at rt for 4 days. The mixture was then cooled to 0° C. and dry (CaSO₄) CO₂ gas was bubbled through the mixture for 10 minutes. The mixture was then acidified with 1N HCl, diluted with H₂O (40 mL) and extracted with EtOAc (4×30 mL). The combined organics were dried (Na₂SO₄) and concentrated under reduced pressure to provide the crude product that was further purified by flash chromatography (SiO₂, Hexanes/ EtOAc) to afford 1.96 g (51%) of 3-(p-tolyl)bicyclo[1.1.1] pentane-1-carboxylic acid 19-1 as an off-white solid. ¹H NMR (400 MHz, DMSO-d₆) δ 12.4 (br s, COOH, 1H), 7.11 (s, 4H), 2.27 (s, 3H), 2.18 (s, 6H).

Compound 19-1 (4.74 g, 23.4 mmol) was added to an oven dried 500 mL flask that was fitted with a septa and N₂ balloon. The solid was suspended in 70 mL dry Et₂O and the suspension was cooled to 0° C. MeLi (32.2 mL, 51.6 mmol) was added dropwise and the reaction was stirred from 0° C. to rt overnight. The reaction was determined to be complete by TLC. The reaction was cooled to 0° C. and acidified to pH 1 with 1N HCl. The mixture was extracted with EtOAc (3×50 mL). The combined organic layers were washed with brine (1×100 mL) and dried (Na₂SO₄). The compound was purified by flash chromatography (SiO₂, EtOAc/Hexanes) to afford 2.74 g (58%) of 1-(3-(p-tolyl)bicyclo[1.1.1]pentan-1-yl)ethan-1-one 19-2 as a colorless oil. ¹H NMR (400 MHz, DMSO-d₆) δ 7.12 (s, 4H), 2.27 (s, 3H), 2.19 (s, 6H), 2.13 (s, 3H).

Compound 19-2 (2.50 g, 12.5 mmol) was dissolved in 2.7M DeoxoFluor (13.9 mL, 37.4 mmol) in toluene. The reaction was stirred for two days where it was determined to be complete by TLC. The reaction was slowly added to 100 mL of a 0° C. solution saturated aqueous NaHCO₃. The mixture was extracted with EtOAc (3×50 mL). The organic layers were washed with brine and dried (Na₂SO₄). The solvent was removed and the residue was purified by flash chromatography (SiO₂, EtOAc/Hexanes) to afford 1.45 g (52%) of 1-(1,1-difluoroethyl)-3-(p-tolyl)bicyclo[1.1.1]pentane 19-3 as a white solid. ¹H NMR (400 MHz, DMSO-d₆) δ 7.12 (s, 4H), 2.27 (s, 3H), 2.04 (s, 6H), 1.61 (t, J=18.6 Hz, 3H).

Compound 19-3 (1.44 g, 6.48 mmol) was dissolved in 30 mL ACN and 30 mL water. NaIO4 (13.9 g, 64.8 mmol) was added followed by RuCl₃·xH₂O (0.134 g, 0.648 mmol). DCM (10 mL) was added followed by 10 mL water and 10 mL ACN to facilitate stiffing. The reaction was stirred overnight where it was determined to be complete by TLC. The solvents were removed in vacuo. 300 mL of 10% iPrOH/EtOAc was added. MgSO$_4$ was added with vigorous stirring. The mixture was filtered through Celite, and the solvent removed to give a dark orange oil. The residue was absorbed onto Florisil® and was purified by flash chromatography (SiO$_2$, EtOAc/Hexanes) to give 755 mg (60%) of 3-(1,1-difluoroethyl)bicyclo[1.1.1]pentane-1-carboxylic acid 19-4 as a white solid. $^1$H NMR (400 MHz, DMSO-d$_6$) δ 12.57 (s, 1H), 2.02 (s, 6H), 1.56 (t, J=18.7 Hz, 3H).

Compound 19-4 (0.735 g, 4.17 mmol) was dissolved in 12 mL t-BuOH. Et$_3$N (1.16 mL, 8.34 mmol) was added by DPPA (0.989 mL, 4.59 mmol). The reaction was stirred for 1 h and 4 Å molecular sieves were added. The reaction was stirred for 3 h at rt. The reaction was then fitted with a reflux condenser refluxed overnight. The 4 Å molecular sieves were removed via filtration and the reaction was concentrated. The compound was absorbed onto Florisil® and purified by flash chromatography (SiO$_2$, EtOAc:Hexanes) to give 175 mg (17%) of tert-butyl (3-(1,1-difluoroethyl)bicyclo[1.1.1]pentan-1-yl)carbamate 19-5 as a white solid. $^1$H NMR (400 MHz, DMSO-d$_6$) δ 7.61 (s, 1H), 1.95 (s, 6H), 1.56 (t, J=18.6 Hz, 3H), 1.37 (s, 9H).

Compound 19-5 (0.161 g, 0.651 mmol) was dissolved in 2 mL DCM and 1 mL TFA was added. The reaction was determined to be complete in 2 h by LCMS. The reaction was concentrated and 1N HCl in Et$_2$O (5 mL) was added with stirring. The mixture was concentrated and the cycle was repeated three times. 1N HCl in Et$_2$O (5 mL) and 10 mL Et$_2$O was added with stirring. The white precipitate was filtered and rinsed with Et$_2$O. The solid was dried overnight under high vacuum to give 96 mg (80%) of Compound 19 as a white powder. $^1$H NMR (400 MHz, DMSO-d$_6$) δ 9.03 (s, 3H), 2.07 (s, 6H), 1.61 (t, J=18.8 Hz, 3H); LC/MS (APCI) m/z 148.1 [C$_7$H$_{11}$F$_2$N+H]$^+$.

ExampleS 20 AND 21

3-(1,1-Difluoro-2-methylpropyl)bicyclo[1.1.1]pentan-1-amine hydrochloride (20) and 3-(1-fluoro-2-methylprop-1-en-1-yl)bicyclo[1.1.1]pentan-1-amine hydrochloride (21)

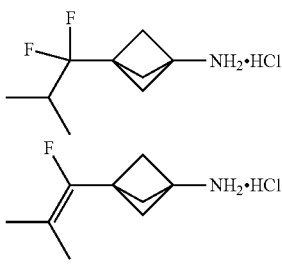

3-(Methoxycarbonyl)bicyclo-[1.1.1]pentane-1-carboxylic acid (5.00 g, 29.4 mmol) was dissolved in 30 mL DCM under N$_2$. Oxalyl chloride was added and the reaction was stirred overnight. The solvent was removed and the reaction was monitored by $^1$H NMR. The material was dissolved in 30 mL THF and cooled to −78° C. under N$_2$. 2.0M iPrMgBr in Et$_2$O (14.7 mL, 29 4 mmol) was added and the reaction was stirred for 3 h and quenched at −78° C. with saturated aqueous NH$_4$Cl. The mixture was extracted with EtOAc (3×75 mL) and the combined organic layers were washed with brine (100 mL). The solution was dried (Na$_2$SO$_4$) and concentrated. The crude mixture was purified by flash chromatography (SiO$_2$, EtOAc/Hexanes) to afford 3.91 g (68%) of methyl 3-isobutyrylbicyclo[1.1.1]pentane-1-carboxylate 20-1 as a colorless oil. $^1$H NMR (400 MHz, DMSO-d$_6$) δ 3.62 (s, 3H), 2.88 (sep, J=6.9 Hz, 1H), 2.25 (s, 6H), 0.97 (d, J=6.8 Hz, 6H).

Compound 20-1 (1.00 g, 5.10 mmol) was dissolved in neat Deoxo-Fluor® (3.76 mL, 20.4 mmol) and the reaction was stirred at rt overnight. The reaction was diluted with 15 mL of EtOAc and that mixture was slowly added at 0° C. to 75 mL of saturated aqueous NaHCO$_3$ with stirring. The mixture was extracted with EtOAc (3×50 mL). The combined organic layers were washed with brine (100 mL) and dried (Na$_2$SO$_4$). The solvent was removed and the residue was purified by flash chromatography (SiO$_2$, EtOAc: Hexanes) to afford 850 mg of a colorless oil that is an inseparable mixture of methyl 3-(1,1-difluoro-2-methylpropyl)bicyclo[1.1.1]pentane-1-carboxylate 20-2 and methyl 3-(1-fluoro-2-methylprop-1-en-1-yl)bicyclo[1.1.1]pentane-1-carboxylate 21-2. Compound 20-2: $^1$H NMR (400 MHz, DMSO-d$_6$) δ 2.24 (s, 3H), 2.17-1.08 (m, 1H), 2.14 (s, 6H), 0.97 (d, J=7.2 Hz, 6H); Compound 21-2: 2.13 (s, 3H), 2.25 (s, 6H), 1.61-1.57 (m, 6H).

A mixture of Compound 20-2 and Compound 21-2 (0.800 g, 3.67 mmol) was dissolved in 15 mL of 4:1 THF/water. LiOH (0.769 g, 18 3 mmol) was added and the reaction was stirred for 3 h at rt where it was determined to be complete by TLC. The THF was removed and the mixture was acidified to pH 1 with 1N HCl (aq.). The mixture was extracted with EtOAc (3×30 mL). The combined organic layers were washed with brine (75 mL) and dried (Na$_2$SO$_4$). The mixture was dried on the high vacuum to afford 572 mg of a mixture of 3-(1,1-difluoro-2-methylpropyl)bicyclo[1.1.1]pentane-1-carboxylic acid 20-3 and 3-(1-fluoro-2-methylprop-1-en-1-yl)bicyclo[1.1.1]pentane-1-carboxylic acid 21-3. Compound 20-3: $^1$H NMR (400 MHz, DMSO-d$_6$) δ 12.51 (s, 1H), 2.15-2.08 (m, 1H), 2.09 (s, 6H), 0.973 (d, J=6.8 Hz, 6H); Compound 21-3: 12.51 (s, 1H), 2.19 (s, 6H), 1.61-1.57 (m, 6H).

A mixture of Compound 20-3 and Compound 21-3 (1.00 g, 4.90 mmol) was dissolved in 14 mL dry t-BuOH. Et$_3$N (1.36 mL, 9.79 mmol) was added followed by DPPA (1.05 mL, 4.90 mmol). The reaction was stirred at rt for 1 h and 4 Å molecular sieves were added. The reaction was stirred for 3 h and then refluxed overnight. The mixture was filtered and the solvent was removed in vacuo. The reaction was dissolved in 50 mL EtOAc and washed with brine (50 mL) and dried (Na$_2$SO$_4$). The residue was absorbed on Florisil® and purified by flash chromatography (SiO$_2$, EtOAc/Hexanes) to provide 430 mg of tert-butyl (3-(1,1-difluoro-2-methylpropyl)bicyclo[1.1.1]pentan-1-yl)carbamate 20-4 as a white solid and 302 mg of tert-butyl (3-(1-fluoro-2-methylprop-1-en-1-yl)bicyclo[1.1.1]pentan-1-yl)carbamate 21-4 as a white solid. Compound 20-4: $^1$H NMR (400 MHz, DMSO-d$_6$) δ 7.60 (s, 1H), 2.19-2.07 (m, 1H), 2.02 (s, 6H), 1.37 (s, 9H), 0.96 (d, J=6.8 Hz, 6H). Compound 21-4: $^1$H NMR (400 MHz, DMSO-d$_6$) δ 7.57 (s, 1H), 2.11 (s, 6H), 1.59-1.56 (m, 6H), 1.37 (s, 9H).

Compound 20-4 (0.400 g, 1.45 mmol) was dissolved in 2 mL DCM and 1 mL TFA was added. The reaction was determined to be complete in 2 h by LCMS. The reaction was concentrated and 1N HCl in Et$_2$O (5 mL) was added with stirring. The mixture was concentrated and the cycle was repeated three times. 1N HCl in Et$_2$O (5 mL) and 10 mL Et$_2$O was added with stirring. The white precipitate was filtered, rinsed with Et$_2$O and the solid was dried overnight under high vacuum to give 210 mg (68%) of Compound 20 as a white powder. $^1$H NMR (400 MHz, DMSO-$d_6$) δ 9.03 (s, 3H), 2.21-2.09 (m, 1H), 2.13 (s, 6H), 0.97 (d, J=6.9 Hz, 6H); LC/MS (APCI) m/z 176.1 $[C_9H_{15}F_2N+H]^+$.

Compound 21-4 (0.250 g, 0.979 mmol) was dissolved in 2 mL DCM and 1 mL TFA was added. The mixture was stirred for 2 h at rt at which point it was determined to be complete by LCMS. The reaction was concentrated and 5 mL of 1N HCl in Et$_2$O was added with stirring. The mixture was concentrated and the cycle was repeated three times. 1N HCl in Et$_2$O (5 mL) and 10 mL Et$_2$O was added with stirring. The white precipitate was filtered, rinsed with Et$_2$O and the solid was dried overnight under high vacuum to give 121 mg (64%) of Compound 21 as a white powder. $^1$H NMR (400 MHz, DMSO-$d_6$) δ 8.96 (s, 3H), 2.22 (s, 6H), 1.60-1.59 (m, 6H); LC/MS (APCI) m/z 156.1 $[C_9H_{14}FN+H]^+$.

Example 22

3-Phenylbicyclo[1.1.1]pentan-1-amine hydrochloride (22)

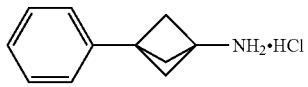

To a solution of propellane (0.34M in Et$_2$O, 50.0 mL, 17.0 mmol) was added PhMgBr (3M in Et$_2$O, 5.67 mL, 17.0 mmol). The reaction flask was sealed and stirred at rt. After 4 days, the mixture was cooled to −78° C. and dry (CaSO$_4$) CO$_2$ gas was bubbled through the mixture for 10 minutes. The mixture was warmed to 0° C. for 10 min and then acidified with 2N HCl, diluted with H$_2$O and extracted with EtOAc. The combined organics were dried (Na$_2$SO$_4$) and concentrated under reduced pressure to provide the crude product that was further purified by flash chromatography (SiO$_2$, Hexanes/EtOAc) to afford 3-phenylbicyclo[1.1.1] pentane-1-carboxylic acid 22-1 (900 mg, 28%) as a white solid. $^1$H NMR (400 MHz, CDCl$_3$) δ 7.35-7.20 (m, 5H), 2.37 (s, 6H).

Compound 22-1 (366 mg, 1.95 mmol) was dissolved in t-BuOH (9.73 mL). Activated 3 Å MS (500 mg) were added followed by Et$_3$N (543 µL, 3.89 mmol) and DPPA (503 µL, 2.34 mmol). The resulting solution was stirred at 30° C. for 4 h, and then heated to reflux overnight. The solution was cooled to rt and then concentrated under reduced pressure. The residual oil was diluted with EtOAc (50 mL) and H$_2$O (50 mL), and extracted with EtOAc (3×20 mL). The combined organics were dried (Na$_2$SO$_4$) and concentrated to afford the crude product that was further purified by flash chromatography (SiO$_2$, Hexanes/EtOAc) to provide tert-butyl (3-phenylbicyclo[1.1.1]pentan-1-yl)carbamate 22 (310 mg, 61%) as a clear colorless oil. $^1$H NMR (400 MHz, CDCl$_3$) δ 7.32-7.27 (m, 2H), 7.24-7.19 (m, 3H), 2.28 (s, 6H), 1.47 (s, 9H). LC/MS (APCI) m/z 160.1 $[C_{16}H_{21}NO_2-C_5H_9O_2+H]^+$.

Example 23

(S)-2-Amino-3-methyl-N-(3-(trifluoromethyl)bicyclo[1.1.1]pentan-1-yl)butanamide hydrochloride (23)

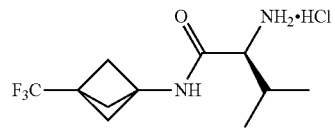

tert-Butyl (3-(trifluoromethyl)bicyclo[1.1.1]pentan-1-yl) carbamate (0.500 g, 0.198 mmol) was treated with 4N HCl in dioxane (2 mL). The mixture was stirred at rt for 4 h then concentrated under reduced pressure. The resulting 3-(trifluoromethyl)bicyclo[1.1.1]pentan-1-amine hydrochloride 23-1 was used without further purification.

A suspension of Compound 23-1 (0.190 g, 1.01 mmol) in DCM was treated with Et$_3$N (0.413 mL, 2.96 mmol), (S)-2-tert-butoxycarbonylamino-3-methyl-butyric acid (0.330 g, 1.50 mmol) and HATU (0.760 g, 2.00 mmol) then allowed to stir at rt for 2 h. The mixture was diluted with EtOAc and washed with saturated aqueous NH$_4$Cl. The organic layer was dried (Na$_2$SO$_4$) and concentrated under reduced pressure to provide the crude product which was further purified by flash chromatography (SiO$_2$, EtOAc/Hexanes) to afford 220 mg (63%) of tert-butyl (S)-(3-methyl-1-oxo-1-((3-(trifluoromethyl)bicyclo[1.1.1]pentan-1-yl)amino)butan-2-yl)carbamate 23-2 which was used immediately in the next step.

Compound 23-2 (0.200 g, 0.571 mmol) was treated with 4N HCl in dioxane (2 mL) and allowed to stir at rt for 4 h. The mixture was concentrated under reduced pressure and the resulting residue was lyophilized from a mixture of H$_2$O/ACN to afford 150 mg (91%) of Compound 23 as a white solid. $^1$H NMR (400 MHz, CDCl$_3$) δ 9.17 (s, 1H), 8.03 (s, 3H), 3.50-3.51 (m, 1H), 2.26 (s, 6H), 2.08-2.13 (m, 1H), 0.94-0.97 (m, 6H); LC/MS (ESI$^+$) m/z 251.2 $[C_{11}H_{17}F_3N_2O+H]^+$.

Example 24

Ethyl (3-(trifluoromethyl)bicyclo[1.1.1]pentan-1-yl) carbamate (24)

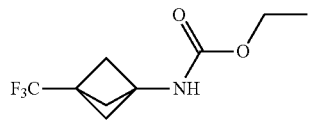

A suspension of 3-(trifluoromethyl)bicyclo[1.1.1]pentan-1-amine hydrochloride (0.190 g, 1.01 mmol) in DCM (1 mL) was cooled to 0° C. then treated with Et$_3$N (0.441 mL, 3.16 mmol) followed by ethyl chloroformate (0.106 mL, 1.11 mmol). The resulting solution was allowed to warm to rt while stirring. Once the solution reached rt, the solvent was removed under reduced pressure and the resulting residue was purified by flash chromatography (SiO$_2$, EtOAc/Hexanes) to provide 100 mg (45%) of Compound 24 as a white solid. $^1$H NMR (400 MHz, CDCl$_3$) δ 5.10 (s, 1H), 4.11-4.13 (m, 2H), 2.24 (s, 6H), 1.23-1.27 (m, 3H); LC/MS (ESI⁺) m/z 246.1 [$C_9H_{12}F_3NO_2$+Na]⁺.

Example 25

3-(4-(1,1-difluoroethyl)thiazol-2-yl)bicyclo[1.1.1]pentan-1-amine hydrochloride (25)

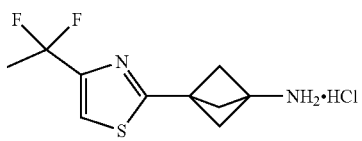

Representative Procedure (reaction was performed in 5 parallel batches using total of 17.77 g starting thioamide). Methyl 3-carbamothioylbicyclo[1.1.1]pentane-1-carboxylate (3.00 g, 16.2 mmol) was added to a 20 mL MW tube. 1-Bromobutane-2,3-dione (1.74 mL, 17.0 mmol) was dissolved in 16 mL MeOH and added to the vial. The reaction was heated at 100° C. using a Biotage Initiator microwave reactor for 30 minutes and then combined with the other batches and concentrated in vacuo. The crude reaction mixture was partitioned between sat. aq. NaHCO₃ and EtOAc and then the water layer was extracted with EtOAc (3×150 mL). The combined organic layers were washed with brine, dried over Na₂SO₄, filtered and concentrated in vacuo. The crude product was adsorbed onto Celite® and then purified by flash chromatography (SiO₂, EtOAc/Hexanes) to provide a yellow solid. The product was further purified by triturating the yellow solid (2x) with hexanes to provide 19.4 g (80%) of methyl 3-(4-acetylthiazol-2-yl)bicyclo[1.1.1]pentane-1-carboxylate 25-1 as a white solid. LC/MS (APCI) m/z 252.0 [$C_{12}H_{13}NO_3S$+H]⁺.

Representative Procedure (reaction was performed in 4 parallel batches using total of 18.1 g of Compound 25-1). Compound 25-1 (4.10 g, 16 3 mmol) was suspended in 9 mL Deoxo-Fluor and heated to 60° C. The mixture became a clear solution in 10 minutes. The reaction was stirred overnight and then cooled to rt. The crude reactions were cautiously added to a solution of 800 mL sat. aq. NaHCO₃ and 100 mL EtOAc at 0° C. by pipette. (Note: vigorous gas evolution was observed during the quenching of the reaction in the absence of EtOAc). The organic layer was separated and the aqueous layer was extracted with EtOAc (3×150 mL). The combined organic layers were washed with brine, dried (Na₂SO₄), filtered and concentrated in vacuo. The crude product was adsorbed onto Celite® and then purified by flash chromatography (SiO₂, EtOAc/Hexanes) to provide 15.2 g (77%) of methyl 3-(4-(1,1-difluoroethyl)thiazol-2-yl)bicyclo[1.1.1]pentane-1-carboxylate 25-2 as a white solid. LC/MS (APCI) m/z 274.0 [$C_{12}H_{13}F_2NO_2S$+H]⁺.

To a solution of Compound 25-2 (13.5 g, 49.4 mmol) in THF (99 mL) and water (24.7 mL) at 0° C. was added LiOH·H₂O (4.15 g, 99 mmol). The reaction was warmed to rt and stirred for 2 h. The THF was then removed in vacuo and the reaction was diluted with water to ~100 mL. The aqueous layer was washed with Et₂O and then acidified to pH 3 with 1N HCl. The aqueous layer was then extracted with EtOAc (3×150 mL). The combined organic layers were washed with brine, dried (Na₂SO₄), filtered and concentrated in vacuo to provide 12.1 g (95%) of 3-(4-(1,1-difluoroethyl)thiazol-2-yl)bicyclo[1.1.1]pentane-1-carboxylic acid 25-3 as a white solid. LC/MS (APCI) m/z 260.0 [$C_{11}H_{11}F_2NO_2S$+H]⁺.

Compound 25-3 (13.6 g, 52.5 mmol) was dissolved in t-BuOH (131 mL) and anhydrous toluene (131 mL). Activated 3 Å MS (13.0 g) were added followed by Et₃N (14.6 mL, 105 mmol) and DPPA (13.6 mL, 62.9 mmol). The resulting solution was stirred at 30° C. for 4 h, and then heated to reflux overnight. The solution was cooled to rt and then filtered through a pad of Celite®. The pad was then washed with EtOAc (50 mL) and the combined filtrates were concentrated in vacuo. The crude product was adsorbed onto Celite® and then purified by flash chromatography (SiO₂, EtOAc/Hexanes) to provide 13.1 g (75%) of tert-butyl (3-(4-(1,1-difluoroethyl)thiazol-2-yl)bicyclo[1.1.1]pentan-1-yl)carbamate 25-4 as a white solid. LC/MS (APCI) m/z 331.1 [$C_{18}H_{20}F_2N_2O_2S$+H]⁺.

A solution of Compound 25-4 (13.0 g, 39.3 mmol) in anhydrous DCM (98 mL) was cooled to 0° C. and treated with TFA (98 mL) at rt. After 90 min, the reaction was concentrated in vacuo and Et₂O (50 mL) was added causing a white solid to crash out of solution. The heterogeneous solution was treated with HCl (4N in Et₂O, 20 mL, 80.0 mmol) and the reaction mixture was stirred for 2 min. The reaction mixture was concentrated in vacuo and the process was repeated an additional 2x using 20 mL and 10 mL 4N HCl in dioxane respectively. The suspension was concentrated, and the residual solid was triturated with Et₂O. The precipitate was collected by filtration, and the filter cake was washed with Et₂O. The white solid was dried under vacuum to afford 10.2 g (97%) of Compound 25 as a white solid. ¹H NMR (400 MHz, DMSO-d₆, 60 C) δ 8.92 (s, 3H), 7.96 (t, J=1.1 Hz, 1H), 2.45 (s, 6H), 1.99 (t, J=18.8 Hz, 3H); ¹⁹F NMR (376 MHz, DMSO-d₆, 60 ° C., unreferenced) δ−84.32; LC/MS (APCI) m/z 231.0 [$C_{10}H_{12}F_2N_2S$+H]⁺.

Example 26

(5Z,8Z,11Z,14Z)—N-(3-(4-(trifluoromethyl)thiazol-2-yl)bicyclo[1.1.1]pentan-1-yl)icosa-5,8,11,14-tetraenamide (26)

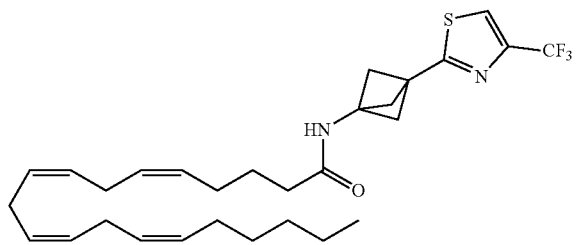 [SMILES: CCCCC/C=C\C/C=C\C/C=C\C/C=C\CCCC(=O)NC12CC(c3nc(C(F)(F)F)cs3)(C1)C2]

The following operations were performed in a manner as to minimize exposure to light. A solution of (5Z,8Z,11Z,14Z)-icosa-5,8,11,14-tetraenoic acid (40 mg, 0.131 mmol) in DCM (0.9 mL) and DMF (10 μL) was cooled to 0° C. and oxalyl chloride (23 μl, 0.263 mmol) was added dropwise. The reaction mixture was stirred for an additional 1 h followed by the addition of a solution of Compound 1 (107 mg, 0.394 mmol) in pyridine (32 μl, 0.394 mmol). The mixture was warmed to rt and stirred for an additional 30 minutes. The mixture was diluted with DCM (5 mL) and washed with 10% aqueous HCl and water. The organic layer was dried (Na₂SO₄), concentrated and purified by flash chromatography (SiO$_2$, Hexanes/EtOAc) to provide 62 mg (91%) of Compound 26 as a viscous pale yellow oil: $^1$H NMR (400 MHz, CDCl$_3$) δ 7.65 (s, 1H), 5.86 (br s, 1H), 5.43-5.30 (m, 8H), 2.86-2.79 (m, 6H), 2.56 (s, 6H), 2.18-2.03 (m, 6H), 1.72 (quin, J=7.4 Hz, 2H), 1.39-1.24 (m, 6H), 0.89 (t, J=6.8 Hz, 3H).

Example 27

(5Z,8Z,11Z,14Z)—N-(3-(5-methyl-4-(trifluoromethyl)thiazol-2-yl)bicyclo[1.1.1]pentan-1-yl)icosa-5,8,11,14-tetraenamide (27)

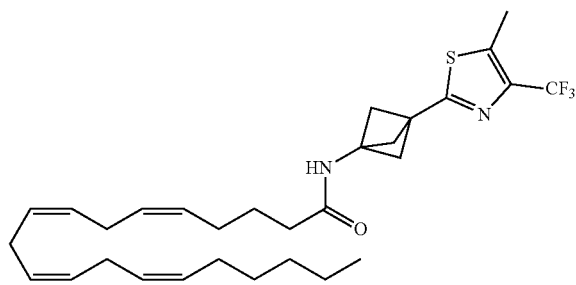 [SMILES: CCCCC/C=C\C/C=C\C/C=C\C/C=C\CCCC(=O)NC12CC(c3nc(C(F)(F)F)c(C)s3)(C1)C2]

The following operations were performed in a manner as to minimize exposure to light. A solution of (5Z,8Z,11Z,14Z)-icosa-5,8,11,14-tetraenoic acid (40 mg, 0.131 mmol) in DCM (0.9 mL) and DMF (10 μL) was cooled to 0° C. and oxalyl chloride (23 μl, 0.263 mmol) was added dropwise. The reaction mixture was stirred for an additional 1 h followed by the addition of a solution of Compound 2 (112 mg, 0.394 mmol) in pyridine (32 μL, 0.394 mmol). The mixture was warmed to rt and stirred for an additional 30 minutes. The mixture was diluted with DCM (5 mL) and washed with 10% aqueous HCl and water. The organic layer was dried (Na$_2$SO$_4$), concentrated and purified by flash chromatography (SiO$_2$, Hexanes/EtOAc) to provide 71 mg (>99%) of Compound 27 as a viscous pale yellow oil: $^1$H NMR (400 MHz, CDCl3) δ 5.84 (br s, 1H), 5.43-5.30 (m, 8H), 2.85-2.79 (m, 6H), 2.54 (q, J=1.8 Hz, 3H), 2.50 (s, 6H), 2.17-2.03 (m, 6H), 1.71 (quin, J=7.4 Hz, 2H), 1.40-1.24 (m, 6H), 0.89 (t, J=6.8 Hz, 3H).

Example 28

3-(trifluoromethyl)bicyclo[1.1.1]pentan-1-amine hydrochloride (28)

Compound 28 was obtained using a procedure described in U.S. Pub. No. 2016/0075654, which is herein incorporated by reference.

Example A

Formalin Paw Test

One test compound or the vehicle was administered to each rat or mouse in each test group (8 rats or mice per group). Non-fasted male Sprague-Dawley rats weighing 200-225 g or non-fasted male ICR mice weighing 23±3 g were used. Test compounds were administered at a concentration of 30 mg/kg or 60 mg/kg; morphine was administered at a concentration of 5 mg/kg; and acetaminophen was administered at a concentration of >300 mg/kg. The control group received the vehicle (9% PEG400/0.5% PVP/0.5% Tween-80/90% of 0.5% CMC in water) for rats or the vehicle (5% DMSO/15% PEG400/10% HPbCD/0.9% Saline) for mice. After 30 minutes, a 2% formalin solution (0.05 mL) was injected into one hind paw (sub-plantar) of each rat. For mice, after 10 minutes a 2% formalin solution (0.02 mL) was injected into one hind paw (sub-plantar) of each mouse. Responses were measured every 5 minutes after the formalin injection for 35 minutes. The results in Table 2 are for oral administration in rat and the results in Table 3 are for intraperitoneal administration in mouse. In Tables 2 and 3, 'A' designates <70 seconds of paw licking, 'B' designates >70 and <165 seconds of paw licking, and 'C' designates >165 seconds of paw licking.

The results are provided in Tables 2 and 3. As shown in Tables 2 and 3, compounds of Formulae (Ia), (Ib), (Ic), (Id), (Ie), (If), (Ig), (Ih), (Ik), (Im), (In), (Io), (Ip), (Iq), (Ir), (Is) and (It), or a pharmaceutically acceptable salt of any of the foregoing, significantly decreased the pain response in both the early/acute phase (0-10 minutes) and the late/tonic phase (10-35 minutes). The results indicate that compounds described herein have significant analgesic properties.

TABLE 2

| Compound No. | Dosage (mg/kg) | Early Phase | Late Phase |
|---|---|---|---|
| 1 | 30 | A | B |
| 2 | 30 | A | A |
| 3 | 30 | A | A |
| 4 | 30 | A | A |
| 5 | 30 | A | B |
| 6 | 30 | A | B |
| 7 | 30 | A | B |
| 8 | 30 | A | C |
| 9 | 30 | A | C |
| 10 | 30 | A | A |
| 11 | 30 | A | C |
| 12 | 30 | A | C |
| 13 | 30 | A | A |
| 14 | 30 | A | C |
| 15 | 30 | A | C |
| 16 | 30 | A | C |
| 17 | 30 | A | C |
| 18 | 30 | A | B |
| 19 | 30 | A | B |
| 20 | 30 | A | C |
| 21 | 30 | A | C |
| 22 | 30 | A | B |
| 25 | 30 | A | A |

TABLE 3

| Compound No. | Dosage (mg/kg) | Early Phase | Late Phase |
|---|---|---|---|
| 23 | 60 | A | C |
| 24 | 60 | A | B |

Example B

UVB Inflammatory Pain Test

UVB irradiation to the surface of the hind paw was used to induce cutaneous inflammatory pain in non-fasted male Sprague-Dawley rats weighing 175-300 g. On Day −3, animals were restrained and the plantar surface of the left hind paw was exposed to 350 mJoules/cm$^2$ of UVB irradiation using a narrow band UVB light source (Daavlin®, Bryan, Ohio). Following UVB irradiation, animals were returned to their home cage. Thermal hyperalgesia was assessed prior to dosing and approximately 1, 2, and 4 hours after dosing on Day 0 using a radiant heat plantar test apparatus (IITC Life Sciences©; Woodland Hills, Calif.). Animals were placed in individual acrylic chambers on a glass platform warmed to 30±2° C. and allowed to acclimate to their surroundings for a minimum of 15 minutes before testing. The stimulus was presented to the plantar surface and the timer was activated. The stimulus intensity was set such that pre-injury paw withdrawal latencies were approximately 12-18 seconds. Paw withdrawal latency values were recorded at the first observed nocifensive behavior (paw withdrawal, flinching, biting and/or licking). Three paw withdrawal latencies were measured for each hind paw per time point. The mean of the 3 values was taken as the paw withdrawal latency for that time point. A maximum cutoff latency of 30 seconds was used to prevent injury to the animal. The mean and standard error of the mean (SEM) were determined for each paw for each treatment group at each time point. Test compounds were administered orally at concentrations of 3, 10, 30 or 100 mg/kg; celecoxib was administered orally at a concentration of 30 mg/kg; and acetaminophen was administered orally at a concentration of 300 mg/kg. The control group received the vehicle (sterile water). In Table 4, 'A' designates >8 seconds of paw withdrawal latency, 'B' designates >6 and <8 seconds of paw withdrawal latency, and 'C' designates <6 seconds of paw withdrawal latency.

The results provided in Table 4 are for oral administration in rats. As shown in Table 4, compounds of Formulae (Ie), (Ih) and (Ik), or a pharmaceutically acceptable salt of any of the foregoing, significantly decreased the pain response at 1, 2 and 4 h. The results indicate that compounds described herein have at least comparable or improved inflammatory analgesic properties relative to those of acetaminophen and NSAIDs, such as celecoxib. Furthermore, while acetaminophen was dosed at 300 mg/kg, compounds of Formulae (Ie), (Ih) and (Ik), or a pharmaceutically acceptable salt of any of the foregoing, were dosed at 3 mg/kg, 10 mg/kg and 100 mg/kg. Thus, comparable or improved inflammatory analgesic properties were achieved at significantly lower doses of compounds described herein (such as approximately 100-fold, approximately 30-fold and approximately 3-fold) relative to that of acetaminophen. As a lower dose of compounds described herein are needed to achieve comparable or improved inflammatory analgesic properties, compounds described herein are expected to be better tolerated by a subject's body with compared to APAP.

TABLE 4

| Compound No. | Dosage (mg/kg) | 1 h | 2 h | 4 h |
| --- | --- | --- | --- | --- |
| 1 | 3 | B | B | B |
|   | 10 | B | B | B |
|   | 30 | A | A | A |
|   | 100 | A | A | A |
| 2 | 3 | A | A | A |
|   | 10 | A | B | A |
|   | 30 | A | A | B |
|   | 100 | A | A | A |

TABLE 4-continued

| Compound No. | Dosage (mg/kg) | 1 h | 2 h | 4 h |
| --- | --- | --- | --- | --- |
| 6 | 3 | C | B | A |
|   | 10 | B | B | B |
|   | 30 | A | B | B |
|   | 100 | A | A | B |
| 7 | 3 | B | B | B |
|   | 10 | C | C | B |
|   | 30 | B | B | B |
|   | 100 | C | C | B |
| Celecoxib | 30 | A | A | A |
| Acetaminophen | 300 | A | A | A |
| Vehicle | N/A | C | C | C |

Example C

Osteoarthritis Pain Test

Osteoarthritis pain was induced in non-fasted male Sprague-Dawley rats weighing 150-250 g by injecting 2 mg of monosodium iodoacetate (MIA) into the left knee joint. Mechanical hyperalgesia was measured using a digital Randall-Selitto device (dRS; IITC Life Sciences©; Woodland Hills, Calif.). Animals were allowed to acclimate to the testing room for a minimum of 15 minutes before testing. Animals were placed in a restraint sling that suspended the animal, leaving the hind limbs available for testing. The stimulus was applied to the knee joint by a blunt tip and pressure was applied gradually over approximately 10 seconds. Joint compression threshold values were recorded at the first observed nocifensive behavior (vocalization, struggle, or withdrawal). One reading per joint was taken at each time point, and a maximum stimulus cutoff of 500 grams was used to prevent injury to the animal. Mechanical hyperalgesia was assessed prior to MIA injection, and again 14 days later. After 14 days, test or control articles were administered once daily for 7 days with mechanical hyperalgesia assessed prior to dosing, 1, 2, and 4 hours post-dosing on days 0, 3, and 6. Test compounds were administered orally at concentrations of 3, 10, 30 or 100 mg/kg and celecoxib was administered orally at a concentration of 30 mg/kg. The control group received the vehicle (sterile water). After day 0, groups receiving the 100 mg/kg dose were reduced to a dose of 3 mg/kg. In Table 5, 'A' designates ≥375 grams of joint compression, 'B' designates ≥325 and <375 grams of joint compression, and 'C' designates <325 grams of joint compression.

The results provided in Table 5 are for oral administration in rats. As shown in Table 5, compounds of Formula (Ie), or a pharmaceutically acceptable salt of any of the foregoing, significantly decreased the pain response at 1, 2 and 4 h on days 0, 3 and 6. As shown by the data in Table 5, compounds described herein have comparable or improved osteoarthritis analgesic properties relative to those of NSAIDs, such as celecoxib. Furthermore, starting on day 3, comparable or improved osteoarthritis analgesic properties were achieved compared to celecoxib at all doses evaluated for the compounds described herein.

TABLE 5

| Compound No. | Dosage (mg/kg) | Day 0 | | | Day 3 | | | Day 6 | | |
|---|---|---|---|---|---|---|---|---|---|---|
| | | 1 h | 2 h | 4 h | 1 h | 2 h | 4 h | 1 h | 2 h | 4 h |
| 1 | 3 | — | — | — | A | A | A | A | B | A |
| | 10 | B | C | C | B | B | B | B | B | B |
| | 30 | B | B | B | A | A | B | A | B | B |
| | 100 | A | A | A | — | — | — | — | — | — |
| 2 | 3 | — | — | — | A | A | A | B | B | B |
| | 10 | C | C | C | B | A | C | B | B | A |
| | 30 | B | B | B | B | B | B | B | B | A |
| | 100 | A | A | A | — | — | — | — | — | — |
| Celecoxib | 30 | B | A | B | C | A | A | B | A | A |
| Vehicle | N/A | C | C | C | C | C | C | C | C | C |

Example D

Post-Incisional (Brennan) Pain Test

Incisional pain was induced in non-fasted male Sprague-Dawley rats weighing 180-300 g by making a 1-cm plantar incision in the left hind paw and is designed to mimic pain and sensitivity similar to what is reported by patients after surgery. Dosing occurred at the time of incision and spontaneous pain was measured 4 and 24 hours post-dosing using a cumulative pain score. The unrestrained animals were placed on a metal mesh platform and allowed to acclimate for about 15 min/ Each animal was closely observed during a 1-min period repeated every 5 min for 1 h (12 times total). Depending on the position in which the foot was found during the scoring period, a score of 0, 1, or 2 was given. Full weight bearing of the foot (score=0) was present if the skin on the plantar surface of the paw wound was blanched or distorted by the mesh. If the foot was completely off the mesh, or one or more instances of licking or flinching was observed, a score of 2 was recorded and the licking or flinching was noted but not counted. If the plantar surface of the paw touched the mesh without blanching or distorting, a score of 1 was given. The sum of the 12 scores obtained during the 1 h session was calculated (maximum score=24) for each animal. Observations were made during hours 4 and 24. Test articles were administered orally at concentrations of 10, 30 and ketoprofen was administered subcutaneously at a concentration of 10 mg/kg. The control group received the vehicle (sterile water). In Table 6, 'A' designates a cumulative pain score of ≤11, 'B' designates >11 and ≤16, and 'C' designates >16.

The results provided in Table 6 are for oral administration in rats. As shown in Table 6, compounds of Formula (Ie), or a pharmaceutically acceptable salt of any of the foregoing, significantly decreased the pain response at 4 and 24 h. The results in Table 6 demonstrate that compounds described herein have at least comparable or improved incisional analgesic properties compared to ketoprofen, an NSAID.

TABLE 6

| Compound No. | Dosage (mg/kg) | 4 h | 24 h |
|---|---|---|---|
| 1 | 10 | C | B |
| | 30 | A | A |
| | 100 | A | A |
| 28 | 10 | C | C |
| | 30 | B | B |
| | 100 | B | A |
| Ketoprofen | 10 | B | A |
| Vehicle | N/A | C | C |

Example E

Spinal Nerve Ligation (SNL) Neuropathic Pain Test

Neuropathy was induced in non-fasted male Sprague-Dawley rats weighing 75-100 g by surgically ligating the $4^{th}$ and $5^{th}$ lumbar spinal nerves (L4 and L5), a procedure also known as spinal nerve ligation (SNL). Animals were placed in individual acrylic chambers on a metal mesh surface and allowed to acclimate to their surroundings for a minimum of 15 minutes before testing. Mechanical sensitivity was assessed using 8 Semmes-Weinstein filaments (Stoelting©; Wood Dale, Ill., USA) with varying stiffness (0.4, 0.6, 1.0, 2.0, 4.0, 6.0, 8.0, and 15 g) according to an up-down method to determine 50% response thresholds. Each filament was presented perpendicular to the plantar surface with sufficient force to cause slight buckling against the paw and held for approximately 6 seconds or until a positive response is noted (paw sharply withdrawn). Testing was initiated with the 2.0 g filament. In the absence of a paw withdrawal response, the next stronger stimulus was presented. In the event of paw withdrawal, the next weaker stimulus was used. This process was repeated until 4 responses after the initial change in response (no response to positive response or positive response to no response) were obtained. If the animal did not respond after reaching the strongest filament or if the animal responded after reaching the weakest filament, the testing was stopped for that time point. The 50% response threshold was calculated using the formula:

$$50\% \text{ response threshold (g)} = (10^{(Xf+k\delta)})/10{,}000;$$

Xf=value (in log units) of the final von Frey filament used;
k=tabular value for the pattern of positive/negative responses (See Chaplan, et al. "Quantitative Assessment of Tactile Allodynia in the Rat Paw" *J. Neurosci. Meth.* 53.1 (1994): 56-63);
67 =mean difference (in log units) between stimuli.

The mean and standard error of the mean (SEM) were determined for each paw for each treatment group at each time point. Thresholds were determined prior to surgery and again 14 days later. After 14 days, test or control compounds were administered and thresholds were again determined 1, 2, and 4 hours after compound administration. Median response thresholds in compound-treated animals were compared to those in vehicle treated animals to determine anti-allodynic efficacy of test and control compounds. Test compounds were administered orally at concentrations of 10, 30 or 100 mg/kg and gabapentin was administered orally at a concentration of 100 mg/kg. The control group received the vehicle (sterile water). In Table 7, 'A' designates a 50% threshold of ≥8 grams, 'B' designates a 50% threshold of ≥6 and <8 grams, and 'C' designates a 50% threshold of <6 grams.

The results provided in Table 7 are for oral administration in rats. As shown in Table 7, compounds of Formula (Ie), or a pharmaceutically acceptable salt of any of the foregoing, significantly decreased the pain response at 1, 2 and 4 h. The data in Table 7 indicates that compounds described herein have at least comparable or improved neuropathic analgesic properties compared to gabapentin.

TABLE 7

| Compound No. | Dosage (mg/kg) | 1 h | 2 h | 4 h |
|---|---|---|---|---|
| 1 | 10 | C | C | C |
|   | 30 | B | B | C |
|   | 100 | A | A | A |
| 2 | 10 | C | C | C |
|   | 30 | C | C | C |
|   | 100 | A | A | B |
| Gabapentin | 100 | B | A | A |
| Vehicle | N/A | C | C | C |

Example F

NSAIDS and Opioid Receptor Test

Compounds were screened as DMSO solutions at 10 µM, 100 µM, or 200 µM and values represent percent inhibition of control-specific binding. Table 8 demonstrates the lack of significant in vitro activity of compounds of Formulae (Ie) and (Ir) or a pharmaceutically acceptable salt of any of the foregoing, against a panel of COX-1/COX-2 or opiate receptors. This data indicates that compounds described herein have a mechanism of action that is different from that of NSAIDs and opioids. As NSAID and opioid mechanisms of action are precluded, a person of ordinary skill in the art understands that undesirable side effects associated with inhibition of COX receptors in NSAIDs and activation of opiate receptors in opioids can be avoided by compounds described herein. Furthermore, opioids are known to lose their analgesic potency after to continued administration. (See Benyamin, et al. "Opioid Complications and Side Effects" *Pain Physician* 11 (2008): S105-S120). As the data indicates compounds described herein have a different mechanism action compared to opioids, a person of ordinary skill in the art would appreciate that compounds described herein would not be expected to lose their analgesic potency like opioids after continued admininistration.

TABLE 8

| | % Inhibition | | | | |
|---|---|---|---|---|---|
| Assay | APAP | Cmpd 1 | Cmpd 2 | | Cmpd 13 | Cmpd 28 |
| Name | 10 µM | 10 µM | 10 µM | 200 µM | 200 µM | 100 µM |
| COX-1 (human) | -7 | — | — | | 15 | 6 | — |
| COX-2 (human) | 3 | — | — | | -2 | 8 | — |
| Opiate δ₁ (human) | 2 | — | — | | — | — | — |
| Opiate δ₂ (human) | — | 7 | 10 | | — | 6 | 2 |
| Opiate κ (human) | -1 | -4 | -9 | | — | 33 | 1 |

TABLE 8-continued

| | % Inhibition | | | | |
|---|---|---|---|---|---|
| Assay | APAP | Cmpd 1 | Cmpd 2 | | Cmpd 13 | Cmpd 28 |
| Name | 10 µM | 10 µM | 10 µM | 200 µM | 200 µM | 100 µM |
| Opiate µ (human) | -5 | 11 | 9 | | — | 56 | 3 |

Example G

Conditioned Place Preference (Abuse) Test

A conditioned place preference (CPP) model was used to assess the reward properties of compounds of formulae (Ie), or a pharmaceutically acceptable salt of any of the foregoing, in adult male C57BL/6 mice. The CPP model apparatus consisted of a Plexiglas© test unit having three (A, B, C) compartments (9 cm×9 cm×16 cm) configured to allow access to all chambers. Compartments A and C had textually distinct flooring and wall marking. Mice were placed in the middle compartment with free access to the other compartments. On day 1 and 2, the "naive chamber preference" was assessed by placing the animal in the middle chamber twice a day (AM and PM) for 30 min on two consecutive days, with the chamber showing the greatest residence time being called the "preferred chamber". On "drug pairing days" (days 5, 6, 7 and 8) mice were injected IP with vehicle (50 mM citric acid) in the AM in the preferred chamber and the drug/vehicle in the afternoon in the non-preferred chamber for four consecutive days. On the morning of day 9 (the day after the last drug pairing), the "drug chamber preference" was assessed by placing the mouse (absent any injection) in the middle chamber, with free access to all chambers for 30 minutes. This was repeated five days later (day fourteen), with no intervening drug treatment.

The time spent on days 9 and 14 (e.g. day 0 and day 5 respectively after the last drug treatment) in the drug associated chamber was the test datum and is represented in FIG. 1. Mice undergoing least-preferred chamber pairing with morphine for 4 consecutive days displayed a significant increase in the least preferred chamber residence time (p <0.0001) on day 9 and on day 14 (1 and 5 days after the last drug treatment). In contrast, there was no increase in the non-preferred chamber residence time when the least-preferred chamber was paired with saline, APAP or test compounds 2 or 28 on either days 9 or 14, or days 0 or 5. These results indicate that compounds described herein are less likely to be abused or addictive relative to opioids, such as morphine.

Example H Bioavailability Test

Oral bioavailability of compounds of Formulae (Ie), (Ih), (Ik), and (Ir), or a pharmaceutically acceptable salt of any of the foregoing, were evaluated in fasted male Sprague-Dawley (SD) rats weighing 200-225g. Compounds were dosed at 3 mg/kg (IV) and 30 mg/kg (PO). Unless otherwise noted, compounds were dissolved in 0.9% saline for IV dosing and 100% sterile water for PO dosing. Pharmacokinetic parameters were determined using Phoenix WinNonlin (v7.0).

The results provided in Table 9 indicate that the compounds of Formulae (Ie), (Ih), (110, and (Ir), or a pharmaceutically acceptable salt of any of the foregoing, show favorable pharmacokinetic profiles, and a person of ordinary skill in the art would appreciate that the compounds of the present application may have improved metabolic stability relative to acetaminophen. For example, a person of ordinary skill in the art would appreciate that the compounds described herein demonstrate a longer metabolic half-life ($t_{1/2}$) than that of acetaminophen. (See Hirate et al., Biopharmaceutics & Drug Disposition (1990) 11:245-252). Therefore, compounds described can be dosed less often compared to a known NSAID, APAP and/or opioid.

TABLE 9

| Parameters | Cmpd 1 | | Cmpd 2 | | Cmpd 7 | |
|---|---|---|---|---|---|---|
| | IV | PO | IV | PO | IV | PO |
| $AUC_{inf}$ (µM · h) | 19.2 | 277 | 4.0 | 29 | 9.0 | 119 |
| CL (mL · min$^{-1}$ · kg$^{-1}$) | 11 | — | 52 | — | 27 | — |
| $V_{dss}$ (L/kg) | 1.4 | — | 3.6 | — | 2.5 | — |
| $C_{max}$ (µM) | — | 49 | — | 12 | — | 67 |
| $T_{max}$ (h) | — | 0.3 | — | 1.0 | — | 0.19 |
| $t_{1/2}$ (h) | 3.1 | 5.6 | 2.7 | 2.4 | 2.3 | 2.5 |
| F (%) | — | 115 | — | 79 | — | 138 |

| Parameters | Cmpd 6 | | Cmpd 13 | | Cmpd 25[a] | |
|---|---|---|---|---|---|---|
| | IV | PO | IV | PO | IV | PO |
| $AUC_{inf}$ (µM · h) | 1.8 | 29 | 3.0 | 35 | 13 | 144[b] |
| CL (mL · min$^{-1}$ · kg$^{-1}$) | 121 | — | 73 | — | 17 | — |
| $V_{dss}$ (L/kg) | 0.79 | — | 20.2 | — | 3.2 | — |
| $C_{max}$ (µM) | — | 32 | — | 11 | — | 24 |
| $T_{max}$ (h) | — | 0.22 | — | 0.6 | — | 1.2 |
| $t_{1/2}$ (h) | 0.15 | 1.6 | 9.5 | 6.8 | 3.7 | ND |
| F (%) | — | 134 | — | 16 | — | 115 |

[a]IV: DMSO, PEG400, and 30% HPβCD (5/20/75); PO: PEG400, PVP, Tween 80, 0.5% CMC in water (9/0.5/0.5/90).
[b]$AUC_{24h}$ Although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:

1. A compound selected from:

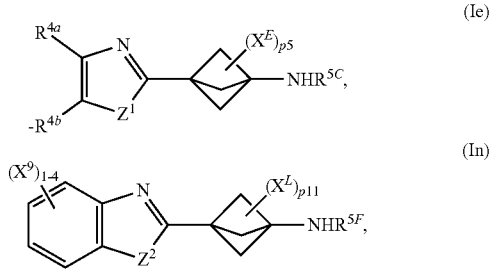

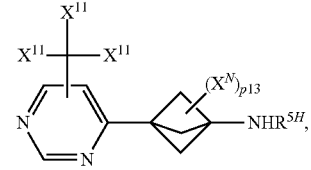

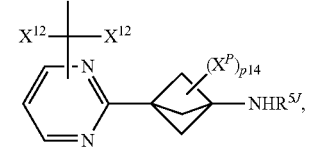

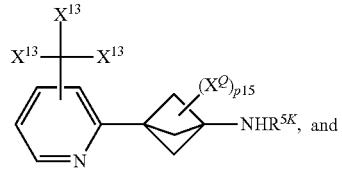

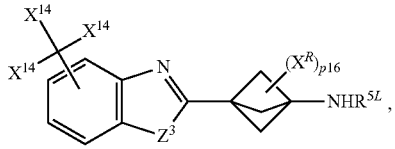

wherein:
each $X^{11}$, each $X^{12}$, each $X^{13}$, and each $X^{14}$ are independently hydrogen, deuterium, an unsubstituted $C_{1-4}$ alkyl, fluoro or chloro, provided that at least two of $X^{11}$ is fluoro or chloro, provided that at least two of $X^{12}$ is fluoro or chloro, provided that at least two of $X^{13}$ is fluoro or chloro, provided that at least two of $X^{14}$ is fluoro or chloro;
each $X^9$, is independently deuterium, fluoro or chloro;
$R^{5F}$, $R^{5H}$, $R^{5J}$, $R^{5K}$ and $R^{5L}$ are independently hydrogen, deuterium or an unsubstituted $C_{1-4}$ alkyl;
$R^{5C}$ is selected from the group consisting of hydrogen, deuterium, an unsubstituted $C_{1-4}$ alkyl and $C(=O)R^{12}$;
$R^{4a}$ and $R^{4b}$ are independently hydrogen, deuterium, an unsubstituted $C_{1-4}$ alkyl, a hydroxy substituted $C_{1-4}$ alkyl or —$C(X^{16})_3$, provided that at least one of $R^{4a}$ and $R^{4b}$ is —$C(X^{16})_3$;
$R^{12}$ is selected from the group consisting of hydrogen, deuterium, an unsubstituted $C_{1-30}$ alkyl and an unsubstituted $C_{2-30}$ alkenyl;
each $X^{16}$ is independently hydrogen, deuterium, an unsubstituted $C_{1-4}$ alkyl, fluoro or chloro, provided that at least two of $X^{16}$ is fluoro or chloro;
$Z^1$, $Z^2$ and $Z^3$ are independently nitrogen, oxygen or sulfur;
each $X^E$, each $X^L$, each $X^N$, ech $X^P$, each $X^Q$, each $X^R$ are independently deuterium, chloro or fluoro; and
p5, p11, p13, p14, p15 and p16 are independently 0, 1, 2, 3, 4, 5 or 6;
or a pharmaceutically acceptable salt thereof.

2. The compound of claim 1, or a pharmaceutically acceptable salt thereof, of Formula (Ie).

3. The compound of claim 2, or a pharmaceutically acceptable salt thereof, wherein $R^{4a}$ is —$C(X^{16})_3$; and $R^{4b}$ is hydrogen.

4. The compound of claim 2, or a pharmaceutically acceptable salt thereof, wherein the compound is selected from the group consisting of

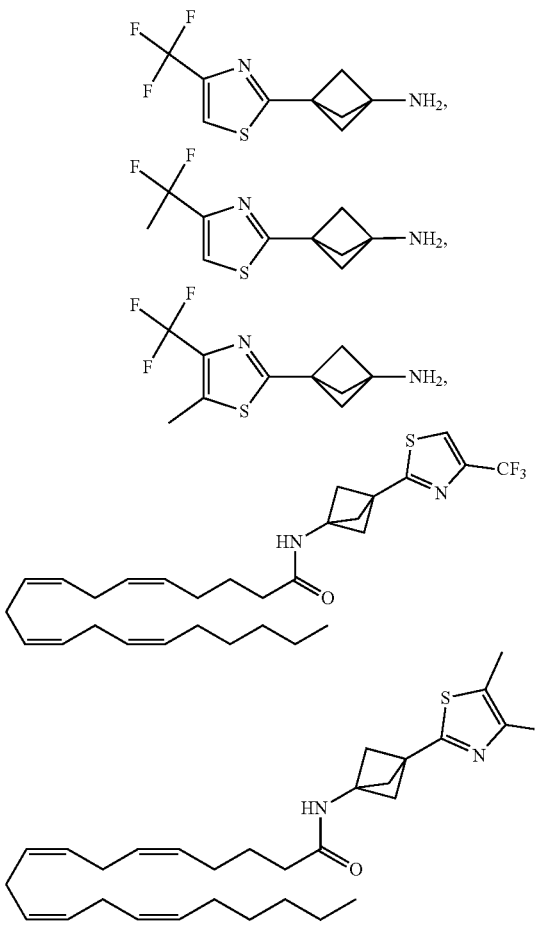

or a pharmaceutically acceptable salt of any of the foregoing.

5. The compound of claim 2, or a pharmaceutically acceptable salt thereof, wherein $R^{5C}$ is C(=O)$R^{12}$.

6. A method for reducing or at least partially preventing pain or fever comprising administering an effective amount of a compound of claim 1, or a pharmaceutically acceptable salt thereof, to a subject in need thereof.

7. A method for reducing or at least partially preventing pain or fever comprising contacting a cell in the central and/or peripheral nervous system of a subject with an effective amount of a compound of claim 1, or a pharmaceutically acceptable salt thereof, to a subject in need thereof.

8. The method of claim 6, further comprising providing at least one of an opioid analgesic and a non-steroidal anti-inflammatory drug (NSAID).

9. The method of claim 8, wherein the opioid analgesic is selected from the group consisting of morphine, codeine, hydrocodone, oxycodone, fentanyl, pethidine, methadone, pentazocine, sufentanil, levorphanol, dihydrocodeine, nalbuphine, butorphanol, tramadol, meptazinol, buprenorphine, dipipanone, alfentanil, remifentanil, oxymorphone, tapentadol, propoxyphene and hydromorphone; and wherein the NSAID is selected from the group consisting of celecoxib, ketorolac, ketoprofen, indomethacin, sulindac, etodolac, mefenamic acid, meclofenamic acid, meclofenamate sodium, flufenamic acid, tolmetin, diclofenac, diclofenac sodium, ibuprofen, naproxen, naproxen sodium, fenoprofen, flurbiprofen, oxaprozin, piroxicam, meloxicam, ampiroxicam, droxicam, lornoxicam, cinnoxicam, sudoxicam, and tenoxicam.

10. The method of claim 6, wherein the pain is selected from the group consisting of acute pain, post-operative pain, chronic pain, nociceptive pain, osteoarthritis, rheumatoid arthritis, neuropathic pain, migraine, visceral pain, mixed pain, lower back pain, cancer pain and fibromyalgia pain.

11. The compound of claim 2, wherein $Z^1$ is sulfur.

12. The compound of claim 11, wherein p5 is 0.

13. The compound of claim 11, wherein $R^{5C}$ is hydrogen.

14. The compound of claim 2, or a pharmaceutically acceptable salt thereof, wherein $R^{4a}$ is —C($X^{16}$)$_3$; and $R^{4b}$ is an unsubstituted $C_{1-4}$ alkyl.

15. The compound of claim 3, wherein each $X^{16}$ is fluoro.

16. The compound of claim 14, wherein each $X^{16}$ is fluoro.

17. The compound of claim 4, or a pharmaceutically acceptable salt thereof, wherein the compound is

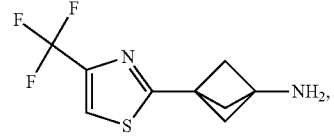 [SMILES: NC12CC(c3nc(C(F)(F)F)cs3)(C1)C2]

or a pharmaceutically acceptable salt thereof.

18. The compound of claim 4, or a pharmaceutically acceptable salt thereof, wherein the compound is

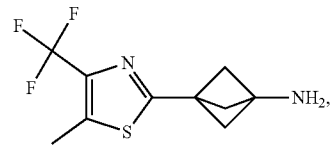 [SMILES: Cc1sc(C23CC(N)(C2)C3)nc1C(F)(F)F]

or a pharmaceutically acceptable salt thereof.

19. The compound of claim 4, or a pharmaceutically acceptable salt thereof, wherein the compound is

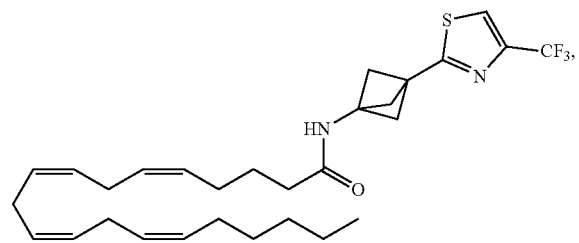 [SMILES: CCCCC/C=C\C/C=C\C/C=C\C/C=C\CCCC(=O)NC12CC(c3nc(C(F)(F)F)cs3)(C1)C2]

or a pharmaceutically acceptable salt thereof.

20. The compound of claim 4, or a pharmaceutically acceptable salt thereof, wherein the compound is

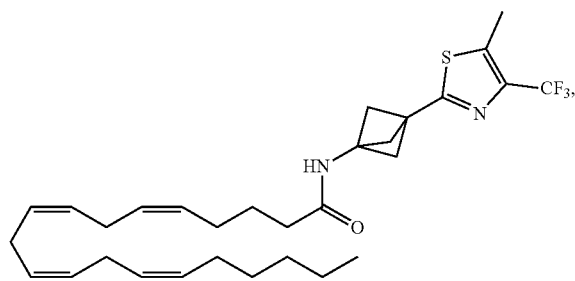 [SMILES: CCCCC/C=C\C/C=C\C/C=C\C/C=C\CCCC(=O)NC12CC(c3nc(C(F)(F)F)c(C)s3)(C1)C2]

or a pharmaceutically acceptable salt thereof.

21. The compound of claim 1, or a pharmaceutically acceptable salt thereof, wherein the compound is selected from the group consisting of

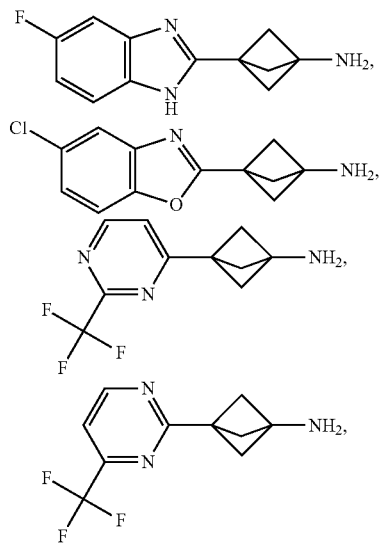

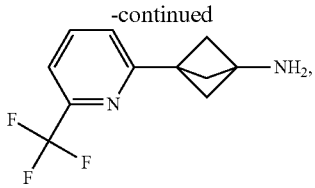

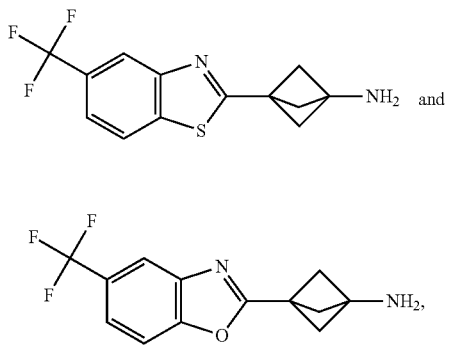

or a pharmaceutically acceptable salt of any of the foregoing.

22. The compound of claim 5, wherein $R^{12}$ is an unsubstituted $C_{14-22}$ alkenyl.

23. The compound of claim 22, wherein $R^{12}$ is selected from the group consisting of $-(CH_2)_7CH=CHCH_2CH=CH(_2)_4CH_3$, $-(CH_2)_7$, $CH=CH(CH_2)_7,CH_3$, $-(CH_2)_7CH=CHCH_2CH=CH(CH_2)_4CH_3$, $-(CH_2)_7CH=CH(CH_2)_7 CH_3$, $-(CH_2)_7CH=CHCH_2CH=CHCH_2CH=CHCH_2CH_3$, $-(CH_2)_9CH=CH(CH_2)_5CH_3$, $-(CH_2)_3CH=CHCH_2CH=CHCH_2CH=CHCH_2CH=CH(CH_2)_4CH_3$, $-(CH_2)_{11}CH=CH(CH_2)_7CH_3$, $-(CH_2)_3CH=CHCH_2CH=CHCH_2CH=CHCH_2 CH=CHCH_2CH=CHCH_2CH_3$ and $-(CH_2)_2 CH=CHCH_2CH=CHCH_2CH=CHCH_2CH=CHCH_2CH=CHCH_2CH_3$.

\* \* \* \* \*

UNITED STATES PATENT AND TRADEMARK OFFICE
CERTIFICATE OF CORRECTION

PATENT NO. : 11,242,327 B2
APPLICATION NO. : 16/613397
DATED : February 8, 2022
INVENTOR(S) : Chad Daniel Hopkins It is certified that error appears in the above-identified patent and that said Letters Patent is hereby corrected as shown below:

In the Specification

Column 4, Line 59-65, delete "For example, in the following structure, rings A and B are fused 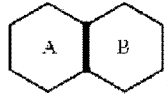." and insert the same on Column 4, Line 58, after "common." as a continuation of the same paragraph.

Column 6, Line 50, delete "thiamorpholine, thiamorpholine" and insert -- thiomorpholine, thiomorpholine --.

Column 6, Line 50-51, delete "thiamorpholine" and insert -- thiomorpholine --.

Column 14, Line 1, delete "—(CH$_2$)$_m$;" and insert -- —(CH$_2$)$_m$-; --.

Column 14, Line 14, delete "XJ," and insert -- XH, --.

Column 17, Line 41-53, delete " 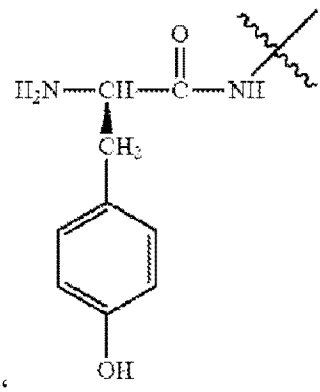 " and insert

Signed and Sealed this
Eighth Day of November, 2022

*Katherine Kelly Vidal*
Katherine Kelly Vidal
*Director of the United States Patent and Trademark Office*

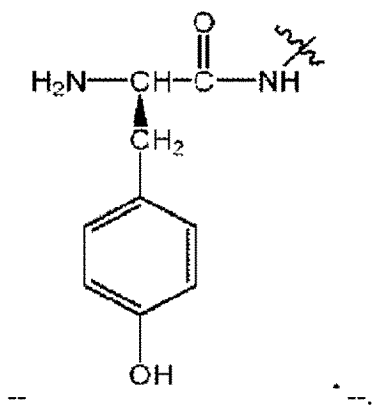

Column 23, Line 36, delete "CHCH$_2$ CH" and insert -- CHCH$_2$CH --.

Column 23, Line 40-41, delete "= CHCH$_2$CH" and insert -- =CHCH$_2$CH --.

Column 23, Line 64, delete "linoleiaidic" and insert -- linolelaidic --.

Column 28, Line 23, delete "C1-4" and insert -- C$_{1-4}$ --.

Column 37, Line 26, delete "deuerium," and insert -- deuterium, --.

Column 38, Line 26, delete "CH= CH" and insert -- CH=CH --.

Column 38, Line 29, delete "CHCH$_2$ CH" and insert -- CHCH$_2$CH --.

Column 38, Line 44, delete "C(O)R$^{11}$" and insert -- C(=O)R$^{11}$ --.

Column 38, Line 58, delete "linoleiaidic" and insert -- linolelaidic --.

Column 39, Line 26, delete "C3_20" and insert -- C3-20 --.

Column 39, Line 65, delete "CH$_2$ CH=" and insert -- CH$_2$CH= --.

Column 39, Line 67, delete "CH= CHCH$_2$CH=" and insert -- CH=CHCH$_2$CH= --.

Column 39, Line 67, delete "CHCH$_2$ CH" and insert -- CHCH$_2$CH --.

Column 41, Line 49, delete "(Ik)," and insert -- (Iq), --.

Column 42, Line 50, delete "chloronated." and insert -- chlorinated. --.

Column 47, Line 47, delete "musculo- skeletal" and insert -- musculo-skeletal --.

Column 57, Line 55, delete "R$_B$ F" and insert -- RBF --.

CERTIFICATE OF CORRECTION (continued)
U.S. Pat. No. 11,242,327 B2

Column 57, Line 65, delete "$R_B$ F." and insert -- RBF. --.

Column 58, Line 26, delete "41 4" and insert -- 41.4 --.

Column 58, Line 36, delete "27 6" and insert -- 27.6 --.

Column 59, Line 60, delete "stiffing" and insert -- stirring --.

Column 59, Line 62, delete "stiffing" and insert -- stirring --.

Column 60, Line 34, delete "stiffing." and insert -- stirring. --.

Column 60, Line 35, delete "stiffing" and insert -- stirring --.

Column 60, Line 36, delete "stiffing" and insert -- stirring --.

Column 61, Line 38 (approx.), delete "$[C_{21}H_{12}F_3N+H]+$." and insert -- $[C_{12}H_{12}F_3N+H]+$. --.

Column 62, Line 16 (approx.), delete "$C_{16}H_9O+H]^+$." and insert -- $C_5H_9O+H]^+$. --.

Column 62, Line 18 (approx.), delete "mmol) ," and insert -- mmol), --.

Column 62, Line 45 (approx.), delete "3-(3-(trifluoromethyl)phenybbicyclo" and insert -- 3-(3-(trifluoromethyl)phenyl)bicyclo --.

Column 63, Line 54, delete "stiffing." and insert -- stirring. --.

Column 64, Line 1, delete "Stiffing" and insert -- Stirring --.

Column 64, Line 11, delete "$[C_8H_{10}F_2NO+H]^+$." and insert -- $[C_8H_{10}F_3NO+H]^+$. --.

Column 64, Line 27 (approx.), delete "64 Ommol)" and insert -- 64.0 mmol) --.

Column 64, Line 41, delete "$[C_{22}H_{18}F_3NO_2—C_4H_8+H]^+$." and insert -- $[C_{12}H_{18}F_3NO_2—C_4H_8+H]^+$. --.

Column 65, Line 11, delete "$[C_{13}H_{20}F_3NO_2.C_5H_8O_2+H]^+$." and insert -- $[C_{13}H_{20}F_3NO_2-C_5H_8O_2+H]^+$. --.

Column 65, Line 55-56, delete "$[C_{19}H_{34}F_3NO_3.C_5H_8O_230 H]^+$." and insert -- $[C_{19}H_{34}F_3NO_3-C_5H_8O_2+H]^+$. --.

Column 67, Line 50, delete "6-69.06;" and insert -- δ -69.06; --.

Column 68, Line 55, delete "min" and insert -- min. --.

Column 69, Line 48, delete "mmol) ," and insert -- mmol), --.

CERTIFICATE OF CORRECTION (continued)
U.S. Pat. No. 11,242,327 B2

Column 70, Line 39, delete "DMSO-d6)" and insert -- DMSO-$d_6$) --.

Column 71, Line 10 (approx.), delete "345-" and insert -- 3-(5- --.

Column 73, Line 31, delete "mmol) ," and insert -- mmol), --.

Column 73, Line 63, delete "stiffing." and insert -- stirring. --.

Column 73, Line 65, delete "stiffing." and insert -- stirring. --.

Column 74, Line 67, delete "stiffing." and insert -- stirring. --.

Column 75, Line 4, delete "stiffing." and insert -- stirring. --.

Column 75, Line 27, delete "$Et_{20}$" and insert -- $Et_2O$ --.

Column 75, Line 28, delete "stiffing." and insert -- stirring. --.

Column 75, Line 29, delete "$Et_{20}$" and insert -- $Et_2O$ --.

Column 75, Line 30, delete "stiffing." and insert -- stirring. --.

Column 75, Line 31, delete "$Et_{20}$." and insert -- $Et_2O$. --.

Column 75, Line 36, delete "ExampleS" and insert -- Examples --.

Column 75, Line 63, delete "$Et_{20.}$" and insert -- $Et_2O$ --.

Column 75, Line 63, delete "29 4" and insert -- 29.4 --.

Column 76, Line 11, delete "stiffing." and insert -- stirring. --.

Column 76, Line 65, delete "stiffing." and insert -- stirring. --.

Column 77, Line 9, delete "stiffing." and insert -- stirring. --.

Column 77, Line 11, delete "stiffing." and insert -- stirring. --.

Column 78, Line 23, delete "mmol) ," and insert -- mmol), --.

Column 78, Line 63, delete "stiffing." and insert -- stirring. --.

Column 80, Line 18, delete "$[C_{18}H_{20}F_2N_2O_2S+H]^+$." and insert -- $[C_{15}H_{20}F_2N_2O_2S+H]^+$. --.

Column 82, Line 6, delete ">300" and insert -- ≥300 --.

Column 82, Line 18, delete ">70" and insert -- ≥70 --.

Column 82, Line 19, delete ">165" and insert -- ≥165 --.

Column 83, Line 31 (approx.), delete ">8" and insert -- ≥8 --.

Column 83, Line 32 (approx.), delete ">6" and insert -- ≥6 --.

Column 85, Line 28 (approx.), delete "min/" and insert -- min. --.

Column 86, Line 54, delete "67" and insert -- δ --.

Column 87, Line 50, delete "admininistration." and insert -- administration. --.

Column 88, Line 66, delete "(110," and insert -- (Ik), --.

In the Claims

Column 90, Line 16-24 (approx.), Claim 1, delete " 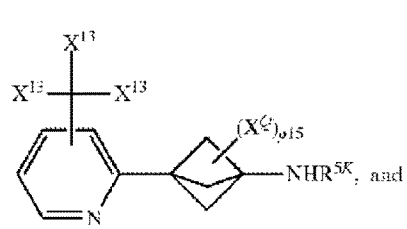 "

and insert -- 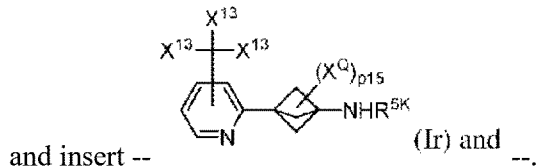 --.

Column 90, Line 33, In Claim 1, delete "$X^{13}$," and insert -- $X^{13}$ --.

Column 90, Line 40, In Claim 1, delete "$X^9$ ," and insert -- $X^9$ --.

Column 90, Line 58, In Claim 1, delete "ech" and insert -- each --.

Column 90, Line 58, In Claim 1, delete "$X^Q$," and insert -- $X^Q$ and --.

Column 94, Line 33, In Claim 23, delete "CH$(_2)_4$CH$_3$," and insert -- (CH$_2$)$_4$CH$_3$, --.

Column 94, Line 33, In Claim 23, delete "—(CH$_2$)$_7$, CH=CH(CH$_2$)$_7$,CH$_3$," and insert -- —(CH$_2$)$_7$CH=CH(CH$_2$)$_7$CH$_3$, --.

Column 94, Line 39, In Claim 23, delete "CHCH$_2$ CH" and insert -- CHCH$_2$CH --.